US008269065B2

(12) United States Patent
Privat et al.

(10) Patent No.: US 8,269,065 B2

(45) Date of Patent: Sep. 18, 2012

(54) NUCLEIC ACIDS AND PROTEINS ASSOCIATED WITH SUCROSE DEGRADATION IN COFFEE

(75) Inventors: Isabelle Muguette Privat, Tours (FR); James Gèrard McCarthy, Noizay (FR); Vincent Petiard, Tours (FR); Steven D. Tanksley, Dryden, NY (US); Chenwei Lin, Menlo Park, CA (US)

(73) Assignees: Nestec, S.A., Vevey (CH); Cornell University, Ithaca, NY (US)

( * ) Notice: Subject to any disclaimer, the term of this patent is extended or adjusted under 35 U.S.C. 154(b) by 509 days.

(21) Appl. No.: 11/992,612

(22) PCT Filed: Sep. 27, 2006

(86) PCT No.: PCT/US2006/037600

§ 371 (c)(1), (2), (4) Date: Mar. 8, 2010

(87) PCT Pub. No.: WO2007/038566

PCT Pub. Date: Apr. 5, 2007

(65) Prior Publication Data

US 2010/0154074 A1 Jun. 17, 2010

Related U.S. Application Data

(60) Provisional application No. 60/720,865, filed on Sep. 27, 2005.

(51) Int. Cl.

| | |
|---|---|
| ***A01H 5/00*** | (2006.01) |
| ***C12N 15/63*** | (2006.01) |
| ***C12N 15/82*** | (2006.01) |
| ***C12P 19/34*** | (2006.01) |

(52) U.S. Cl. ....... 800/284; 800/298; 536/23.2; 435/419; 435/320.1

(58) Field of Classification Search ........................ None
See application file for complete search history.

(56) References Cited

U.S. PATENT DOCUMENTS 6,713,666 B2 * 3/2004 Helentjaris et al. ........ 800/320.1

FOREIGN PATENT DOCUMENTS

| | | | |
|---|---|---|---|
| WO | WO/92/14831 | * | 3/1992 |
| WO | WO 98/04722 | A | 2/1998 |
| WO | WO 01/58939 | A | 8/2001 |
| WO | WO0158939 | * | 8/2001 |
| WO | WO/2004/113520 | * | 12/2004 |
| WO | WO 2005/004585 | A | 1/2005 |

OTHER PUBLICATIONS

Hothorn et al, The Plant Cell, vol. 16 3437-3447 (2004).*
Guo et al, PNAS 2004 (101)25,9205-9210.*
Wolf et al FEBS Letters 555 (2003) 551-555.*
Marraccini et al (Plant Physiology and Biochemistry, vol. 37 (4) Apr. 1999, 273-282).*
Baltes et al (J. Agric. Food Chem, 1987, 35 340-346).*
Rogers et al (Plant Science 149 (1999) 115-123).*
Feldman et al (vol. 17, No. 4 Jul.-Aug. 1969.*
Rausch et al—Biochemistry and Biophysics 1696 (2004) 253-261.*
Altschul, S.F. et al., 1990, "Gapped BLAST and PSI-BLAST: A New Generation of Protein Database Search," *Nucleic Acids Res*., vol. 25, pp. 3389-3402.
Arabidopsis Genome Initiative. 2000, "Analysis of the Genome Sequence of the Flowering Plant *Arabidopsis Thaliana," Nature*. vol. 408, pp. 796-815.
Bate, N.J. et al., 2004, "An Invertase Inhibitor From Maize Localizes to the Embryo Surrounding Region During Early Kernel Development," *Plant Physiol.*, vol. 134, pp. 246-254.
Benamor, M. and Mc Carthy, J. 2003. "Modulation of Coffee Flavour Precursor Levels in Green Coffee Grains," European Patent Application No. 03394056.0 NESTEC S.A.
Chahan,Y. et al.,. 2002, "From the Green Bean to the Cup of Coffee: Investing Coffee Roasting by On-Line Monitoring of Volatiles," *Eur Food Res Technol.*, vol. 214, pp. 92-104.
Cheng, W.H. et al., 1996, "The *Miniature1* Seed Locus of Maize Encodes a Cell Wall Invertase Required for Normal Development of Endosperm and Maternal Cells in the Pedicel," *Plant Cell.* vol. 8. pp. 971-983.
Clough, S.J. and Bent A.F. 1998, "Floral Dip: A Simplified Method for *Agrobacterium*-Mediated Transformation of *Arabidopsis Thaliana," Plant Journal*, vol. 16; pp. 735-743.
Crouzillat, D. et al., 1996, "Theobroma Cacao L.: A Genetic Linkage Map and Quantitative Trait Loci Analysis," *Theor Appl Genet.*, vol. 93, pp. 205-214.
Dali, N. et al., 1992, "Evidence for the Involvement of Sucrose Phosphate Synthase in the Pathway of Sugar Accumulation in Sucrose-Accumulating Tomato Fruits," *Plant Physiol.*, vol. 99, pp. 434-438.
Dickinson, C.D. et al., 1991, "Slow Growth Phenotype of Transgenic Tomato Expressing Apoplastic Invertase.,"*Plant Physiol.*,vol. 95, pp. 420-425.
Fridman, E. and Zamir, D. 2003, "Functional Divergence of a Synthetic Invertase Gene Family in Tomato, Potato and Arabidopsis," *Plant Physiol.*, vol. 131, pp. 603-609.
Fridman, E. et al., 2004, "Zooming in on a Quantitative Trait for Tomato Yield Using Interspecific Introgressions," *Science*, vol. 305(5691), pp. 1786-1789.
Godt, D. E. et T. Roitsch. 1997, Regulation and Tissue-Specific Distribution of mRNAs for Three Extracellular Invertase Isoenzymes of Tomato Suggests an Important Function in Establishing and Maintaining Sink Metabolism, *Plant Physiol.*, vol. 115, pp. 73-282.
Grandillo, S. and Tanksley S.D. 1996, "QTL Analysis of Horticultural Traits Differentiating the Cultivated Tomato Fruit From the Closely Related Species *Lycopersicon Pimpinellifolium," Theor Appl Gene.*, vol. 92, pp. 935-951.

(Continued)

*Primary Examiner* — Brent T. Page
*Assistant Examiner* — Lee A Visone
(74) *Attorney, Agent, or Firm* — Potter Anderson & Corroon, LLP

(57) ABSTRACT

Disclosed herein are nucleic acid molecules isolated from coffee (*Coffea* spp.) comprising sequences that encodes various sucrose metabolizing enzymes, along with their encoded proteins. Specifically, three types of invertase and four invertase inhibitors and their encoding polynucleotides from coffee are disclosed. Also disclosed are methods for using these polynucleotides for gene regulation and manipulation of the sugar profile of coffee plants, to influence flavor, aroma, and other features of coffee beans.

16 Claims, 9 Drawing Sheets

OTHER PUBLICATIONS

Greiner, S. et al., 1998, "Cloning of a Tobacco Apoplasmic Invertase Inhibitor. Proof of Function of the Recombinant Protein and Expression Analysis During Plant Development,"*Plant Physiol.*, vol. 1116, pp. 733-742.

Greiner, S.et al., 1999, "Ectopic Expression of a Tobacco Invertase Inhibitor Homolog Prevents Cold-Induced Sweetening of Potato Tubers," *Nature Biotech.*, vol. 17, pp. 708-711.

Greiner, S. Et al., 2000, "Plant Invertase Inhibitors: Expression in Cell Culture and During Plant Development," *Australian Journal of Plant Physiology*, vol. 27, pp. 807-814.

Holscher, W. and Steinhart, H. 1995, Aroma Compounds in Green Coffee,. Elsevier, 785-803.

Hothorn, M. et al., 2003, "Bacterial Expression, Purification and Preliminary X-Ray Crystallographic Characterization of the Invertase Inhibitor Nt-CIF From Tobacco," *Acta Cryst*, vol. D59, pp. 2279-2282.

Hothorn, M. et al., 2004, "Structural Insights into the Target Specificity of Plant Invertase and Pectin Methylesterase Inhibitory Proteins," *Plant Cell*, vol. 16, pp. 3437-3447.

King, S.P. et al., 1997. "Carbohydrate Content and Enzyme Metabolism in Developing Canola Siliques,"*Plant Physiol.*, vol. 114, pp. 153-160.

Klann, E. et al., 1992, "Tomato Acid Invertase Complementary DNA," *Plant Physiol.*, vol. 99, pp. 351-353.

Klann, E.M. et al., 1993, "Expression of Acid Invertase Gene Controls Sugar Composition in Tomato (*Lycopersicon*) Fruit," *Plant Physiol.*, vol. 103, pp. 863-870.

Klann, E.M. et al., 1996, "Antisense Acid Invertase (*TIV1*) Gene Alters Soluble Sugar Composition and Size in Transgenic Tomato Fruit," *Plant Physiol.*, vol. 112, pp. 1321-1330.

Lowe, J. and Nelson, O.E., Jr. 1946, "Miniature Seed- A Study in the Development of a Defective Caryopsis in Maize," *Genetics*, vol. 31, pp. 525-533.

Marraccini, P. et al., 1999, Molecular Cloing of the Complete 11S Seed Storage Protein Gene of *Coffea Arabica* and Promoter Analysis in Transgenic Tobacco Plants, *Plant Physiol. Biochem*, vol. 37, pp. 273-282.

Marraccini, P. et al., 2003, "Rubisco Small Subunit of *Coffea Arabica*: Cdna Sequence, Gene Cloning and Promoter Analysis in Transgenic Tobacco Plants," *Plant Physiol. Biochem.*, vol. 41, pp. 17-25.

Miller, M.E. and Chourey, P.S. 1992., "The Maize Invertase-Deficient *Miniature-1* Seed Mutation is Associated With Aberrant Pedicel and Endosperm Development," *Plant Cell*, vol. 4, pp. 297-305.

N'Tchobo H. et al., "Starch Synthesis in Tomato Remains Constant Throughout Fruit Development and is Dependent on Sucrose Supply and Sucrose Synthase Activity," *Journal of Experimental Botany*, vol. 50(338), pp. 1457-1463, 1999.

Nguyen-Quoc, B. and C. H. Foyer. 2001, "A Role for 'Futile Cycles' Involving Invertase and Sucrose Synthase in Sucrose Metabolism of Tomato Fruit," *J. Exp. Bot.* vol. 52, pp. 881-889.

Ohyama, A. et al. 1995, "Suppression of Acid Invertase Activity by Antisense RNA Modifies the Sugar Composition of Tomato Fruit," *Plant Cell Physiol.*, vol. 36, pp. 369-376.

Rausch, T. and Greiner S. 2004, "Plant Protein Inhibitors of Invertases," *Biochimica et Biophysica Acta*. vol. 1696, pp. 253-261.

Robinson, N.L. et al., 1998, "Sink Metabolism in Tomato Fruit," *Plant Physiol.* vol. 87, pp. 732-730.

Rogers, W. J. et al., 1999, "Changes to the Content of Sugars, Sugar Alcohols, Myo-Inositol, Carboxylic Acids and Inorganic Anions in Developing Grains From Different Varieties of Robusta (*Coffea Canephora*) and Arabica (*C. arabica*) Coffees," *Plant Sc.* vol. 149, pp. 115-123.

Roitsch, T. and Gonzalez M-C., 2004, "Function and Regulation of Plant Invertases: Sweet Sensations," *Trends in Plant Science*, vol. 9(12), pp. 606-613.

Russwurm, H. 1969, "Fractionation and Analysis of Aroma Precursors in Green Coffee," ASIC, vol. 4, pp. 103-107.

Scholes, J. et al., 1996, "The Impact of Reduced Vacuolar Invertase Activity on the Photosynthetic and Carbohydrate Metabolism of Tomato.," *Planta*, vol. 200, pp. 265-272.

Scognamiglio, M.A. et al., 2003, "The Plant Invertase Inhibitor Shares Structural Properties and Disulfide Bridges Arrangement With the Pectin Methylesterase Inhibitor," *Journal of Protein Chemistry*, vol. 22(3), pp. 363-369.

Sturm, A. et al., 1990, "cDNA Cloning of Carrot Extracellular β-Fructosidase and its Expression in Response to Wounding and Bacterial Infection," *Plant Cell*, vol. 2, pp. 1107-1119.

Sun, J. et al., 1992, "Sucrose Synthase in Wild Tomato, Lycopersicon Chmielewskii, and Tomato Fruit Sink Strength," *Plant Physiol.*, vol. 98, pp. 1163-1169.

Tang, G.Q. et al., 1999, "Antisense Repression of Vacuolar and Cell Wall Invertase in Transgenic Carrot Alters Early Plant Development and Sucrose Partitioning," *Plant Cell*, vol. 11, pp. 177-189.

Tanksley, S.D. et al., 1990, "Advanced Backcross QTL Analysis in a Cross Between an Elite Processing Line of Tomato and its Wild Relative *L. Pimpinellifolium," Theor Appl Gene*, vol. 92, pp. 213-224.

Von Schaewen, A. et al., 1990, "Expression of Yeast-Derived Invertase in the Cell Wall of Tobacco and Arabidopsis Plants Leads to Accumulation of Carbohydrate and Inhibition of Photosynthesis and Strongly Influences Growth and Phenotype of Transgenic Tobacco Plants," *EMBO J.*, vol. 9, pp. 3033-3044.

Wang, F. et al., 1993, "Sucrose Synthase Starch Accumulation and Tomato Fruit Sink Strength," *Plant Physiol.*, vol. 101, pp. 321-327.

Weil, M. et al., 1994, "A 17-kDa *Nicotiana Tabacum* Cell-Wall Peptide Acts as an In Vitro Inhibitor of the Cell-Wall Isoform of Acid Invertase," *Planta.*, vol. 193, pp. 438-445.

Yau, YY and Simon P.W. 2003, "A 2.5 Kb Insert Eliminates Acid Soluble Invertase Isozyme II Transcript in Carrot (Daucus Carota L.) Rots, Causing High Sucrose Accumulation," *Plant Mol. Biol.*, vol. 53,pp. 151-162.

Yelle, S. et al., 1991, "Sink Metabolism in Tomato Fruit. Genetic and Biochemical Analysis of Sucrose Accumulation," *Plant Physiol.*, vol. 95, pp. 1026-1036.

Ziegler, H. 1975, "Nature of transported substances," *Encyclopedia of Plant Physiology.* vol. 1-3, pp. 59-100.

Zrenner, R., et al., 1995, "Evidence of the Crucial Role of Sucrose Synthase for Sink Strength Using Transgenic Potato Plants (*Solanum Tuberosum* L.)," *Plant J.*, vol. 7, pp. 97-107.

Database UniProt [Online] OS Fragaria ananassa (Strawberry), May 1, 1999, "Cell Wall Invertase Precursor," XP002419645, retrieved from EBI accession No. UNIPROT: Q9ZP42_FRAAN, Database accession No. Q09ZP42, abstract; sequences.

Database-UniProt [Online] EBI: Arabidopsis thaliana (Mouse-ear cress), Nov. 1, 1996, "Beta-fructofuranosidase (EC 3.2.1.26)" XP002419646, retrieved from EBI accession No. UNIPROT:Q43866_ARATH, Database accession No. Q43866 sequences.

Database- UniProt [Online], EBI: Glycine max (Soybean), Oct. 1, 2003, "Beta-fructofuranosidase (EC 3.2.1.26)," XP002419647, retrieved from EBI accession No. UNIPROT; Q7XA49_SOYBN, Database accession No. Q7XA49 sequences.

* cited by examiner

```
CcInv2  --------------------------------------------------------MINA 4
TIV1VI  -----MATQ---CYDPENSASRYTLLPDQPDSGHR--KSLKIISGIFLSVFLLLSVAFFP 50
STVInv  -----MATQYHSSYDPENSASHYTFLPDQPDSGHR--KSLKIISGIFLSSFLLLSVAFFP 53
DCVInv  MEHPITISHYTPLPDGEHSPSLTTTNTAEQSSRRRSLTFVLLFSSILAACLVMGTMVLFP 60
inv2    ------------------------------------------------------------ 0

CcInv2  NLNKSSPSSP--VSPHSLIPASRGVPQGVSEKTFR--GVSDANDV-YPWTNAMLSWQRTS 59
TIV1VI  ILNNQSPDLQ--IDSRSPAPPSRGVSQGVSDKTFR--DVAGASHVSYAWSNAMLSWQRTA 106
STVInv  ILNNQSPDLQ--SNSRSPAPPSRGVSQGVSDKTFR--DVVNASHISYAWSNAMLSWQRTA 109
DCVInv  NSGNEAVEKSTVVPEETVEVAPRGVAEGVSMKSFRRPALNAEPPANFPWNSNVLSWQRSS 120
inv2    ------------------------------------------------------------ 0

CcInv2  YHFQPEKNWMNDPNGPLFHMGWYHLFYQYNPDSAIWGN-ITWGHAVSRDLIHWLYLPFAM 118
TIV1VI  YHFQPQKNWMNDPNGPLYHKGWYHLFYQYNPDSAIWGN-ITWGHAVSKDLIHWLYLPFAM 165
STVInv  YHFQPQKNWMNDPNGPLYHKGWYHLFYQYNPDSAIWGN-ITWGHAVSKDLIHWLYLPFAM 168
DCVInv  FHFQPNQNWMNDPNGPLFYKGWYHLFYQYNPDGAIWGNKIVWGHAVSSDLIHWKHLPVAM 180
inv2    ---------------------------------AVWGN-IVWGHAVSRDLIHWLYLPFAM 26

CcInv2  VPDRPFDINGVWTGSATILPGGQIVILYTGDTADLVQVQNLAYPANLSDPLLLDWIKYPG 178
TIV1VI  VPDQWYDINGVWTGSATILPDGQIMMLYTGDTDDYVQVQNLAYPANLSDPLLLDWVKFKG 225
STVInv  VPDQWYDINGVWTGSATILPDGQIMMLYTGDTDDYVQVQNLAYPTNLSDPLLLDWVKYKG 228
DCVInv  VIDHWYDVNGVWTGSATILPDGQIVMLYTGSTNESVQVQNLAYPADPSDPLLIEWVKYPG 240
inv2    VPDRPFDVNGVWTGSATILPGGKIVMLYTGDTDDLVQVQNLAYPANLSDPLLLDWIKYPG 86

CcInv2  NPVMIPPPGIGKKDFRDPTTAWLAPDGTKWLVTLGSKVNKTGIALVYETSDFKGYRLLDG 238
TIV1VI  NPVLVPPPGIGVKDFRDPTTAWTGPQNGQWLLTIGSKIGKTGVALVYETSNFTSFKLLDG 285
STVInv  NPVLVPPPGIGVKDFRDPTTAWTGPQNGQWLLTIGSKIGKTGIALVYETSNFTSFKLLGE 288
DCVInv  NPVLVPPPGIDFKDFRDPTTAWRTPE-GKWRLIIGSKLNKTGISLVYDTVDFKNFTLLDG 299
inv2    NPVMIPPPGIGKKDFRDPTTAWLAPDGTKWLVTLGSKINKTGIAMVYETSDFKGYRLLDG 146

CcInv2  VLHAVPRTGMWECVDFYPVSTTGDNGLDTSANGPGTKHVLKASLDENKHDYYALGTYDPK 298
TIV1VI  VLHAVPGTGMWECVDFYPVSTKKTNGLDTSYNGPGVKHVLKASLDDNKQDHYAIGTYDLG 345
STVInv  VLHAVPGTGMWECVDFYPVSTEKTNGLDTSYNGPGVKHVLKASLDDNKQDHYAIGTYDLT 348
DCVInv  VLHAVHGTGMWECVDFYPVSKFGENGLDTSFDGVGVKHVMKASLDDDRNDYYAIGTYDPV 359
inv2    VLHAVPHTGMWECPD                                              161

CcInv2  NNKWTPDDPELDVGIGLRLDYGKYYASKTFYDQNKKRRILWGWIGETDSEAADLMKGWAS 358
TIV1VI  KNKWTPDNPELDCGIGLRLDYGKYYASKTFYDPKKERRVLWGWIGETDSESADLQKGWAS 405
STVInv  KNKWTPDNPELDCGIGLKLDYGKYYASKTFYDPKKQRRVLWGWIGETDSESADLQKGWAS 408
DCVInv  SGKWVPDNPELDVGIGLRYDYGIYYASKTFYDSNKKRRVLWSWIKETDSEISDVRKGWAS 419
inv2                                                                 161

CcInv2  VQTIPRTVVFDKKTGTNILQWPVEEAESLRFNATEFDTVKLEPGSIAPLNIGSATQLDII 418
TIV1VI  VQSIPRTVLYDKKTGTHLLQWPVEEIESLRVGDPTVKQVDLQPGSIELLRVDSAAELDIE 465
STVInv  VQSIPRTVLYDKKTGTHLLQWPVEEIESLRAGDPIVKQVNLQPGSIELLHVDSAAELDIE 468
DCVInv  VQGIPRTILFDPKTGSNLLQWPVEEVNKLRLNKTVFENVEINTGAVLPLEIGSGSQLDIT 479
inv2                                                                 161

CcInv2  ASFEVDSEALEATVEAD-VGYNCTTSGGAASRGKLGPFGLLVLADGSLSELTPVYFYISK 477
TIV1VI  ASFEVDKVALQGIIEADHVGFSCSTSGGAASRGILGPFGVIMIADQTLSELTPVYFYISK 525
STVInv  ASFEVDKVALQGIIEADHVGFSCSTSGGAASRGILGPFGVVMIADQTLSELTPVYFFISK 528
DCVInv  AEFEVDKESLERVQETNEV-YDCKNNGGSSGRGALGPFGLLILADKDLSEQTPVYFYIAK 538
inv2                                                                 161

CcInv2  STDGSAETHFCSDESRSSKAPDVGKLVYGSTVPVLDGEKLSARLLVDHSVVESFAQGGRR 537
TIV1VI  GADGRAETHFCADQTRSSEAPGVGKQVYGSSVPVLDGEKHSMRLLVDHSIVESFAQGGRT 585
STVInv  GADGRAETHFCADQTRSSEAPGVAKQVYGSSVPVLDGEKHSMRLLVDHSIVESFAQGGRT 588
DCVInv  GSGGNLRTFFCADHSRSSKAVDVDKEIYGSVVPVLRGEKLTMRILVDHSIVESFSQGGRT 598
inv2                                                                 161

CcInv2  VITSRVYPTKAIYGAARLFLFNNATGVSVTASAKIWHMRSADIRT-FPDL.          587
TIV1VI  VITSRIYPTKAVNGAARLFVFNNATGASVTASVKIWSLESANIQS-FPLQDL         636
STVInv  VITSRIYPTKAVNGAARLFVFNNATGASVTASVKIWSLESANIRS-FPLQDL         639
DCVInv  CITSRVYPTKAIYNNAKVFLFNNATEARIIASLNIWQMNTAQRQTHFADLVI         650
inv2                                                                 161
```

FIG. 2

```
CaInv3    -MECVRE-YQLRNVSSHCSISEMDDYD-LSKLLDKPDKPR-LNIERQRSFDERSLSELSI  56
LJNInv1   -MDGP---VGLKKISSQCSIPEMDDFDQLSRLLD---KPR-LNIERQRSFDERSLSELSQ  52
AtINInv   MEEGHKEPLVLRVEGSHCSLSEMDDFD-LTRALE---KPRQLKIERKRSFDERSMSELST  56

CaInv3    GLSRA-LDAYETAYSPG-RSALDTPVSSARNSFEPHPMVADAWEALRRSLVFFRDQPVGT  114
LJNInv1   GFARAGVDNYEN-YSPGVRSGFNTPASSARNSFEPHPMVADAWESLRRSLVYFKGQPVGT  111
AtINInv   GYVRQ-DSILEMAHSPGSRSMVDTPLS-VRNSFEPHPMVAEAWEALRRSMVFFRGQPVGT  114

CaInv3    IAAYDHASEEVLNYDQVFVRDFVPSALAFLMNGEPEIVKNFLLKTLQLQGWEKRIDRFKL  174
LJNInv1   IAAVDHQAEEVLNYDQVFVRDFVPSALAFLMNGEPDIVRNFLLKTLHLQGWEKRIDRFKL  171
AtINInv   IAAYDHASEEVLNYDQVFVRDFVPSALAFLMNGEPDIVKNFLLKTLQLQGWEKRVDRFKL  174

CaInv3    GEGAMPASFKVLHDPDRKTDTIVADFGESAIGRVAPVDSGFWWIILLRAYTKSTGDLSLA  234
LJNInv1   GEGVMPASFKVLHDPVRKTDTLIADFGESAIGRVAPVDSGFWWIILLRAYTKSTGDLTLA  231
AtINInv   GEGVMPASFKVLHDPVRKTDTIIADFGESAIGRVAPVDSGFWWIILLRAYTKSTGDLTLS  234

CaInv3    ETPECQKGMRLILSLCLSEGFDTFPTLLCADGCSMIDRRMGIYGYPIEIQALFFMALRCA  294
LJNInv1   ESPDCQKGMKLILTLCLSEGFDTFPTLLCADGCSMIDRRMGIYGYPIEIQALFFMALRCA  291
AtINInv   ETPECQRGMRLILSLCLSEGFDTFPTLLCADGCSMVDRRMGVYGYPIEIQALFFMALRCA  294

CaInv3    LVMLR-HDTEGKEFIERIVKRLHALSFHMRSYFWLDFQQLNDIYRYKTEEYSHTAVNKFN  353
LJNInv1   LSMLKQDDAEGKECVERIVKRLHALSYHMRGYFWLDFQQLNDIYRYKTEEYSHTAVNKFN  351
AtINInv   LSMLK-PDEEGRDFIERIVKRLHALSFHMRSYFWLDFQQLNDIYRYKTEEYSHTAVNKFN  353

CaInv3    VIPDSILDWVFDFMPTRGGYFIGNVSPARMDMRWFALGNCVAILSCLATAEQAAAIMDLI  413
LJNInv1   VIPDSIPEWVFDFMPTRGGYFIGNVSPARMDFRWFALGNCVAILSSLATPEQSMAIMDLI  411
AtINInv   VMPDSIPDWVFDFMPLRGGYFVGNVSPARMDFRWFSLGNCVSILSSLATPDQSMAIMDLL  413

CaInv3    EARWDELVGEMPMKICYPAIESHEWRIVTGCDPKNTRWSYHNGGSWPVLLWLLTAACIKT  473
LJNInv1   EARWDELVGEMPLKISYPAIESHEWRIVTGCDPKNTRWSYHNGGSWPVLLWLVTAACIKT  471
AtINInv   EHRWEELVGEMPLKICYPCIESHEWRIVTGCDPKNTRWSYHNGGSWPVLLWTLTAACIKT  473

CaInv3    GRIQIARRAIDLAESLLLKDSWPEYYDGKLGRYIGKQARKFQTWSIAGYLVAKMMLEDPS  533
LJNInv1   GRPQIARRAIELAESRLLKDGWPEYYDGKLGRYVGKQARKYQTWSIAGYLVAKMMLEDPS  531
AtINInv   GRPQIARRAIDLIESRLHRDCWPEYYDGKQGRYVGKQARKYQTWSIAGYLVAKMMLEDPS  533

CaInv3    HLGMISLEEDKQMKPLIKILLVDLL                                    558
LJNInv1   HLGMISLEEDKQMKPVIKRSSSWTC                                    556
AtINInv   HIGMISLEEDKQMKPVIKRSASWTC                                    558
```

FIG. 3

```
CcINV4     IDHSIIESFGGEGKTCITSRVYPTLAIGQESHLYVFNYGTESIRISNLSA 50
TIV1VI-2   VDHSIVESFAQGGRTVITSRIYPTKAVNGAARLFVFNNATGASVTASVKI 50
LIN6-2     IDNSIVESFGAGGKTCITSRVYPTLAIFDKAHLFAFNNGAETITIETLNA 50

CcINV4     WSMRRAQFFQSSTKEEKPKLIEE                            73
TIV1VI-2   WSLESANIQSFPLQDL                                   66
LIN6-2     WSMANAKLH                                          59
```

FIG. 4

```
CcINV1   ----MAS-------FYLWLMCLCWMVVLGHG-ILLEAEASHGVYRNLASL-QPASPSQTYRTSYHFQPPK  56
LIN5CWI  MELFMKN-----SSLWGLKFYLFCLFIILSNI--NRAFASHNIFLDLQSS-SAISVKNVHRTRFHFQPPK  62
LIN6CWI  MEILRKS-----SSLWALPILVLCFFINNG----VFVDASHKVYMHLQSTTSHVDASKVHRTGYHFQPPK  61
DCCWInv  MGVTIRNRNYDHGSLPFLQSLLAILLVTTTTLHINGVEAFHEIHYNLQSV-GAENVKQVHRTGYHFQPKQ  69
inv1     ----------------------------------------------------------------------  0

CcINV1   NWMNDPNGPTVYRGLYHLFYQYNPLGPDWGNIVWAHSTSKDLINWNPHKAAIFPSQKGDVNGCWSGSTTM  126
LIN5CWI  HWINDPNAPMYYNGVYHLFYQYNPKGSVWGNIIWAHSVSKDLINWIHLEPAIYPSKKFDKYGTWSGSSTI  132
LIN6CWI  NWINDPNGPMYYNGVYHLFYQYNPKGATWGNIVWAHSVSKDLINWIPLEPAIYPSKVFDKYGTWSGSATI  131
DCCWInv  NWINDPNGPMYYKGVYHLFYQYNPKGAVWGNIVWAHSVSTDLINWIPLEPAIFPSKPFDKYGCWSGSATI  139
inv1     -------------------------GRLWGNIVWAHSTSKDLINWNPHKAAIFPSQKGDVNGCWSGSTTM  45

CcINV1   LRGENPAILYTGIDPK---SQQVQNLAVPRNLSDPYLIEWVKSPYNPLMTPTPENKIDSSSFRDPTTAWL  193
LIN5CWI  LPNNKPVIIYTGVVDS--YNNQVQNYAIPANLSDPFLRKWIKPNNNPLIVP--DNSINRTEFRDPTTAWM  198
LIN6CWI  LPGNKPVILYTGIVDA--NKTQVQNYAIPANMSDPYLRKWIKPDNNPLIVA--DKNINKIQFRDPTTAWM  197
DCCWInv  LPGNKPVILYTGIVEGPPKNVQVQNYAIPANLSDPYLRKWIKPDNNPLVVA--NNGENATAFRDPTTAWL  207
inv1     LRGENPAILYTGIDPK---NQQVQNLAVPRNLSDPYLIEWVKSPYNPLMTPTPENKINSSSFRDPTTAWL  112

CcINV1   GPDGRWRVIVGNKLNRRGKALLYRS-KDFVRWTKAQHPLYSIQGTGMWECPDFYPVSS-SPIGLDTSTIG  261
LIN5CWI  GQDGLWRILIASMRKHRGMALLYRS-RDFMKWIKAQHPLHSSTNTGNWECPDFFPVLFNSTNGLDVSYRG  267
LIN6CWI  GRDGYWRVLVGSVRNHRGKVIMYKSNKNFMKWTKAKHPLHSAQGTGNWECPDFFPVSLKNENGLDTSYDG  267
DCCWInv  DKSGHWKMLVGSKRNRRGIAYLYRS-KDFIKWTKAKHPIHSQANTGMWECPDFFPVSLKGLNGLDTSVTG  276
inv1     GPDGRWRVIVGNKLNRRGKALLYRS-KDFVRWTKAQHPLYSIQGTGMWECPD                    163

CcINV1   EGVKHVLKVSLDDTKHDQYAIGTYVHSKDVFVPNAGAAEKFSGLRYDYGKSYASKTFYDSLKKRRILWGW  331
LIN5CWI  KNVKYVLKNSLDVARFDYYTIGMYHTKIDRYIPNNNPIDGWKGLRIDYGNFYASKTFYDPSRNRRVIWGW  337
LIN6CWI  KDVKHVLKVSFDVTRFDHYTVGTYDTKKDKYFPDNTSIDGWKGLRLDYGNYYASKTFFDSGKNRRILLGW  337
DCCWInv  ESVKHVLKVSLDLTRYEYYTVGTYLTDKDRYIPDNTSVDGWAGLRYDYGNFYASKTFFDPSKNRRILWGW  346
inv1                                                                             163

CcINV1   INESLSR-EDYIAQGWSGVQAIPRLVWLDKSGKQLVQWPISEIETLRQKKVGYPLTL-LKSGSTLEVQGI  399
LIN5CWI  SNESDVLPDDEIKKGWAGIQGIPRQVRLNLSGKQLLQWPIEELETLRKQKVQLNNKR-LSKGEMFEVKGI  406
LIN6CWI  ANESDTV-DNDVKKGWAGVHPIPRKIWLDPSGKQLVQWPVQELETLRKKKVQLNNKK-LNKGEKVEIKGI  405
DCCWInv  ANESDST-AHDVAKGWAGIQLIPRTLWLDPSGKQLMQWPIEELETLRGSKVKFSRKQDLSKGILVEVKGI  415
inv1                                                                             163

CcINV1   KAAQADVDVSFQVAPQLEQADALDPSWTDP--QLLCSQKGASVRGGTGPFGLKVLASKDLQEYTAVFFRI  467
LIN5CWI  SASQADVEVLFSFSS-LNEAEQFDPRWADLYAQDVCAIKGPTIQGGLGPFGLVTLASKNLEEYTPVFFRV  475
LIN6CWI  TVAQADVEVIFSFAS-LDKAEPFDSSWADLYAQDVCAIKGSTVQGGLGPFGLLTLASKNLEEYTPVFFRV  474
DCCWInv  TAAQADVEVTFSFKS-LAKREPFDPKWLEYDAEKICSLKGSTVQGGVGPFGLLTLASEKLEEYTPVFFRV  484
inv1                                                                             163

CcINV1   FKARNKYVVLMCSDQSRSSLNEK--PDKTTYGAFLDVDPLH-EELSLRSLIDHSIVESFGGKGKACITSR  534
LIN5CWI  FKAQKSYKILMCSDARRSSMRQNEAMYKPSFAGYVDVDLEDMKKLSLRSLIDNSVVESFGAGGKTCITSR  545
LIN6CWI  FKAHDNYKVLMCSDASRSSLKNETTMYKPSFAGYVDVDLAD-KKLSLRSLIDNSIVESFGAGGKTCITSR  543
DCCWInv  FKVQNTHKVLMCSDATRSSLKEG--LYRPSFAGFVDVDLATDKKISLRSLIDNSVVESFGAKGKTCISSR  552
inv1                                                                             163

CcINV1   VYPTKALGNEARLYVFNYGKANVAISSMNAWTMKN-ASINRKN                             576
LIN5CWI  VYPTLAIYDNAHLFVFNNGSETITIETLNAWGMDA-CKMN                                584
LIN6CWI  VYPTLAIFDKAHLFAFNNGAETITIETLNAWSMAN-AKLH                                582
DCCWInv  VYPTLAVYENAHLYVFNNGSETITVENLDAWSMKKPLRMN                                592
inv1                                                                             163
```

FIG. 5

```
CcInvI1  MRN----FTSFMLLFPYALVVLTIV--PPLISCDLISETCDQTP------NDRLCVKILR  48
CcInvI2  MRP----SISSALLITL---FLLCFIHGATSQENLIRDSCRTFAKDDPNINFNFCTTSLQ  53
CcInvI3  MAS-----FGRFCLFAW----LLWGNLGVRGDDSAIVGVCKKIG-----IYYYMCYDCLK  46
CcInvI4  MELSWSHRSSYFPLLLFFLAFLGYYSSCGEATQDLIERVCSKSK------DPSFCTKALE  54
ZmInvI   MK-----LLQALCPLVI---LLAC----STSNASVLQDACKSFAAKIPDTGYAYCIKFFQ  48
NtInvI   MRN----LFPIFMLITN----LAFN--DNNNSNNIINTTCRATT------NYPLCLTTLH  44

CcInvI1  KDNRS---LDADVAGLALVAVEAVRDKANSTLQSIKELKRS---NLTLANALMECQENYY  102
CcInvI2  AAPAS---HCAALRGLGTISFRLIRYNVTDTRCMIRQLLKGKKLDPYVRQCLNDCFELYS  110
CcInvI3  SNPQE-----PDFAAKSIICATDAYVIIRKSAFDFSLNSTG-----RFREVAKLCVDQFD  96
CcInvI4  SDPRS---RTANLAGLCQISIDLSTTNAKSTQALVTSLGKKAT-DKISKEIYNTCLENYT  110
ZmInvI   ADRGS---AGADKRGLAAIAVRIMGAAAKSTASHIAALRASEK-DKERLACLSDCSEVYA  104
NtInvI   SDPRTSEAEGADLTTLGLVMVDAVKLKSIEIMKSIKKLEKS---NPELRLPLSQCYIVYY  101

CcInvI1  VILRIDVPKAVGSMRE-NPR-LAEHGMADAVIEAQG--CEASLN--KLEQSP-LADVNAA  155
CcInvI2  DAIDT-MKQAMK--AYNTKR-FADANIEISSIMDAATTCEDGFNERKGVLSP-LTKRNNN  165
CcInvI3  ITLGY-CKAAFKAWRLKR-KLATLAFLHSG--LDYYFKCVDHLSEP-IPNEYGIQLDTAK  151
CcInvI4  NSISV-LGDCTKRLQAGD---YAGVNIKASAAQTEVDTCDECFKERKLPEPPTLTNACQK  166
ZmInvI   QAVDQ-TGVAAKGIASGTPRGRADAVMALSTVEDAPGTCEQGFQDLS-VRSP-LASEDAG  161
NtInvI   AVLHADVTVAVEALKRGVPK-FAENGMVDVAVEAET--CEFSFKY-NGLVSP-VSDMNKE  156

CcInvI1  VYDLSVVALSIIRIMLHRIYTVN                                       178
CcInvI2  TFELSAIALNVMRILQTRSD                                          185
CcInvI3  SFNEVSIKVASLP                                                 164
CcInvI4  EQKLCNIILVTANMLQGN                                            184
ZmInvI   FRKDASIALSVTAAL                                               176
NtInvI   IIELSSVAKSIIRMLL                                              172
```

FIG. 6

NUCLEIC ACIDS AND PROTEINS ASSOCIATED WITH SUCROSE DEGRADATION IN COFFEE

This is a U.S. National Phase of International Application No. PCT/US2006/37600, filed Sep. 27, 2006, which claims benefit of U.S. Provisional Application No. 60/720,865, filed Sep. 27, 2005, the entire contents of each of which are incorporated by reference herein.

FIELD OF ME INVENTION

The present invention relates to the field of agricultural biotechnology. More particularly, the invention relates to enzymes participating in sucrose metabolism in plants, coffee in particular, and the genes and nucleic acid sequences that encodes these enzymes, along with regulatory mechanisms that regulate the sucrose metabolism via these enzymes.

BACKGROUND OF THE INVENTION

Various publications, including patents, published applications and scholarly articles, cited throughout the present specification are incorporated by reference herein, in its entirety. Citations not fully set forth within the specification may be found at the end of the specification.

Sucrose plays an important role in the ultimate aroma and flavor that is delivered by a coffee grain or bean. Sucrose is a major contributor to the total free reducing sugars in coffee, and reducing sugars are important flavor precursors in coffee. During the roasting of coffee grain, reducing sugars will react with amino group containing molecules in a Maillard type reaction, which generates a significant number of products with caramel, sweet and burnt-type aromas and dark colors that are typically associated with coffee flavor (Russwurm, 1969; Holscher and Steinhart, 1995; Badoud, 2000). The highest quality *Arabica* grain (*Coffea Arabica*) have been found to have appreciably higher levels of sucrose (between 7.3 and 11.4%) than the lowest quality *Robusta* grain (*Coffea canephora*) (between 4 and 5%) (Russwurm, 1969; Illy and Viani, 1995; Chahan et al., 2002; Badoud, 2000). Despite being significantly degraded during roasting, sucrose still remains in the roasted grain at concentrations of 0.4-2.8% dry weight (DW); thereby, contributing directly to coffee sweetness. A clear correlation exists between the level of sucrose in the grain and coffee flavor. Therefore, identifying and isolating the major enzymes responsible for sucrose metabolism and the underlying genetic basis for variations in sucrose metabolism will enable advances in the art of improving coffee quality.

Currently, there are no published reports on the genes or enzymes involved in sucrose metabolism in coffee. However, sucrose metabolism has been studied in tomato *Lycopersicon esculentum* (a close relative of coffee, both are members of asterid I class), especially during tomato fruit development. An overview of the enzymes directly involved in sucrose metabolism in tomato is shown in FIG. 1 (Nguyen-Quoc et al., 2001). The key reactions in this pathway are (1) the continuous rapid degradation of sucrose in the cytosol by sucrose synthase (SuSy) and cytoplasmic invertase (I), (2) sucrose synthesis by SuSy or sucrose-phosphate synthase (SPS), (3) sucrose hydrolysis in the vacuole or in the apoplast (region external to the plasma membrane, including cell walls, xylem vessels, etc) by acid invertase (vacuolar or cell wall bound) and, (4) the rapid synthesis and breakdown of starch in the amyloplast.

As in other sink organs, the pattern of sucrose unloading is not constant during tomato fruit development. At the early stages of fruit development, sucrose is unloaded intact from the phloem by the symplast pathway (direct connections between cells) and is not degraded to its composite hexoses during unloading. Both the expression and enzyme activity of SuSy are highest at this stage and are directly correlated with sucrose unloading capacity from the phloem (phenomena also called sink strength; Sun, et al., 1992; Zrenner et al., 1995). Later in fruit development, the symplastic connections are lost. Under these conditions of unloading, sucrose is rapidly hydrolyzed outside the fruit cells by the cell wall bound invertase and then the glucose and fructose products are imported into the cells by hexose transporters. Sucrose is subsequently synthesized de novo in the cytoplasm by SuSy or SPS (FIG. 1). SPS catalyses an essentially irreversible reaction in vivo due to its close association with the enzyme sucrose phosphate phosphatase (Echeverria et al., 1997). In parallel to the loss of the symplastic connections, SuSy activity decreases, and eventually becomes undetectable in fruit at the onset of ripening (Robinson et al. 1998; Wang et al. 1993). Therefore, late in the development of tomato fruit, the SPS enzyme, in association with SP, appears as the major enzymes for sucrose synthesis.

Plant invertases have been separated into two groups based on the optimum pH for activity. Invertases of the first group are identified as neutral invertases, which are characterized as having a pH optima in the range of 7-8.5. The neutral invertases have been found to be located in the cytosol of plant cells. Invertases of the second group are identified as acid invertases, which are characterized as having a pH optima for activity between pH 4.5 and 5.5. The acid invertase have been shown to exist in both soluble and insoluble forms (Sturm and Chrispeels, 1990). Insoluble acid invertase is irreversibly and covalently associated with the cell wall; whereas, soluble acid invertase is located in both the vacuole and apoplast.

Research over the past decade has shown that vacuolar as well as cell-wall bound invertase are key enzymes in the regulation of sucrose metabolism during fruit development of various species. Red-fruit species of tomato, such as the commercial species *Lycopersicon esculent* and the wild species *L. pimpinellifolium*, for example, do not store high levels of sucrose but, instead, accumulate hexoses in the form of glucose and fructose. Evidence from crosses of red-fruit species with sucrose-accumulating green-fruit species (Yelle et al., 1991) has shown the crucial role of acid invertase in preventing final sucrose accumulation in red-fruited tomato species. Genetic analysis studies have located the locus conferring high levels of soluble solids in *L. pimpinellifolium* fruit to the known position of vacuolar invertase TIV1 (Tanksley et al., 1996; Grandillo and Tanksley, 1996). A similar conclusion was reached from the analysis of expression of an antisense TIV1 cDNA construction in transgenic tomatoes (Klann et al, 1993; Klann et al., 1996). Thus the vacuolar form of invertase is considered to play a major role in both the regulation of hexose levels in mature fruits and in the regulation of mobilization of sucrose stored in the vacuoles (Klann et al., 1993; Yau and Simon, 2003). The cell wall bound isoforms are believed to be involved in phloem unloading and sucrose partitioning (Scholes et al, 1996).

The importance of cell wall bound invertase has been demonstrated by studies with transgenic tomato (Dickinson et al., 1991) and tobacco (von Schaewen et al., 1990) plants that overexpress cell wall invertase in a constitutive fashion. Elevated levels of invertase activity in such plants caused reduced levels of sucrose transport between sink and source tissues, which lead to stunted growth and overall altered plant morphology. Reduction of extracellular invertase activity has also been shown to have dramatic effects on plant and seed development in various species. Analysis of transgenic carrots with reduced levels of cell wall invertase due to the constitutive expression of an antisense cell wall invertase construct (Tang et al., 1999) has shown dramatic consequences on early plant development as well as on tap root formation during early elongation phase.

Studies of the miniature-1 (mn1) (Lowe and Nelson, 1946) seed mutant in maize, which is characterized by an aberrant pedicel and a drastic reduction in the size of the endosperm, have shown that Mn1 seed locus encodes a cell wall invertase, CWI-2 (Miller and Chourey, 1992; Cheng et al.; 1996). Interestingly, in the mn1 mutant, global acid invertase (vacuolar and cell wall bound) activity is dramatically reduced suggesting coordinate control of both the vacuolar and cell wall enzyme activities.

Because of the importance of sucrose for high quality coffee flavor, a need exists to determine the metabolism of sucrose beans and the interaction of genes involved in that metabolism. There is also a need to identify and isolate the genes that encode these enzymes in coffee, thereby providing genetic and biochemical tools for modifying sucrose production in coffee beans to manipulate the flavor and aroma of the coffee.

SUMMARY OF THE INVENTION

One aspect of the present invention features a nucleic acid molecule isolated from coffee (*Coffea* spp.) comprising a coding sequence that encodes an invertase or an invertase inhibitor. In one embodiment, the coding sequence encodes an invertase, which may be a cell wall invertase, a vacuolar invertase or a neutral invertase. In specific embodiments, the cell wall invertase comprises a conserved domain having amino acid sequence WECPDF (SEQ ID NO:28). In various embodiments, the invertase comprises an amino acid sequence greater than 55% identical to SEQ ID NO:9 or SEQ ID NO:13, and preferably comprises SEQ ID NO:9 or SEQ ID NO:13. In exemplary embodiments, the nucleic acid molecule comprises SEQ ID NO:1 or SEQ ID NO:4, In another embodiment, the invertase is a vacuolar invertase and comprises a conserved domain having amino acid sequence WECVDF (SEQ ID NO:78 wherein Xaa is Val). The vacuolar invertase may comprise an amino acid sequence 70% or more identical to SEQ ID NO:10, and preferably comprises SEQ ID NO:10. In an exemplary embodiment, the nucleic acid molecule encoding the vacuolar invertase comprises SEQ ID NO:2.

In another embodiment, the invertase is a neutral invertase, which may comprise an amino acid sequence 84% or more identical to SEQ ID NO:11, and preferably comprises SEQ ID NO:11. In an exemplary embodiment, the nucleic acid molecule encoding the neutral invertase comprises SEQ ID NO:3.

In other embodiments the coding sequence encodes an invertase inhibitor. In certain embodiments, the invertase inhibitor comprises four conserved cysteine residues in its amino acid sequence. The invertase inhibitor may comprise an amino acid sequence that is 25% or more identical to any one of SEQ ID NOS: 13, 14, 15 or 16, and preferably comprises any one of SEQ ID NOS: 13, 14, 15 or 16. In exemplary embodiments, the nucleic acid molecule encoding the invertase inhibitor comprises any one of SEQ ID NOS: 5, 6, 7 or 8.

In certain embodiments, the above-described coding sequence is an open reading frame of a gene. In other embodiments, it is an mRNA molecule produced by transcription of that gene, or a cDNA molecule produced by reverse transcription of the mRNA molecule of claim. Another embodiment is directed to an oligonucleotide between 8 and 100 bases in length, which is complementary to a segment of the foregoing nucleic acid molecule.

Another aspect of the invention features a vector comprising the coding sequence of the invertase or invertase inhibitor encoding nucleic acid molecules described above. In certain embodiments, the vector is an expression vector selected from the group of vectors consisting of plasmid, phagemid, cosmid, baculovirus, bacmid, bacterial, yeast and viral vectors. Various embodiments comprise vectors in which the coding sequence of the nucleic acid molecule is operably linked to a constitutive promoter, or to an inducible promoter, or to a tissue specific promoter, preferably a seed specific promoter in the latter embodiment.

Host cells transformed with any of the above described vectors are also provided in another aspect of the invention. The host cells may be plant cells, bacterial cells, fungal cells, insect cells or mammalian cells. A fertile produced from a transformed plant cell of the invention is also provided.

Another aspect of the invention features a method of modulating flavor or aroma of coffee beans, comprising modulating production or activity of one or more invertase or invertase inhibitor within coffee seeds. In certain embodiments, the method comprises increasing production or activity of the one or more invertase or invertase inhibitors. In certain embodiments, this is accomplished by increasing expression of one or more endogenous invertase or invertase inhibitor genes within the coffee seeds. Other embodiments comprise introducing an invertase- or invertase inhibitor-encoding transgene into the plant.

In a particular embodiment, the method comprises increasing production or activity of one or more invertase inhibitors. In this embodiment, endogenous invertase activity in the plant may be decreased as compared with an equivalent plant in which production or activity of the invertase inhibitor is not increased. Further, the plant may contain more sucrose in its seeds than does an equivalent plant in which production or activity of the invertase inhibitor is not increased.

In other embodiments, the method comprises decreasing production or activity of the one or more invertase or invertase inhibitors. This may be accomplished by introducing a nucleic acid molecule into the coffee that inhibits the expression of one or more of the invertase- or invertase inhibitor-encoding genes. In a particular embodiment, the expression or activity of an invertase is decreased. In this embodiment, the plant may contain more sucrose in its seeds than does an equivalent plant in which production or activity of the invertase is not decreased.

Other features and advantages of the invention will be understood by reference to the drawings, detailed description and examples that follow.

BRIEF DESCRIPTION OF THE DRAWINGS

FIG. 2. Protein sequence alignment of CcInv2 with vacuolar acid invertase proteins. Protein sequences were selected based on BLASTp homology search using CcInv2 (Coffea canephora Invertase 2, SEQ ID NO:10). GenBank accession numbers are P29000 for acid invertase from tomato TIV1 (*Lycopersicon esculentum*) (SEQ ID NO.:17), CAA47636.1 for acid invertase from carrot (*Daucus carota*) (SEQ ID NO.: 18), AAQ17074 for acid invertase from potato (*Solanum tuberosum*) (SEQ ID NO.:19) and CAE01318 for inv2 from *Coffea arabica* (SEQ ID NO.:20). Amino acids that differ from that of CcInv2 sequence are colored in gray. The alignment was done using the Clustal W program in the MegAlign Software (Lasergene package, DNA STAR). The amino acid sequence NDPNG (SEQ ID NO:27) is a hallmark of plant acid invertases (βF-motif). The sequence WECVDF (SEQ ID NO:78, wherein Xaa is Val) is specific for vacuolar invertase.

FIG. 3. Protein sequence alignment of CaInv3 with vacuolar acid invertase proteins. Protein sequences were selected based on BLASTp homology search using CaInv3 (*Coffea arabica* Invertase 3, SEQ ID NO:11). GenBank accession numbers are NP_567347 for AT NInv (neutral cytoplasmic invertase from *A. thaliana*) (SEQ ID NO:21), and CAG30577 for LJNInv1 (neutral cytoplasmic invertase from *Lotus corniculatus* var. *japonicus*) (SEQ ID NO:22). Alignment was done using the Clustal W program in the MegAlign Software (Lasergene package, DNA STAR). Amino acids that differ from that of CaInv3 sequence are colored in gray.

FIG. 4. Partial protein sequence alignment of CcInv4 with TIV1 and LING acid invertase proteins. Partial protein alignment between CcInv4 (SEQ ID NO:12), TIV1 (vacuolar invertase) (SEQ ID NO:17) and LIN6 (cell wall bound invertase) (SEQ ID NO:23) was done using the Clustal W program in the MegAlign Software (Lasergene package, DNA STAR). GenBank accession numbers are P29000 for TIV1 and AAM28823 for LIN6 from tomato (*Lycopersicon esculentum*). Amino acids that differ from that of CcInv4 sequence are colored in gray.

FIG. 5. Protein sequence alignment of CcInv1 with cell-wall bound invertase proteins. Protein sequences were selected based on BLASTp homology search using CcInv1 (*Coffea canephora* Invertase 1, SEQ ID NO:9). GenBank accession numbers are CAB85897 for LIN5 (SEQ ID NO:24), AAM28823 for LIN6 from tomato (*Lycopersicon esculentum*) (SEQ ID NO:23), CAA49162.1 for DCCWInv invertase from carot (*Daucus carota*) (SEQ ID NO:25), and CAE01317 for inv1 from *Coffea arabica* (SEQ ID NO:26). Amino acids that differ from that of CcInv1 sequence are colored in gray. The alignment was done using the Clustal W program in the MegAlign Software (Lasergene package, DNA STAR). The amino acid sequence NDPNG (SEQ ID NO:27) is a hallmark of plant acid invertases (βF-motif). The sequence WECPDF (SEQ ID NO:28) is specific for periplasmic or cell wall-bound invertase.

FIG. 6. Protein sequence alignment of CcInvI with invertase inhibitors proteins. Alignment of CcInvI 1, 2, 3 and 4 proteins (SEQ ID NOS: 13, 14, 15 and 16, respectively) with ZM-InvI (CAC69335.1) from corn (*Zea mays*) (SEQ ID NO:29) and Nt InvI (AAT01640) from tobacco (*Nicotiana tabacum*) (SEQ ID NO:30). Amino acids identical to the consensus sequence are colored in gray. Four Conserved Cys residues are noted. The alignment was done using the Clustal W program in the MegAlign Software (Lasergene package, DNA STAR).

DETAILED DESCRIPTION OF ILLUSTRATIVE EMBODIMENTS

Definitions

Figure 1:
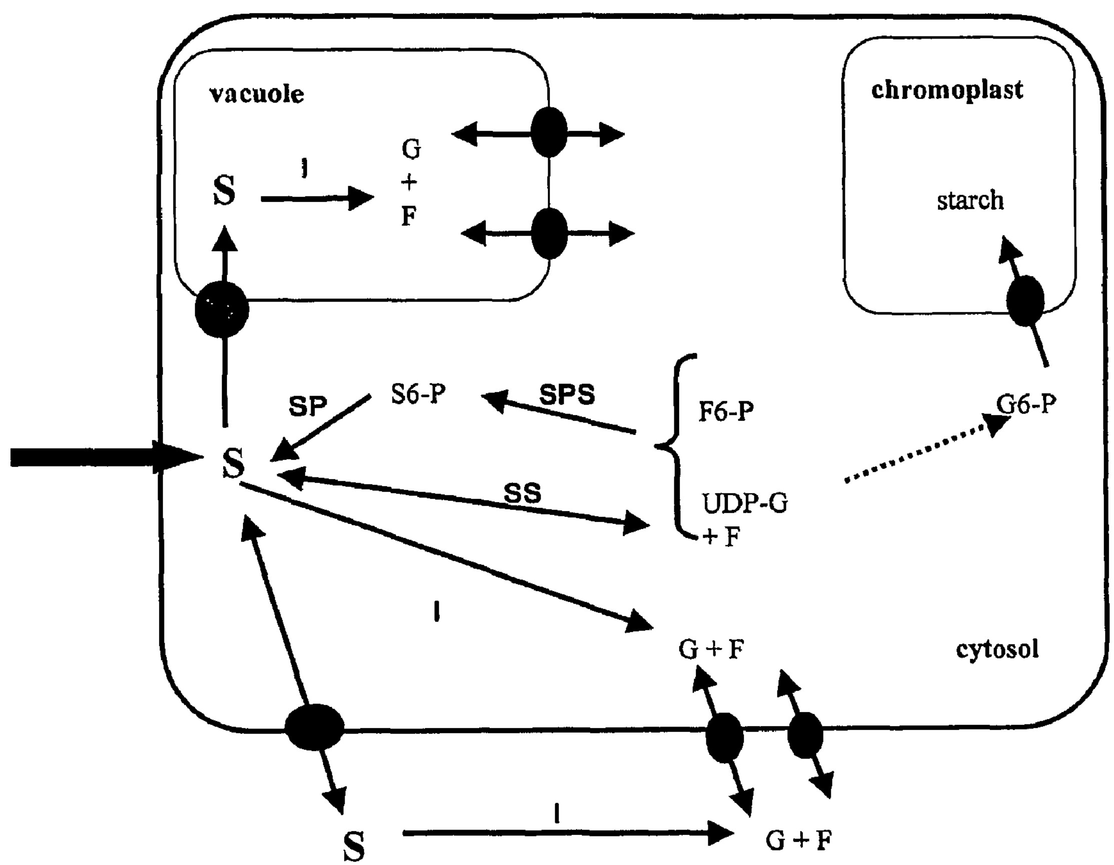
FIG. 1. Model for sucrose metabolism in tomato fruit. S (Sucrose) is imported from phloem by a symplastic pathway or is hydrolysed by cell-wall invertase. Glucose and fructose are imported into the cytosol by specific Sugar Transporter Proteins. In cytosol, sucrose is degraded by SS (sucrose synthase) and its re-synthesis is catalysed by SPS (sucrose phosphate synthase) associated with SP (sucrose phosphatase) or SS. Sucrose can be exported in vacuole and hydrolysed by vacuolar invertase. UDP-glucose after modifications can be used for starch synthesis in chromoplast. Abbreviations: G, glucose; F, fructose; F6-P, fructose 6-phosphate; UDP-G, UDP-glucose; G6-P, glucose 6-phosphate; S6-P, sucrose 6-phosphate; I, invertase; SP, sucrose phosphatase, SPP sucrose phosphate synthase.

Various terms relating to the biological molecules and other aspects of the present invention are used through the specification and claims. The terms are presumed to have their customary meaning in the field of molecular biology and biochemistry unless they are specifically defined otherwise herein.

The term "sucrose metabolizing enzyme" refers to enzymes in plants that primarily function to accumulate sucrose or degrade sucrose within the plant and include, for example, sucrose synthase (SuSy), sucrose phosphate synthase (SPS) and sucrose phosphatase (SP), as well as invertases (Inv) of various types, and invertase inhibitors (Inv I). Together, the different sucrose metabolizing enzymes operate to control the metabolism of sucrose as needed by the plant for either storage or for energy needs.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for Protein Modifications and Nonprotein Cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease SI), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

DESCRIPTION

Sucrose is a major contributor of free reducing sugars involved in the Maillard reaction that occurs during the roasting of coffee grain. Therefore, it is widely believed to be an important flavor precursor molecule in the green coffee grain. Consistent with this idea, the highest quality *Arabica* grains have appreciably higher levels of sucrose (between 7.3 and 11.4%) than the lowest quality *Robusta* grains (between 4 and 5%). Also, sucrose, while being significantly degraded during roasting, can remain in the roasted grain at concentrations of 0.4-2.8% dry weight (DW) and so participates directly in coffee's sweetness. Because of the clear correlation between the level of sucrose in the grain and coffee flavor, the ability to understand and manipulate the underlying genetic basis for variations in sucrose metabolism and carbon partitioning in coffee grain is important.

Key enzymes involved in sucrose metabolism have been characterized in model organisms (e.g., tomato, potato, *Arabidopsis*). In accordance with the present invention, protein sequences of these enzymes have been used to perform similarity searches in *Coffea canephora* and *C. Arabica* cDNA libraries and EST databases using the tBLASTn algorithm, as described in greater detail in the examples. Full-length cDNAs encoding CcInv1 (cell wall bound invertase), CcInv2 (vacuolar invertase) and CaInv3 (cytoplasmic invertase) were isolated. A partial cDNA sequence (CcInv4) was also isolated, and is believed to represent a cell wall bound invertase). In addition, four full-length cDNA sequences encoding likely invertase inhibitors CcInvI1, CcInvI2, CcInvI3 and CcInvI4 have been identified and characterized.

One aspect of the present invention relates to nucleic acid molecules from coffee that encode a variety of invertases: cell wall invertase CcInv1 (SEQ ID NO:1) and CcInv4 (SEQ ID NO:4—partial sequence), vacuolar invertase CcInv2 (SEQ ID NO. 2), and neutral invertase CaInv3 (SEQ ID NO. 3), and four full length invertase inhibitors: CcInvI1 (SEQ ID NO. 5), CcInvI2 (SEQ ID NO. 6), CcInvI3 (SEQ ID NO. 7), and CcInvI4 (SEQ ID NO. 8).

Another aspect of the invention relate to the proteins produced by expression of these nucleic acid molecules and their uses. The deduced amino acid sequences of the proteins produced by expression of SEQ ID NOS: 1, 2, 3, 4, 5, 6, 7 and 8 are set forth herein as SEQ NOS: 9, 10, 11, 12, 13, 14, 15, and 16, respectively. Still other aspects of the invention relate to uses of the nucleic acid molecules and encoded polypeptides in plant breeding and in genetic manipulation of plants, and ultimately in the manipulation of coffee flavor, aroma and other qualities.

Although polynucleotides encoding invertase and invertase inhibitors from *Coffea canephora* are described and exemplified herein, this invention is intended to encompass nucleic acids and encoded proteins from other *Coffea* species that are sufficiently similar to be used interchangeably with the *C. canephora* polynucleotides and proteins for the purposes described below. Accordingly, when the terms "invertase" and "invertase inhibitor" are used herein, they are intended to encompass all *Coffea* invertases and invertase inhibitors having the general physical, biochemical and functional features described herein, and polynucleotides encoding them, unless specifically stated otherwise.

Considered in terms of their sequences, invertase or invertase inhibitor polynucleotides of the invention include allelic variants and natural mutants of SEQ ID NOS: 1, 2, 3, 4, 5, 6, 7, and 8, which are likely to be found in different varieties of *C. canephora*, and homologs of SEQ ID NOS: 9, 10, 11, 12, 13, 14, 15, and 16 are likely to be found in different coffee species. Because such variants and homologs are expected to possess certain differences in nucleotide and amino acid sequence, this invention provides (1) isolated invertase-encoding nucleic acid molecules that encode respective polypeptides having at least about 70% (and, with increasing order of preference, 71%, 72%, 73%, 74%, 75%, 76%, 77%, 78%, 79%, 70%, 81%, 82%, 83%, 84%, 85%, 86%, 87%, 88%, 89%, 90%, 91%, 92%, 93%, 94%, 95%, 96%, 97%, 98% and 99%) identity with the encoded polypeptide of any one of SEQ ID NOS: 9, 10, 11 or 12, and (2) isolated invertase inhibitor-encoding nucleic acid molecules that encode respective polypeptides having at least about 25% (and, with increasing order of preference, 30%, 35%, 40%, 45%, 50%, 55%, 60%, 65%, 70% 71%, 72%, 73%, 74%, 75%, 76%, 77%, 78%, 79%, 70%, 81%, 82%, 83%, 84%, 85%, 86%, 87%, 88%, 89%, 90%, 91%, 92%, 93%, 94%, 95%, 96%, 97%, 98% and 99%) identity with the encoded polypeptide of any one of SEQ ID NOS: 13, 14, 15, or 16 and comprises a nucleotide sequence having equivalent ranges of identity to any one of SEQ ID NOS: 1, 2, 3, 4, 5, 6, 7 or 8, respectively. Because of the natural sequence variation likely to exist among invertases and invertase inhibitors, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOS: 1, 2, 3, 4, 5, 6, 7 or 8 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level of sequence homology with part or all of the coding and/or regulatory regions of invertase or invertase inhibitor polynucleotides may be identified by using hybridization and washing conditions of appropriate stringency. It will be appreciated by those skilled in the art that the aforementioned strategy, when applied to genomic sequences, will, in addition to enabling isolation of sucrose metabolizing enzyme-coding sequences, also enable isolation of promoters and other gene regulatory sequences associated with sucrose metabolizing enzyme genes, even though the regulatory sequences themselves may not share sufficient homology to enable suitable hybridization.

As a typical illustration, hybridizations may be performed, according to the method of Sambrook et al., using a hybridization solution comprising: 5×SSC, 5×Denhardt's reagent, 1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable *E. coli* host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting invertase or invertase inhibitor encoding genes or mRNA in test samples of plant tissue, e.g., by PCR amplification, or for the positive or negative regulation of expression of invertase or invertase inhibitor encoding genes at or before translation of the mRNA into proteins. Methods in which invertase or invertase inhibitor encoding oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

The oligonucleotides having sequences capable of hybridizing with at least one sequence of a nucleic acid molecule of the present invention include antisense oligonucleotides. The antisense oligonucleotides are targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the sucrose invertase-encoding sequence antisense strand is expressed by a transgene. In another embodiment, hybridizing sense and antisense strands of part or all of the invertase-encoding sequence are transgenically expressed. In another embodiment, invertase-genes may be silenced by use of small interfering RNA (siRNA; Elbashir et al., 2001, Genes Dev. 15(2):188-200) using commercially available materials and methods (e.g., Invitrogen, Inc., Carlsbad Calif.). Preferably, the antisense oligonucleotides recognize and silence invertase mRNA or invertase expression.

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides may be produced by expression in a suitable procaryotic or eucaryotic system. For example, part or all of a DNA molecule, such as the cDNAs having SEQ ID NOS: 1, 2, 3, 4, 5, 6, 7 or 8 may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, and, thereafter, purified from the surrounding medium. An alternative approach involves purifying the recombinant protein by affinity separation, e.g., via immunological interaction with antibodies that bind specifically to the recombinant protein.

The polypeptides of the invention, prepared by the aforementioned methods, may be analyzed according to standard procedures.

Polypeptides purified from coffee or recombinantly produced, may be used to generate polyclonal or monoclonal antibodies, antibody fragments or derivatives as defined herein, according to known methods. In addition to making antibodies to the entire recombinant protein, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Vectors, Cells, Tissues and Plants:

Also featured in accordance with the present invention are vectors and kits for producing transgenic host cells that contain a invertase or invertase inhibitor encoding polynucleotide or oligonucleotide, or variants thereof in a sense or antisense orientation, or reporter gene and other constructs under control of sucrose metabolizing enzyme-promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a invertase- or invertase inhibitor-encoding gene, or nucleic acid sequences that inhibit the production or function of a plant's endogenous invertase. This is accomplished by transforming plant cells with a transgene that comprises part of all of a invertase or invertase inhibitor coding sequence, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruwemiensis, C. bengalensis, C. canephora, C. congensis C. Dewevrei, C. excelsa, C. eugenioides, and C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, *cacao* and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a dehydrin or LEA protein coding sequence under control of its natural 5' and 3' regulatory elements is utilized. In other embodiments, dehydrin or LEA protein coding and regulatory sequences are swapped (e.g., CcLEA1 coding sequence operably linked to CcDH2 promoter) to alter the water or protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants expressing invertase or invertase inhibitor coding sequences under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention, in addition to the seed-specific dehydrin or LEA protein promoters of the invention. Non-limiting examples of other seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin, beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. [NOT YET ASSIGNED] and the dehydrin gene promoter described in commonly-owned, co-pending PCT Application No. [NOT YET ASSIGNED]. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase ($neo^r$, $G418^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in the enhancement of the flavor and/or aroma of the coffee beverage or coffee products ultimately produced from the bean of the coffee plant expressing the protein.

There is a strong correlation between the sucrose concentration in green beans and high quality coffee (Russwurm, 1969; Holscher and Steinhart, 1995; Badoud, 2000; fly and Viani, 1995; Leloup et al., 2003). Improvement of coffee grain sucrose content can be obtained by (1) classical breeding or (2) genetic engineering techniques, and by combining these two approaches. Both approaches have been considerably improved by the isolation and characterization of sucrose metabolism-related genes in coffee, in accordance with the present invention. For example, the sucrose metabolism enzyme-encoding genes may be genetically mapped and Quantitative Trait Loci (QTL) involved in coffee flavor can be identified. It would be then be possible to determine if such QTL correlate with the position of sucrose related genes. Alleles (haplotypes), for genes affecting sucrose metabolism may also be identified and examined to determine if the presence of specific haplotypes are strongly correlated with high sucrose. These "high sucrose" markers can be used to advantage in marker assisted breeding programs. A third advantage of isolating polynucleotides involved in sucrose metabolism is to generate expression data for these genes during coffee bean maturation in varieties with high and low sucrose levels, examples of which are discussed in the Examples, below. This information is used to direct the choice of genes to use in genetic manipulation aimed at generating novel transgenic coffee plants that have increased sucrose levels in the mature bean, as described in detail below.

In one aspect, the present invention features methods to alter the sucrose metabolizing enzyme profile, or sugar profile, in a plant, preferably coffee, comprising increasing or decreasing an amount or activity of one or more sucrose metabolizing enzymes in the plant. Specific embodiments of the present invention provide methods for altering the sugar profile of a plant by increasing or decreasing production of invertases or invertase inhibitors.

The data produced in accordance with the present invention strongly indicate that a decrease in invertase activity (acid or neutral invertases) at the final stages of coffee grain maturation will lead to increased sucrose accumulation in the grain. Accordingly, one preferred embodiment of the present invention comprises transforming coffee plants with an invertase inhibitor-encoding polynucleotide, such as a cDNA corresponding to SEQ ID NO: 5, 6, 7 or 8, for the purpose of over-producing that inhibitor in various tissues of coffee. In one embodiment, coffee plants are engineered for a general increase in invertase inhibitor production, e.g., through the use of a promoter such as the RuBisCo small subunit (SSU) promoter or the CaMV35S promoter functionally linked to an invertase inhibitor gene. In another embodiment designed to limit overproduction of the invertase inhibitor only to the sink organ of interest, i.e., the grain, a grain-specific promoter may be utilized, particularly one of the *Coffea* grain-specific promoters described above.

The sucrose profile of a plant may be enhanced by modulating the production, or activity, of one or more invertase or invertase inhibitor in the plant, such as coffee. Additionally, plants expressing enhanced sucrose levels may be screened for naturally-occurring variants of the invertase or invertase inhibitor. For instance, loss-of-function (null) mutant plants may be created or selected from populations of plant mutants currently available. It will also be appreciated by those of skill in the art that mutant plant populations may also be screened for mutants that under or over-express a particular sucrose metabolizing enzyme, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

The nucleic acids of the invention can be used to identify mutant forms of sucrose metabolizing enzymes in various plant species. In species such as maize or *Arabidopsis*, where transposon insertion lines are available, oligonucleotide primers can be designed to screen lines for insertions in the invertase or invertase inhibito rgenes. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected invertase protein to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al, 1997, Genetics 145: 163-171; Kolch et al., 1991, Nature 349: 426-428).

Another kind of transgenic null mutant can be created by inhibiting the translation of sucrose metabolizing enzyme-encoding mRNA by "post-transcriptional gene silencing." These techniques may be used to advantage to down-regulate invertases in a plant grain, thereby promoting sucrose accumulation. For instance, an invertase-encoding gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 13959-13964). In this regard, dsRNA containing sequences that correspond to part or all of at least one intron have been found particularly effective. In one embodiment, part or all of the invertase-encoding sequence antisense strand is expressed by a transgene. In another embodiment, hybridizing sense and antisense strands of part or all of the coding sequence are transgenically expressed.

In another embodiment, genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, Differentiation 72: 65-73; Baulcombe, 2004, Nature 431: 356-363; Herr, 2004, Biochem. Soc. Trans. 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by an common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16(6): 651-659). Plant cells are transformed with a copy of the endogenous gene targeted for repression. In many cases, this results in the complete repression of the native gene as well as the transgene. In one embodiment, an invertase-encoding gene from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of sucrose metabolizing enzymes and its affects on sucrose levels, thereby affecting the flavor, aroma and other features of coffee seeds. Plants containing one transgene or a specified mutation may also be crossed with plants containing a complementary transgene or genotype in order to produce plants with enhanced or combined phenotypes.

The following examples are provided to describe the invention in greater detail. The examples are for illustrative purposes, and are not intended to limit the invention.

Example 1

Materials and Methods for Subsequent Examples

Plant Material. Tissues from either leaves, flowers, stem, roots, or cherries at different stages of development were harvested from *Coffea arabica* L. cv. *Caturra* T2308 grown under greenhouse conditions (25° C., 70% RH) or from *Coffea canephora* BP409 (*robusta*) grown in the field at the Indonesian Coffee and *Cacao* Research Center (ICCRI), Indonesia. The fruit was harvested at defined stages and frozen immediately in liquid nitrogen, and then packaged in dry ice for transport. Cherries from FRT05, FRT64 (*Robusta*) and CCCA12 (*Arabica*) were obtained from trees cultivated in Quito, Ecuador. Samples were frozen at −25° C. for transportation, then stored at −80° C. until use.

Universal Genome Walker. Genomic DNA from BP409 was extracted from leaves harvested from greenhouse-grown trees according Crouzillat et al., 1996. Genomic DNA was digested with four different restriction enzymes (DraI, EcoRV, PvuI, StuI) and the resulting fragments were ligated blunt-end to the GenomeWalker Adaptor provided by the Universal GenomeWalker kit (BD Biosciences). Both sets of reactions were carried out in accordance with the kit user manual. The four libraries were then employed as templates in PCR reactions using Gene-Specific Primers (GSP) (Table 1). The reaction mixtures contained 1 μl of GenomeWalker library template, 10 nmol of each dNTP, 50 pmol of each primer and 1 U of DNA polymerase (Takara, Combrex Bio, Belgium) in a final volume of 50 μl with the appropriate buffer from Takara. The following conditions were used for the first PCR: after pre-denaturing at 95° C. for 2 min, the first seven cycles were performed at a denaturing temperature of 95° C. for 30 s, followed by an annealing and elongation step at 72° C. for 3 min. A further 35 cycles were carried out, with the denaturation step at 95° C. for 30 s followed by the annealing/elongation step at 67° C. for 3 min. Products from the first amplification using the primer AP1/GSP-GW1 served as template for the second PCR using AP2/GSP-GWN1, with AP2 and GSP-GWN as primers. The second PCR used 2 μl of the first amplification reaction (undiluted and different dilutions up to 1:50), and was performed as described above for the first reaction, with the exception that the second reaction used only 25 cycles of amplification. The resulting PCR fragments were separated and purified by agarose gel electrophoresis. PCR fragments from the major bands were purified, cloned and sequenced.

TABLE 1

List of primers used for Genome Walker experiments

| Primers | Sequences | SEQ ID NO.: |
|---|---|---|
| AP1 | 5'gtaatacgactcactatagggc3' | 31 |
| AP2 | 5'actatagggcacgcgtggt3' | 32 |
| INV1-GW1 | 5'gcgatttgacccattctatcaggtacg3' | 33 |
| INV1-GWN1 | 5'ttgctggttcttagggtctatgccagt3' | 34 |
| INV3-GW1 | 5'acaatggtggatcttggccagt3' | 35 |
| INV3-GWN1 | 5'tttgtcagcaggtccacgaggag3' | 36 |
| INV3-GW2 | 5'acaatggtggatcttggccagt3' | 37 |
| INV3-GWN2 | 5'tttgtcagcaggtccacgaggag3' | 38 |
| INV3-GW3 | 5'ggatacaaaaccagtaaagccagaagtgct3' | 39 |
| INV3-GWN3 | 5'gttgcagaattggattactgggtactg3' | 40 |
| INV3-GW4 | 5'tccagagtcaactggagcaactcttcca3' | 41 |
| INV3-GWN4 | 5'atgccagagcacttggcacaaagtctcgt3' | 42 |
| INV3-GW5 | 5'gagagcttcccaagcatcagcaaccata3' | 43 |
| INV3-GWN5 | 5'agacaactcgctcagtgatctctcatca3' | 44 |

DNA sequence analysis. For DNA sequencing, recombinant plasmid DNA was prepared and sequenced according to standard methods. Computer analysis was performed using DNA Star (Lasergene) software. Sequence homologies were verified against GenBank databases using BLAST programs (Altschul et al. 1990).

cDNA preparation. RNA was extracted from different tissues, i.e., root, stem, leaves, flowers, pericarp and grain at four different maturation stages SG (small green), LG (large green), Y (yellow), R (red), as described previously (Benamor and Mc Carthy, 2003). cDNA was prepared from total RNA and oligo dT(18) (Sigma) as follows: 1 μg total RNA sample plus 50 ng oligo dT was made up to 12 μl final volume with DEPC-treated water. This mixture was subsequently incubated at 70° C. for 10 min and then rapidly cooled on ice. Next, 4 μl of first strand buffer (5×, Invitrogen), 2 μl of DTT (0.1 M, Invitrogen) and 1 μl of dNTP mix (10 mM each, Invitrogen) were added. These reaction mixes were preincubated at 42° C. for 2 min before adding 1 μl-SuperScript III Rnase H-Reverse transcriptase (200 U/μl, Invitrogen). Subsequently, the tubes were incubated at 42° C. for 50 min, followed by enzyme inactivation by heating at 70° C. for 10 min. The cDNA samples generated were then diluted one hundred fold and 5 μl of the diluted cDNA were used for Q-PCR.

3' RACE (Rapid Amplification of 3' cDNA ends) for CcINV1 cDNA isolation. RNA was extracted from pericarp and grain at four different maturation stages SG, LG, Y, R as described previously (Benamor and Mc Carthy, 2003; Benamor et al, report in preparation). Then cDNA was prepared from total RNA using $dT_{(18)}$-Tail (5'cttccgatccctacgcttttttttttttttttt3') (SEQ ID NO:45) primer as follows: 1 ug total RNA sample plus 50 ng $dT_{(18)}$-Tail primer was made up to 12 μl final with DEPC-treated water. This mixture was subsequently incubated at 70° C. for 10 min and then rapidly cooled on ice. Next, 4 μl of first strand buffer (5×, Invitrogen), 2 μl of DTT (0.1 M, Invitrogen) and 1 μl of dNTP mix (10 mM each, Invitrogen) were added. These reaction mixes were preincubated at 42° C. for 2 min before adding 1 μl-SuperScript III Rnase H-Reverse transcriptase (200 U/μl, Invitrogen). Subsequently, the tubes were incubated at 42° C. for 50 min, followed by enzyme inactivation by heating at 70° C. for 10 min. The cDNA samples generated were used in a PCR reaction with Inv1-3'a1 (5'gacgtgaatggttgctggtcagg3') (SEQ ID NO:46) and Tail-3'RACE (5'cttccgatccctacgc3') (SEQ ID NO:47) as primers for the first PCR and Inv1-3'a2 (5'tacagtgggtgctgagctttggt3') (SEQ ID NO:48) and Tail-3'RACE as primers for the second PCR. The PCR reactions were performed in 50 μl reactions as follows: 5 μL of cDNA; 1×PCR buffer (La PCR Buffer II $Mg^{++}$ plus), 800 nM of the each gene specific primer, 200 μM each dNTP, 0.5 U of DNA polymerase Takara LA Taq (Cambrex Bio Science). After denaturing at 94° C. for 5 min, the amplification consisted of 35 cycles of 1 min at 94° C., 1 min at 55° C. and 2 min at 72° C. An additional final step of elongation was done at 72° C. for 7 min.

Full length INV1 and INV3 cDNA amplification. In order to amplify full length INV1 and INV3 cDNA, two sets of primers: INV1-ATG (5'atggctagcttttacctctggctaatgtg3') (SEQ ID NO:49), INV1-STOP (5'tcaattctttcgattgatactggcattct3') (SEQ ID NO:50) and INV3-ATG (5'atggagtgtgttagagaatatcaact3') (SEQ ID NO:51), INV3-STOP (5'tcagcaggtccacgaggaggatctct3') (SEQ ID NO:52) have been designed respectively on INV1 or INV3 sequences obtained from the primer walking or 3'RACE experiments. These two primer sets have been used to perform RT-PCR reaction using cDNA samples described above. The PCR reactions were performed in 50 μl reactions as follows: 5 μL of cDNA; 1×PCR buffer (La PCR Buffer II $Mg^{++}$ plus), 800 nM of the each gene specific primer, 200 μM each dNTP, 0.5 U of DNA polymerase Takara LA Taq (Cambrex Bio Science). After denaturing at 94° C. for 5 min, the amplification consisted of 35 cycles of 1 min at 94° C., 1 min at 55° C. and 2 min at 72° C. An additional final step of elongation was done at 72° C. for 7 min. Fragments obtained have been purified from agarose gel, cloned and sequenced.

Quantitative-RT-PCR. TaqMan-PCR was carried out as recommended by the manufacturer (Applied Biosystems, Perkin-Elmer). The cDNA samples used in this experiment have been described earlier. All reactions contained 1× TaqMan buffer (Perkin-Elmer) and 5 mM $MgCl_2$, 200 μM each of dATP, dCTP, dGTP and dTTP, 5 μl cDNA, and 0.625 units of AmpliTaq Gold polymerase. PCR was carried out using 800 nM of each gene specific primers, forward and reverse, and 200 nM TaqMan probe. Primers and probes were designed using PRIMER EXPRESS software (Applied Biosystems, Table 2). Reaction mixtures were incubated for 2 min at 50° C., 10 min at 95° C., followed by 40 amplification cycles of 15 sec at 95° C./1 min at 60° C. Samples were quantified in the GeneAmp 7500 Sequence Detection System (Applied Biosystems). Transcript levels were determined using rpl39 as a basis of comparison.

TABLE 2

List of primers and probes used for Q-PCR experiment

| Protein | cDNA | Primers and probe | Sequences | SEQ ID NO.: |
|---|---|---|---|---|
| Invertases | CcInv1 | CcInv1 F2 | GTGAATGGTTGCTGGTCAGGAT | 53 |
| | | CcInv1 R2 | CAGTGTAGAGAATGGCTGGGTTTT | 54 |
| | | CcInv1 MGB2 | AACGACAATGCTTCGAGGG | 55 |
| | CcInv2 | CcInv2 F2 | AGTTTATCCGACCAAGGCAATC | 56 |
| | | CcInv2 R2 | TCACCCCTGTGGCATTGTT | 57 |
| | | CcInv2 MGB2 | CAGCGCGACTCTT | 58 |
| | CcInv3 | CcInv3 F1 | CTTGCTGAGAGCCGTTTGCT | 59 |
| | | CcInv3 R1 | CAATATATCTACCAAGTTTGCCATCATAG | 60 |
| | | CcInv3 MGB1 | AGGACAGTTGGCCTGAGT | 61 |
| Invertases Inhibitors | CcInvI1 | CcInvI1 F1 | CGCCGTTGAGGCAGTTAGA | 62 |
| | | CcInvI1 R1 | TTAGCTCCTTGATGCTTTGCAA | 63 |
| | | CcInvI1 MGB1 | ACAAGGCAAACTCA | 64 |
| | CcInvI2 | CcInvI2 F1 | AGGTGCATGATCAGACAATTGC | 65 |
| | | CcInvI2 R1 | GCACTGCCGGACATAAGGAT | 66 |
| | | CcInvI2 MGB1 | AGGGCAAGAAGCTG | 67 |
| | CcInvI3 | CcInvI3 F1 | GTTACTGCAAAGCCGCGTTTA | 68 |
| | | CcInvI3 R1 | GAAGAAATGCTAAGGTGGCTAGTTTT | 69 |
| | | CcInvI3 MGB1 | AGCATGGAGATTGAAGC | 70 |
| | CcInvI4 | CcInvI4 F1 | CGATTGCAAGCTGGTGATTATG | 71 |
| | | CcInvI4 R1 | TTCAGTTTGAGCTGCTGATGCT | 72 |
| | | CcInvI4 MGB1 | AGGCGTGAATATCA | 73 |
| | rp139 | rp139 F1 | GAACAGGCCCATCCCTTATTG | 74 |
| | | rp139 R1 | CGGCGCTTGGCATTGTA | 75 |
| | | rp139 MGB1 | ATGCGCACTGACAACA | 76 |

MGB Probes were labelled at the 5' with fluorescent reporter dye 6-carboxyfluorescein (FAM) and at the 3' with quencher dye 6-carboxy-tetramethyl-rhodamine (TAMRA). rp139 probe was labeled at the 5' with fluorescent reporter dye VIC and at the 3' end with quencher TAMRA. All sequences are given 5' to 3'

Soluble Sugars quantification. Grain tissues were separated from pericarp and hulls. The grains were homogenized in a cryogenic grinder with liquid nitrogen and the powder obtained was lyophilized for 48 hours (Lyolab bII, Secfroid). Each sample was weighed and suspended in 70 ml of double-distilled water previously pre-heated to 70° C., then shaken vigorously and incubated for 30 min at 70° C. After cooling to room temperature, the sample was brought to 100 ml by adding doubled-distilled water, and then paper filtered (Schleicher and Schuell filter paper 597.5). Sugars of extracted coffee grain tissues were separated by HPAE-PED according to Locher et al., 1998 using a Dionex PA 100 (4×250 mm) column. Sugar concentration was expressed in g per 100 g of DW (dry weight).

Enzymatic Activity analysis. Neutral and acid invertase activities were measured according King et al., 1997.

Example 2

Identification of cDNA Encoding Invertase Proteins in *C. canephora*

More than 47,000 EST sequences were identified from several coffee libraries made with RNA isolated from young leaves and from the grain and pericarp tissues of cherries harvested at different stages of development. Overlapping ESTs were subsequently "clustered" into "unigenes" (i.e., contigs) and the unigene sequences were annotated by doing a BLAST search of each individual sequence against the NCBI non-redundant protein database.

Enzymes directly involved in the synthesis and degradation of sucrose have been widely studied in plants, and especially during fruit, tuber, and seed development in plants such as tomato (*Lycopersicon esculentum*), potato (*Solanum tuberosum*) and corn (*Zea mays*). DNA sequences coding for all known key proteins involved in sucrose synthesis and degradation have been identified and characterized in several species and are available in GenBank. Accordingly, the known sequences of plant enzymes, especially sequences from organisms closely related to coffee (e.g., tomato and potato), were used to find similar sequences present in the above-described EST libraries and in other coffee cDNA libraries. To search the aforementioned EST collection, protein sequences of tomato and potato were used in a tBLASTn search of the "unigene" set 5 as described in Example 1. Those in-silica "unigenes" whose open reading frames showed the highest degree of identity with the "query" sequence were selected for further study. In some cases, the selected "unigenes" contained at least one EST sequence that potentially represented a full length cDNA clone, and that clone was then selected for re-sequencing to confirm both its identity and the "unigene" sequence.

Based on their solubility, subcellular localization, pH-optima and isoelectric point, three different types of invertase isoenzymes can be distinguished: vacuolar (InvV), cell wall bound (InvCW) and neutral (InvN) invertases. InvV and InvCW have similar enzymatic and biochemical properties and share a high degree of overall sequence homology and two conserved amino acid motifs. One common feature is the pentapeptide N-DPN-G/A (SEQ ID NO:77) (β-Fructofuranosidase-motif; Sturm and Chrispeels, 1990; Roitsch and Gonzalez, 2004). The second conserved feature is the highly conserved cysteine sequence WECX(P/V)DF (SEQ ID NO:78) (Sturm and Chrispeels, 1990) in which V and P distinguish the Vacuolar and cell-wall (Periplasmic) invertase respectively.

To find cDNA encoding the three invertase isoenzymes in coffee, protein sequences corresponding to (1) the tomato vacuolar invertase TIV-1, (2) the tomato cell wall invertase LIN6, and (3) the *A. thaliana* neutral (cytoplasmic) invertase-like protein have been used to perform a similarity search of the unigene set using the tBLASTn algorithm.

A. CcInv2 (SEQ ID NO: 10)

The ORF of unigene #127336 was found to have a high degree of homology with the tomato vacuolar invertase TIV-1 (NCBI Protein Identifier No. P29000; Klann et al., 1992). The single EST in this unigene, clone ccc120f11, was isolated and its insert fully sequenced. The cDNA insert was found to be 2212 bp long. The complete ORF sequence of this clone was 1761 bp long, starting at position 192 and finishing at position 1952. The deduced protein was 586 aa long with a predicted molecular weight of 64 kDa. The protein encoded by ccc120f1I has been annotated CcInv2 (*Coffea canephora* Invertase 2). CcInv2 is 69.6% identical to the tomato vacuolar invertase TIV-1 and 68.5% identical to an invertase characterized in potatoSTVInv FIG. 2). Marraccini et al. have recently placed a partial cDNA sequence from *Coffea arabica* potentially encoding a vacuolar invertase in the public databases (NCBI Nucleotide Identifier No. AJ575258. They have called this partial protein sequence Inv2 (NCBI Protein Identifier No. CAE01318). Partial alignment between CcInv2 and inv2 has shown 93.8% of identity (FIG. 2). The proposed vacuolar localization of this robusta invertase is supported by the presence of a V in the highly conserved WECVDF (SEQ ID NO:78 wherein Xaa is Val) domain FIG. 2, Sturm and Chrispeels, 1990) whereas inv2 protein sequence is characterized by the presence of a P in this domain suggesting that inv2 may be a cell wall bound invertase. The alignment in FIG. 2 shows that the N-terminal region of CcInv2 is shorter than those seen for two homologues from other plants. However, the cDNA insert of ccc120f11 actually starts 190 bp beyond the first amino acid shown for CcInv2 in FIG. 2. This 190 bp sequence has two open reading frames, but neither are in-frame with the major ORF. In addition, the amino acid sequences of the short ORFs do not correspond to sequences seen in the other two homologous sequences FIG. 2). These results could be explained by either the N-terminal region of this *Coffea canephora* protein being shorter than the comparable region in homologous proteins of other plants, or the presence of an intron in this region of the cDNA clone.

B. CcInv3 (SEQ ID NO: 11)

The protein encoded by the clone cccp28p22 (unigene #96095) has a high homology to the neutral cytoplasmic invertase from *A. thaliana* (Protein Identifier No. NP_567347). The protein encoded by cccp28p22 clone has been annotated CcInv3 (*Coffea canephora* Invertase 3). According to the optimal alignment obtained, the cDNA insert of cccp28p22 is not full-length, i.e., it does not code for the entire protein (approximately 1500 bases are missing). Using several rounds of primer directed genome walking, we have been able to amplify the genomic sequence from *C. canephora* corresponding to the 5' region upstream cccp28p22 sequence. Using specific primers, we have amplified the full length cDNA by RT-PCR. Several RNA samples from *C. arabica* and *C. canephora* were used, positive amplification corresponding to the full length cDNA sequence was only obtained using RNA extracted from *arabica* grain at yellow stage. The protein encoded by this new cDNA sequence has been annotated CaInv3 (*Coffea arabica* Invertase 3). The CaInv3 cDNA is 1675 bp long. The deduced protein is 558 as long, with a predicted molecular weight of 63.8 kDa. The protein sequence encoded by the CaInv3 cDNA shows a very high level of homology (83.7%) with the neutral cytoplasmic invertase from *A. thaliana* (FIG. 3).

C. CcInv4 (SEQ ID NO: 12)

The protein encoded by the clone cccs46w27d20 (unigene #123705) has a significant degree of identity (62.7%) with the tomato cell wall bound invertase LIN6 (NCBI Protein Identifier No. AAM28823). The alignment is shown in FIG. 4. According to the optimal alignment obtained, the cDNA insert of cccs46w27d20 is not full-length i.e. it does not code for the entire protein (approximately 1500 bases are missing). It is important to note that the protein encoded by cccs46w27d20 shares also 38% of identity with the tomato vacuolar invertase TIV-1 (Klann et al., 1992). The protein encoded by cccs46w27d20 clone has been annotated CcInv4 (*Coffea canephora* Invertase 4). This protein shares higher homology with vacuolar invertase than cell wall bound invertase. Genome Walker and 5' RACE have been carried out to isolate 5' end missing region.

Based on the data presented above, we have isolated one cDNA encoding each type of invertase isoenzyme from the *C. canephora* database.

D. CcInv1 (SEQ ID NO: 9)

A homologous full length cDNA sequence from *C. canephora* (*robusta*) was isolated using a partial cDNA sequence encoding a cell wall invertase from *Coffea arabica* (made available by Marraccini et al.: NCBI Nucleotide Identifier No. AJ575257, and the encoded partial protein sequence (Inv1) NCBI Protein Identifier No. CAE1317.1). Using the partial cDNA sequence and the 3'RACE, as well as "primer assisted" genome walking experiments, as described in Example 1, the homologous full length cDNA was found to be 1731 bp long and the deduced protein was 576 aa long with a predicted molecular weight of 64.6 kDa. This protein has been annotated CcInv1 (*Coffea canephora* Invertase 1).

The protein sequence obtained for CcInv1 is not identical to the sequence obtained by Marraccini et al., having 4 amino acid differences over the 163 amino acids known for the partial arabica cDNA sequence. An alignment of CcInv1 with several highly homologous database sequences shows that CcInv1 has 55.2% identity with the tomato cell wall bound LIN6 and 54.3% identity with DCCW Inv (FIG. 5), a cell wall bound invertase identified in carrot. The proposed cellular localization of CcInv1 is supported by the presence of a P in the highly conserved WECPDF (SEQ ID NO:28) domain (FIG. 5, Sturm and Chrispeels, 1990).

Example 3

Identification of cDNA Encoding Invertase Inhibitor Proteins in *C. canephora*

Recent publications this past decade have shown that activity of invertases can be regulated at the post-translational level by interaction with a group of small molecular weight proteins (<20 kDa) called invertase inhibitors (Greiner et al., 1998; Greiner et al., 2000; Helentjaris et al., 2001; Bate et al., 2004). Many sequences from several plant species have been identified in the public databases but few of them are characterized biochemically. Recently, two invertase inhibitors, NtINVINH1 from tobacco (Protein Identifier No. CAA73333; Greiner et al., 1998) and ZM-INVINH1 from maize (Nucleotide Identification No. AX214333; Bate et al., 2004 corresponding to protein ID. 1 in Helentjaris et al., 2001) have been biochemically characterized. For example, ZM-INVINH1 has been shown to directly control sucrose metabolism by its capability to act as a sucrose sensor (Bate et al., 2004). In the presence of high sucrose concentrations, the invertase inhibitor ZM-INVINH1 remains inactive, allowing sucrose hydrolysis during early fruit development. When the sucrose levels fall below a specific level, this invertase inhibitor then becomes active and inhibits the invertase activity (Helentjaris et al., 2001; Bate et al., 2004).

Invertase inhibitor sequences from many different organisms (tomato, tobacco, maize and *A. thaliana*) are available in GenBank, but most of them have been annotated based simply on homology results obtained using BLAST and not by the direct characterization of their biochemical activity. It is noted that the relatively small number of invertase inhibitors that have been characterized biochemically generally show weak homologies to one another (Bate et al., 2004), and to date, this class of protein has no defined highly conserved sequence motifs (Bate et al., 2004). Therefore, database entries annotated as "invertase inhibitors" or "invertase inhibitor-like protein" must be interpreted with caution. To perform the blast search in the coffee databases for coffee invertases, we used sequences encoding for the biochemically characterized invertase inhibitors ZM-INVINH1, NtInvI and protein ID. 31 in Helentjaris et al., 2001 (Protein Identifier No. CAC69345).

Based on this search, four clones cccp2d1 (unigene #124209), cccs30w14i24 (unigene #125332), cccs30w24n8 (unigene #122705) and A5-1462 with similarity to database invertase inhibitors have been identified in the EST databases.

A. CcInvI1 (SEQ ID NO: 13)

The 670 bp cDNA insert of cccp2d1 clone is apparently full length, with a complete ORF sequence of 558 bp, encoding a protein with a potential molecular weight of 20.7 kDa. The protein sequence of cccp2d1 is 31.2% identical to the invertase inhibitor ZM-INVINH1 characterized in corn (Bate et al., 2004) (FIG. 6). This cDNA has been annotated CcInvI1 (*Coffea Canephora* Invertase Inhibitor 1).

B. CcInvI2 (SEQ ID NO: 14)

The 629 bp cDNA insert of cccs30w14i24 clone is apparently full length, with a complete ORF sequence of 537 bp, encoding for a protein with a potential molecular weight of 19.6 kDa. The protein sequence of cccs30w14i24 is 34.6% identical to the invertase inhibitor NtInvI characterized in tobacco (Greiner et al., 1998; Weil et al., 1994) (FIG. 6). This cDNA has been annotated CcInvI2 (*Coffea Canephora* Invertase Inhibitor 2).

C. CcInvI3 (SEQ ID NO: 15)

Blast screening of the cDNA library described in PCT application PTC/EP2004/006805 resulted in the discovery of the cDNA clone A5-1462. The 704 bp cDNA insert of A5-1462 clone is apparently full length, with a complete ORF sequence of 495 bp, encoding for a protein with a potential molecular weight of 18.4 kDa. The protein sequence of A5-1462 is only 13% identical to ZM-INVINH1 (FIG. 6) but 24.4% identical to the protein ID. 31 (Nucleotide Identification No. AX214363; Helentjaris et al., 2001). This cDNA has been annotated CcInvI3 (*Coffea Canephora* Invertase Inhibitor 3).

D. CcInvI4 (SEQ ID NO: 16)

The 640 bp cDNA insert of cccs30w24n8 clone is apparently full length, with a complete ORF sequence of 555 bp, encoding for a protein with a potential molecular weight of 20.2 kDa. The protein sequence of cccs30w24n8 is 20.5% identical to ZM-INVINH1 (FIG. 6) and 25.7% identical to the protein ID. 31 (Nucleotide Identification No. AX214363; Helentjaris et al., 2001). This cDNA has been annotated CcInvI4 (*Coffea Canephora* Invertase Inhibitor 4).

As noted earlier, CcInvI proteins are not well conserved, and share weak homology with ZM-INVINH1 or NtInvI for example. The four "conserved" Cys residues known to be essential for function (Rausch and Greiner, 2003; Scognamiglio et al., 2003; Hothorn et al., 2003; Hothorn et al., 2004) are present in each protein (FIG. 6).

Example 4

Acid and Neutral Invertase Activities During Coffee Bean Maturation

Figure 7:
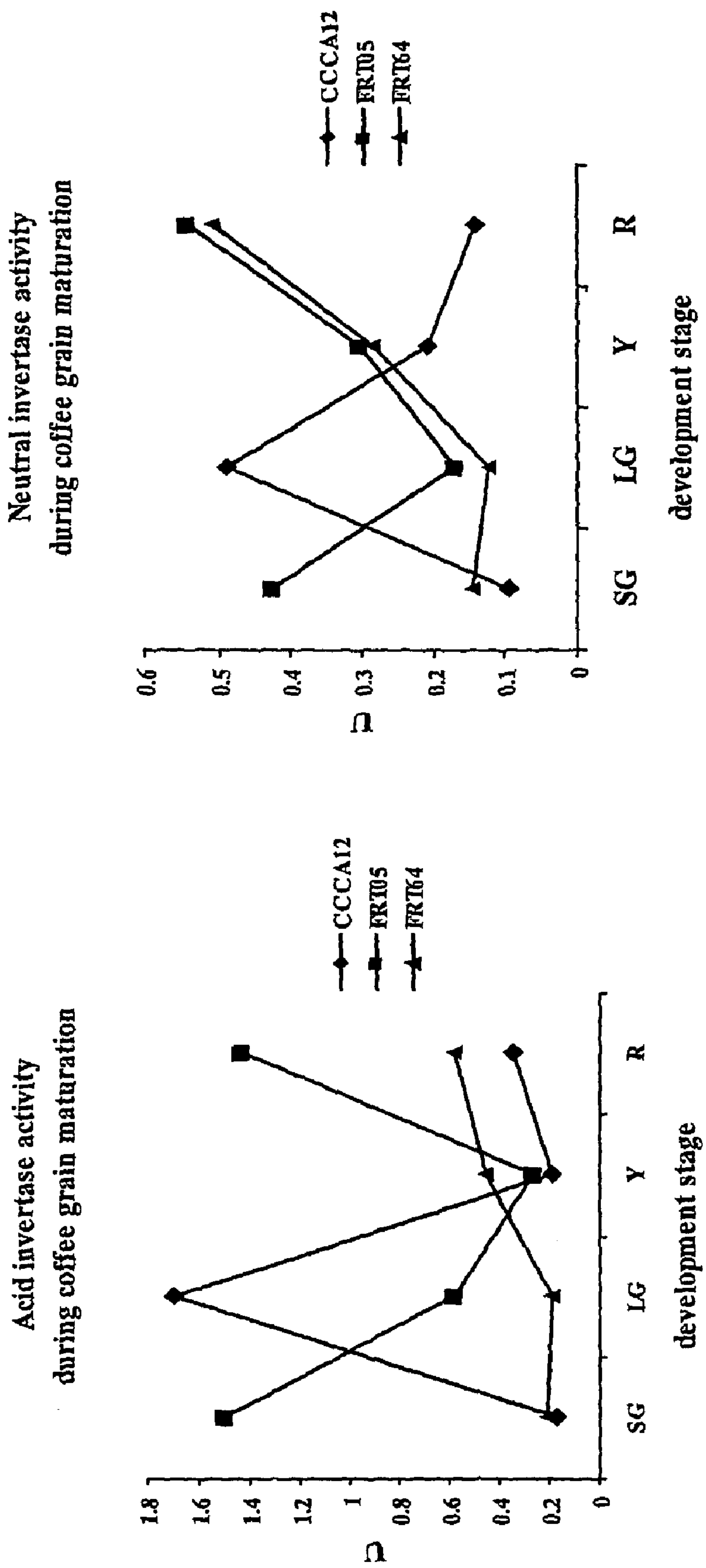
FIG. 7. Changes of acid and neutral invertase activity in whole grains (separated from pericarp and locules) during CCCA12 (*C. arabica*) and FRT05, FRT64 (*C. canephora*). Coffee cherries at four different maturation stages characterized by size and color have been used for this study, i.e., SG (small green), LG (large green), Y (yellow), and R (red). Enzymatic activities are expressed in μmoles·$h^{-1}$·$mg^{-1}$ proteins.

Concentrations of glucose, fructose and sucrose have been determined in whole grains from FRT05 (*robusta*) and CCCA12 (*arabica*) during coffee grain maturation. We have chosen to analyze these two genotypes because they have been previously found to have significantly different levels of sucrose (Charles Lambot, unpublished data). In order to understand the basis for this difference, we analyzed the accumulation of sucrose during grain development of these two varieties, as well as the levels of glucose and fructose. In parallel, acid and neutral invertase activities were examined in order to determine if there might be a correlation between free sugar accumulation and these particular activities. Similar experiments have been carried out using samples from a second *robusta* variety, FRT64. The results are shown in Table 3 and FIG. 7.

TABLE 3

Acid and neutral invertase activities during coffee bean maturation.

| Genotype | Development stage | Sucrose | Glucose | Fructose | Acid Invertase | Neutral Invertase |
|---|---|---|---|---|---|---|
| FRT05 | SG | 0.72 | 1.54 | 0.33 | 1.50 | 0.43 |
| | LG | 1.45 | 1.71 | 0.09 | 0.58 | 0.17 |
| | Y | 3.13 | 0.09 | 0 | 0.26 | 0.3 |
| | R | 6.70 | 0.04 | 0.09 | 1.44 | 0.54 |
| FRT64 | SG | 1.79 | 2.82 | 0.40 | 0.21 | 0.15 |
| | LG | 1.94 | 2.48 | 0.27 | 0.19 | 0.12 |
| | Y | 4.46 | 0.04 | 0 | 0.45 | 0.28 |
| | R | 6.6 | 0.07 | 0.16 | 0.58 | 0.51 |
| CCCA12 | SG | 2.65 | 14.41 | 1.52 | 0.17 | 0.09 |
| | LG | 3.11 | 5.62 | 0.49 | 1.70 | 0.49 |
| | Y | 8.04 | 0.1 | 0.12 | 0.19 | 0.20 |
| | R | 9.83 | 0.08 | 0.1 | 0.34 | 0.14 |

Coffee cherries at four different maturation stages characterized by size and color have been used for this study i.e. SG (small green), LG (large green), Y (yellow) and R (red). Concentrations of sucrose, glucose and fructose in the coffee grain were measured in samples harvested in parallel to those used for the assays of invertase activity. Sugar concentration is expressed in g/100 g DW (dry weight) while enzymatic activities are expressed in μmoles $\cdot$ $h^{-1} \cdot mg^{-1}$ proteins.

A. Sugar Levels During Coffee Grain Maturation

At the earliest stage of maturity examined (stage SG), the main free sugar was glucose but the concentration was 10 times higher in CCCA12 (14%) than FRT05 (1.5%). At the same stage, fructose concentration was also higher in *arabica* (1.5%) than FRT05 (0.3%) but clearly fructose was less accumulated than glucose. By the end of grain development, concentrations of glucose and fructose had decreased to very low levels for both species with only traces being detected at the mature red stage (R). The decrease in these two sugars was accompanied by an increase in sucrose, which approached 100% of total free sugars in mature grains, again being higher in *arabica* (9.82%) than *robusta* (6.71%). The same global remarks can be made on sucrose, glucose and fructose variations during FRT64 coffee bean maturation. Glucose was more accumulated in earliest stage than fructose. At the end of development, sucrose was the major sugar accumulated. Interestingly, even if FRT64 and FRT05 have same final sucrose concentration in R stage (around 6.6% of DW), sucrose was more accumulated in FRT64 than FRT05 samples at all previous stages i.e. SG (60% more), LG (25% more) and Y (30% more). It is important to note that these results represent only free sugar accumulation and do not include their modified form like i.e. UDP-G, F6-P and S6-P that are also directly involved in sucrose metabolism.

B. Invertase Activity (Acid and Neutral) During Coffee Grain Maturation

Acid and neutral enzyme activities evolved similarly during CCCA12 coffee grain maturation. Low acid (0.17 U) and neutral (0.09 U) invertase activities were observed in SG stage of CCCA12. Both enzymatic activities rose drastically between SG and LG stage and reached an activity of 1.70 U for acid invertase and 0.49 U for neutral invertase. In the later stage of development, AI and NI activity declined dramatically to reach approximately similar low levels of activity at the Y stage (0.19 and 0.20 U respectively). Between Y and R stages, while AI activity increased up to 0.34 U, NI activity decreased to 0.14 U. Interestingly, AI and NI activities have similar variations than SuSy activity previously observed for the same samples (See commonly owned, co-pending provisional application No: [NOT YET ASSIGNED]). There is a clear correlation with diminution of both invertase activities and sucrose accumulation in latest stages of CCCA12 grain maturation.

Notably, AI and NI activities evolved in very different fashion for FRT05 and FRT64 versus those observed for CCCA12. AI (1.50 U) and NI (0.43 U) enzymes were highly active early in FRT05 development (stage SG). AI activity decreased drastically between SG and Y stages to reach 0.26 U (almost the same activity than what is observed for CCCA12 at Y stage). AI activity in FRT05 rose up between Y and R stage to reach 1.44 U. Decreased activity of neutral invertase was also observed but only between SG and LG stages. Increased activity of neutral invertase was observed between LG and R stage, NI reached its maximum activity 0.54 U. FRT05 late grain development stage is characterized by high AI and NI activity. For FRT64 genotype, AI activity and NI activities were low in SG FRT64 grain. Both activities stayed stable between SG and LG stages and increased between LG and R stages, increase being higher for the NI than AI. FRT64 had same neutral invertase activity augmentation between LG and R stages than FRT05 but in parallel acid invertase activity is 2.5 higher in FRT05 than FRT64 R stage. In conclusion, FRT05 and FRT64 have same final sucrose concentration in mature grain but invertase mainly acid activity was drastically different.

Overall, it appears that CCCA12 may accumulate more sucrose than FRT05 and FRT64 in part because of weaker global invertase activity at the final stage of maturation. Even if sucrose is synthesized after importation from phloem, invertase activity is preventing in late development sucrose accumulation by immediate degradation in both *robustas*.

Example 5

Invertase and Invertase Inhibitors mRNA Accumulation During Coffee Bean Maturation The expression of the invertase genes CcInv1, CcInv2 and CcInv3 as well as invertase inhibitors genes CcInvI1, 2, 3 and 4 during T2308 (*C. arabica*) and BP409 (*C. canephora*) grain development was characterized. For comparative purposes, we also characterized the expression of these genes in different coffee tissues such as leaf, flower and root. It is noted that these gene expression studies relate to different varieties from those used in the enzyme activity analysis experiments. Nevertheless, this expression data does allow an overall comparison between the expression of these genes in *arabica* versus *robusta*.

RNA had been extracted from BP409 and T2308 coffee cherries at four different maturation stages characterized by size and color, i.e. SG (small green), LG (large green), Y (yellow) and R (red or mature). For each stage, the pericarp and grain were separated before total RNA was extracted as described in Example 1. Total RNA was also extracted from other tissues (leaf, root and flower). Gene expression was analyzed by performing real time RT-PCR (TaqMan, Applied Biosystems). Relative transcript levels were quantified against an endogenous constitutive transcript rpl39. The gene specific primers and the TaqMan probes used are listed in Table 2 above.

Figure 8:
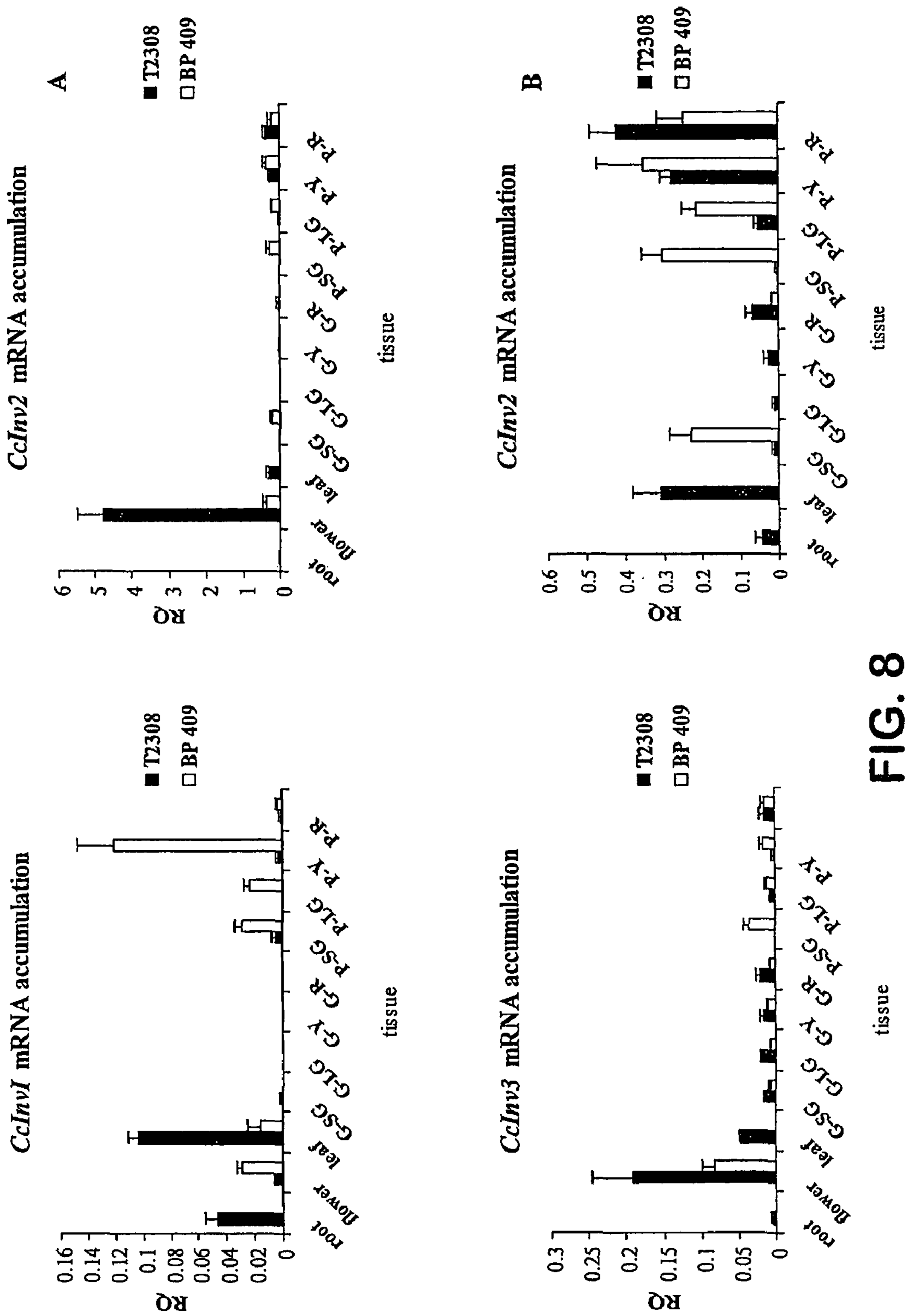
FIG. 8. Tissue-specific expression profile of CcInv1 (cell wall-bound), CcInv2 (vacuolar) (A and B) and CcInv3 (cytoplasmic) invertases in *C. canephora* (*robusta*, BP 409) and *C. arabica* (*arabica*, T2308) using real-time RT-PCR. Total RNA was isolated from root, flower, leaf and coffee beans harvested at four different maturation stages, i.e., Small-Green (SG), Large-Green (LG), Yellow (Y) and Red (R). For each maturation stage, coffee cherries have been separated from pericarp (P) and grains (G). Total RNA was reverse transcribed and subjected to real-time PCR using TaqMan-MGB probes. Relative amounts were calculated and normalized with respect to rpl39 transcript levels. Data shown represent mean values obtained from three amplification reactions and the error bars indicate the SD of the mean.

The first general observation regarding CcInv gene expression is that these genes were found to be poorly expressed, especially in grain, at all maturation stage and for both genotypes (FIG. 8). CcInv1 transcripts (a cell wall invertase) were not detected in grain of either genotype. Interestingly, transcripts for CcInv1 were not detected in T2308 pericarp, while significant levels could be detected in the pericarp of BP 409 at the same stages. Conversely, relatively significant levels of CcInv1 were detected in the roots and leaf tissues of BP409 but not in the same tissues from 12308. This inverse expression strongly suggests that these differences are not due to allelic differences in the BP409 and 12308 genes encoding these transcripts, but are apparently due to differences in the transcript levels of these genes in each genotype. A very high level of CcInv2 expression was detected in the flowers of T7308 relative to the expression in BP409 (FIG. 8, panel A; approximately 10 fold difference, 12308 (4.8 RQ) versus BP409 (0.38 RQ)).

It has been noted previously that there are significant differences in the expression of several other genes in the whole flowers samples of 12308 and BP 409 used here (for example CcHQT, CcPAL1 and CcPAL3, unpublished data), which has led to the idea that these whole flower samples may not be precisely at the same developmental stage. When the expression data for CcInv2 was investigated in more detail (FIG. 8, panel B) it was seen that, apart from the small green grain of *robusta*, CcInv2 was expressed at very low levels in the grain of *arabica* or *robusta*. It is noted however, that there appears to be a slight tendency for the weak expression of CcInv2 in the grain to increase towards maturity. A relatively significant expression of CcInv2 was detected in the *arabica* and *robusta* pericarp tissues, although the pattern of this expression was different.

In all the *arabica* pericarp stages tested, there was relatively similar expression; while in *robusta*, expression of CcInv2 was very low in the small green pericarp and then increased gradually, with the highest expression being detected in the mature pericarp tissue. Low CcInv2 expression was also detected in the roots and leaf of BP 409, but not in T2308.

The highest expression of CcInv3, which is believed to encode a neutral (cytoplasmic) invertase, was found in the flowers of *arabica* and *robusta*. Much lower levels of CcInv3 expression were detected in the other tissues. In all stages in the grain, the level of CcInv3 transcripts appeared to be marginally higher in *arabica* than *robusta*, while in the pericarp, the opposite appeared to be the case, with expression in *robusta* being marginally higher at the large green to red stages than in *arabica*.

While the control of invertases at the transcriptional level is important, significant control can also be exerted at the post-transcriptional level by the interaction of invertase proteins with a group of small molecular weight proteins (<20 kDa) called invertase inhibitors (Greiner et al., 1998; Greiner et al., 2000; Helentjaris et al., 2001; Bate et al., 2004). As noted above, four full-length cDNAs believed to encode invertase inhibitors were isolated from the EST libraries. The results of the expression analysis of these genes are presented in FIG. 9.

Figure 9:
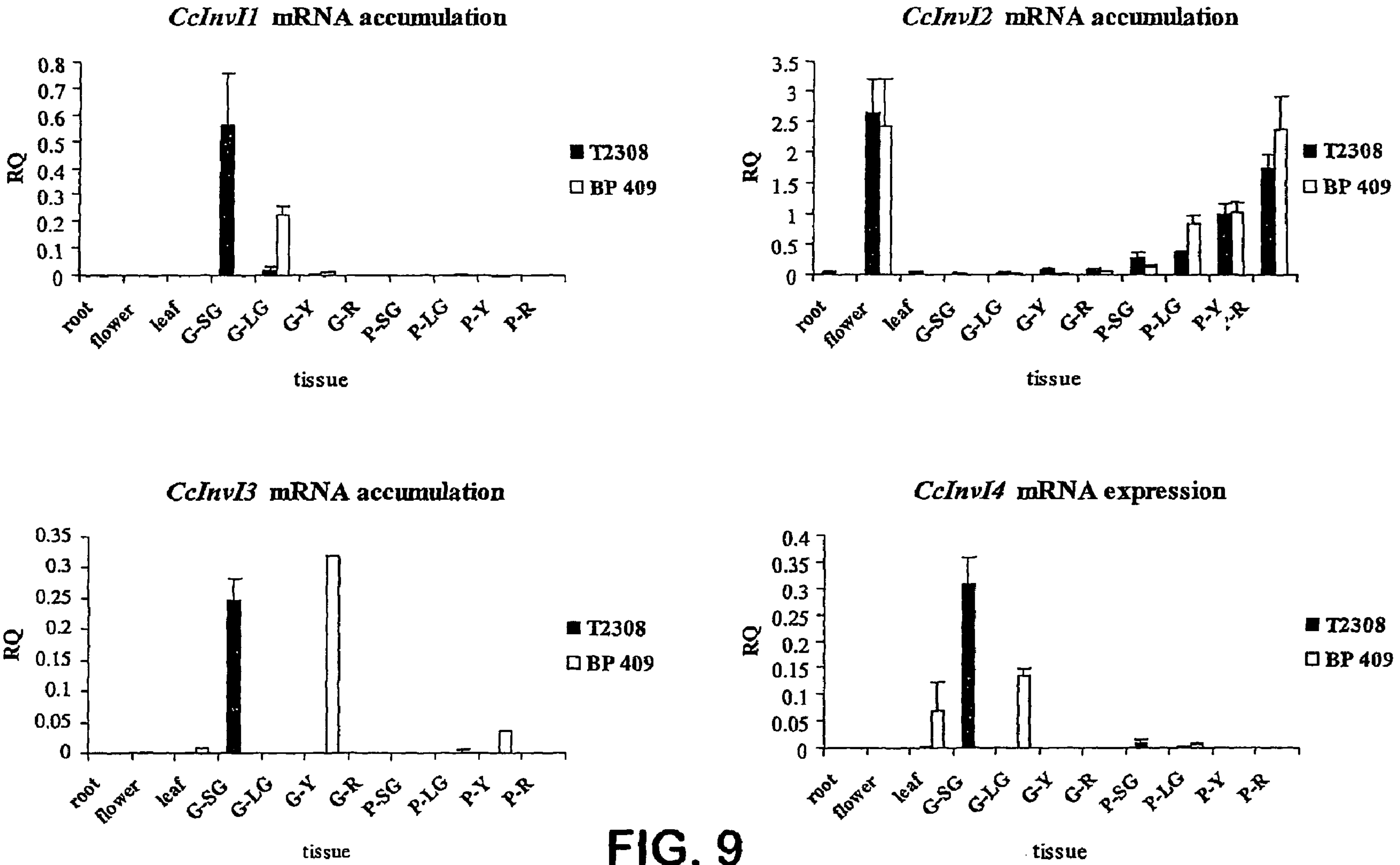
FIG. 9. Tissue-specific expression profile of CcInvI1, CcInvI2, CcInvI3 and CcInvI4 invertase inhibitors in *C. canephora* (*robusta*, BP409) and *C. arabica* (*arabica*, T2308) using real-time RT-PCR. Total RNA was isolated from root, flower, leaf and coffee beans harvested at four different maturation stages, i.e., Small-Green (SG), Large-Green (LG), Yellow (Y), and Red (R). For each maturation stage, coffee cherries have been separated from pericarp (P) and grains (G). Total RNA was reverse transcribed and subjected to real-time PCR using TaqMan-MGB probes. Relative amounts were calculated and normalized with respect to rpl39 transcript levels. The data represent mean values obtained from three amplification reactions and the error bars indicate the SD of the mean.

In *arabica*, CcInv/1 was found to be exclusively expressed in the grain at the small green stage and to a much lesser extent in the large green stage, while in *robusta* this gene was expressed primarily in the large green grain (FIG. 9). Very low levels of CcInvI 1 expression were detected in both *arabica* and *robusta* yellow grain, but not in mature grain (red).

Less specificity was seen for the expression of CcInvI 2 (FIG. 9). This gene is expressed at a relatively high level in whole flowers of both *arabica* and *robusta*. In *arabica* and *robusta* pericarp, CcInvI 2 expression can be detected at relatively low level during the small green stage, but it clearly increases significantly in both species as the cherries mature. CcInvI 2 appears to be expressed at extremely low levels at all stages in the grain, as well as in roots and leaves.

Like CcInvI 1, the expression of CcInvI 3 and CcInvI 4 showed a high level of tissue specificity. CcInv 3 appears to be exclusively expressed in the small green grain of *arabica* and in the yellow grain of *robusta*. CcInvI 4 expression was detected almost exclusively in the small green tissue of *arabica* grain, while in *robusta*, it was expressed in the large green grain as well as to a lesser extent in the leaves.

REFERENCES

Altschul S. F., Madden T. L., Schaffer A. A., Zhang J., Zhang Z., Miller W. and Lipman D. 1990. Gapped BLAST and PSI-Blast: a new generation of protein database search. *Nucleic Acids Res.* 25: 3389-3402.

*Arabidopsis* Genome Initiative. 2000. Analysis of the genome sequence of the flowering plant *Arabidopsis thaliana. Nature.* 408: 796-815.

Badoud R., 2000. "What do we know about coffee chemistry, flavour formation and stability ? Internal Note, 23 Oct. 2000.

Bate N. J., Niu X., Wang Y., Reimann K. S. and Helentjaris T. G. 2004. An invertase inhibitor from maize localizes to the embryo surrounding region during early kernel development. *Plant Physiol.* 134.1-9.

BenAmor M. and Mc Carthy J. 2003. Modulation of coffee flavour precursor levels in green coffee grains. European patent Application No. 03394056.0 NESTEC S. A.

Chahan Y., Jordon A., Badoud R. and Lindinger W. 2002. From the green bean to the cup of coffee: investing coffee roasting by on-line monitoring of volatiles. *Eur Food Res Technol.* 214:92-104.

Cheng W.-H., Taliercio E. W. and Chourey P. S. 1996. The Miniature 1 seed locus of maize encodes a cell wall invertase required for normal development of endosperm and maternal cells in the pedicel. *Plant Cell.* 8:971-983.

Clough, S. J. and Bent A. F. 1998. Floral dip: a simplified method for *Agrobacterium*-mediated transformation of *Arabidopsis thaliana. Plant Journal* 16; 735-743.

Crouzillat D., Lerceteau E., Petiard V., Morera J., Rodriguez H., Walker D., Philips W. R. R., Schnell J., Osei J. and Fritz P. 1996. *Theobroma cacao* L.: a genetic linkage map and quantitative trait loci analysis. *Theor Appl Genet.* 93: 205-214.

Dali N., Michaud D. and Yelle S. 1992. Evidence for the involvement of sucrose phosphate synthase in the pathway of sugar accumulation in sucrose-accumulating tomato fruits. *Plant Physiol.* 99:434-438.

Dickinson C. D., Atabella T. and Chrispeels M. J. 1991. Slow growth phenotype of transgenic tomato expressing apoplastic invertase. *Plant Physiol.* 95:51-57.

Fridman E. and Zamir D. 2003. Functional divergence of a synthetic invertase gene family in tomato, potato and *Arabidopsis. Plant Physiol.* 131: 603-609.

Fridman E, Carrari F, Liu Y S, Fernie A R, Zamir D. 2004. Zooming in on a quantitative trait for tomato yield using interspecific introgressions. *Science.* 305(5691): 1786-9.

Godt, D. E. et T. Roitsch. 1997. Regulation and tissue-specific distribution of mRNAs for three extracellular invertase isoenzymes of tomato suggests an important function in establishing and maintaining sink metabolism. *Plant Physiol* 115:273-282.

Grandillo S. and Tanksley S. D. 1996. QTL analysis of horticultural traits differentiating the cultivated tomato fruit from the closely related species *L. pimpinellifolium. Theor Appl Gene.* 92: 935-951.

Greiner, S. Krausgrill S., and Rausch, T. 1998. Cloning of a tobacco apoplasmic invertase inhibitor. Proof of function of the recombinant protein and expression analysis during plant development. *Plant Physiol.* 1116: 733-742.

Greiner S., Rausch T., Sonnewald U. and Herbers K. 1999. Ectopic expression of a tobacco invertase inhibitor homolog prevents cold-induced sweetening of potato tubers. *Nature Biotech.* 17: 708-711

Greiner S. Köster Lauer K, Rosenkranz H, Vogel R, Rausch T. 2000. Plant invertase inhibitors: expression in cell culture and during plant development. *Australian Journal of Plant Physiology,* 27: 807-814.

Helentjaris, T., Bate, N. J. and Allen, S. M. 2001. Novel invertase inhibitors and methods of use. Patent: WO 0158939. PIONEER HI-BRED INTERNATIONAL, INC. (US); E.I. DU PONT DE NEMOURS AND COMPANY (US)

Holscher, W. and Steinhart, H. 1995. Development in Food Science V37A Food Flavors: Generation, Analysis and Process Influence. Elsevier, 785-803.

Hothorn M., Bonneau F., Stier G., Greiner S. and Scheffzek K. 2003. Bacterial expression, purification and preliminary X-ray crystallographic characterization of the invertase inhibitor Nt-CIF from tobacco. *Acta Cryst D*59:2279-2282.

Hothorn M., Wolf S., Aloy P., Greiner S, and Scheffzek K. 2004. Structural insights into the target specificity of plant invertase and pectin methylesterase inhibitory proteins. *Plant Cell.* 16:3437-3447.

Illy, A. and Viani, R. 1995. Espresso Coffee: The Chemistry of Quality. Academic Press. London Academic Press Ltd.

King S. P., Lunn, J. E. and Furbank R. T. 1997. Carbohydrate content and enzyme metabolism in developing canola siliques. *Plant Physiol.* 114: 153-160.

Klann E., Yelle S. and Bennett A. B. 1992. Tomato acid invertase complementary DNA. *Plant Physiol.* 99: 351-353.

Klann E. M., Chetelat R. T. and Bennett A. B. 1993. Expression of acid invertase gene controls sugar composition in tomato (Lycopersicon) fruit. *Plant Physiol.* 103: 863-870.

Klann E. M., Hall B., and Bennett A. B. 1996. Antisense acid invertase (TIV1) gene alters soluble sugar composition and size in transgenic tomato fruit. *Plant Physiol.* 112: 1321-1330.

Leloup V., Gancel C., Rytz, A. and Pithon, A. 2003. Precursors of *Arabica* character in green coffee, chemical and sensory studies. R&D Report RDOR-RD030009.

Lowe J. and Nelson O. E., Jr. 1946. Miniature seed—A study in the development of a defective caryopsis in maize. *Genetics.* 31: 525-533.

Marraccini P., Deshayes A., Pétiard V. and Rogers W. J. 1999. Molecular cloning of the complete 11S seed storage protein gene of *Coffea arabica* and promoter analysis in the transgenic tobacco plants. *Plant Physiol. Biochem.* 37:273-282.

Marraccini P, Courjault C, Caillet V, Lausanne F, LePage B, Rogers W, Tessereau S, and Deshayes A. 2003. Rubisco small subunit of *Coffea arabica*: cDNA sequence, gene cloning and promoter analysis in transgenic tobacco plants. *Plant Physiol. Biochem.* 41:17-25.

Miller M. E. and Chourey P. S. 1992. The maize invertase-deficient miniature-1 seed mutation is associated with aberrant pedicel and endosperm development. *Plant Cell.* 4: 297-305.

Miron D. and Schaffer A. A. 1991. Sucrose phosphate synthase, sucrose synthase and invertase activities in developing fruit of *Lycopersicon hirsutum* Humb. And Bonpl. Plant Physiol. 95: 623-627.

N'tchobo H., Dali N., Nguyen-Quoc B., Foyer C. H. and Yelle S. 1999. Starch synthesis in tomato remains constant throughout fruit development and is dependent on sucrose supply and sucrose activity. *J. Exp. Bot.* 50. 1457-1463.

Nguyen-Quoc, B. and C. H. Foyer. 2001. A role for 'futile cycles' involving invertase and sucrose synthase in sucrose metabolism of tomato fruit. *J. Exp. Bot.* 52:881-889.

Ohyama A., Ito H., Sato T., Nishimura S., Imai T. and Hirai M. 1995. Suppression of acid invertase activity by antisense RNA modifies the sugar composition of tomato fruit. *Plant Cell Physiol.* 36: 369-376.

Privat I., Eychenne M., Kandalaft L., Caillet C., Lin C., Tanksley S. and James McCarthy. 2005. Molecular characterization of sucrose synthase CcSS2 and sucrose phosphate synthase CcSPS1 genes: quantitative expression and enzymatic activity in low and high sucrose coffee varieties. Internal Report.

Rausch T. and Greiner S. 2004. Plant protein inhibitors of invertases. Biochimica et Biophysica Acta. 1696: 253-261.

Robinson N. L., Hewitt J. D. and Bennett A. B. 1998. Sink metabolism in tomato fruit. *Plant Physiol.* 87:732-730.

Rogers W. J., Michaux S., Bastin M. and P. Bucheli. 1999. Changes to the content of sugars, sugar alcohols, myo-inositol, carboxylic acids and inorganic anions in developing grains from different varieties of *Robusta* (*Coffea canephora*) and *Arabica* (*C. arabica*) coffees. *Plant Sc.* 149: 115-123.

Roitsch T. and Gonzalez M-C. 2004. Function and regulation of plant invertases: sweet sensations. *Trends in Plant Science.* 9 (12): 606-613.

Russwurm, H. 1969. Fractionation and analysis of aroma precursors in green coffee, ASIC 4: 103-107.

Scholes J., Bundock N., Wilde R. and Rolfe S. 1996. The impact of reduced vacuolar invertase activity on the photosynthetic and carbohydrate metabolism of tomato. *Planta.* 200: 265-272.

Scognamiglio M. A., Ciardiello M. A., Tamburrini M., Carratore V., Rausch T. and Camardella L. 2003. The plant invertase inhibitor shares structural properties and disulfide bridges arrangement with the pectin methylesterase inhibitor. Journal of Protein Chemistry. 22 (3):363-369.

Sturm A. Chrispeels M. J. 1990. cDNA cloning of carrot extracellular β-fructosidase and its expression in response to wounding and bacterial infection. *Plant Cell* 2: 1107-1119.

Sun J., Loboda T., Sung S. J. S, and Black, C. C. J. 1992. Sucrose synthase in wild tomato, *Lycopersicon chmielewskii*, and tomato fruit sink strength. *Plant Physiol.* 98: 1163-1169.

Tang G. Q., Luscher M. and Sturm A. 1999. Antisense repression of vacuolar and cell wall invertase in transgenic carrot alters early plant development and sucrose partitioning. *Plant Cell.* 11: 177-189.

Tanksley S. D., Grandillo T. M., Fulton T. M., Zamir D., Eshed Y., Petirad V., Lopez J. and Beck-Bunn T. 1996. Advanced backcross QTL analysis in a cross between an elite processing line of tomato and its wild relative *L. pimpinellifolium. Theor Appl Gene.* 92:213-224.

von Schaewen A., Stitt M., Schmidt R., Sonnewald U. and Willmitzer L. 1990. Expression of yeast-derived invertase in the cell wall of tobacco and *Arabidopsis* plants leads to accumulation of carbohydrate and inhibition of photosynthesis and strongly influences growth and phenotype of transgenic tobacco plants. *EMBO J.* 9: 3033-3044.

Wang F., Smith A. G. and Brenner M. L. 1993. Sucrose synthase starch accumulation and tomato fruit sink strength. *Plant Physiol* 101:321-327.

Weil M., Krausgrill S., Schuster A. and Rausch T. 1994. A 17 kDa *Nicotiana tabacum* cell-wall peptide acts as an in vitro inhibitor of the cell-wall isoform of acid invertase. *Planta.* 193: 438-445.

Yau Y-Y and Simon P. W. 2003. A 2.5 kb insert eliminates acid soluble invertase isozyme II transcript in carrot (*Daucus carota* L.) roots, causing high sucrose accumulation. *Plant Mol Biol.* 53: 151-162.

Yelle S., Chetelat R. T., Dorais M., Deverna J. W. and Bennett A. 1991. Sink metabolism in tomato fruit. Genetic and biochemical analysis of sucrose accumulation. *Plant Physiol.* 95: 1026-1036.

Ziegler H. 1975. Nature of transported substances. *Encyclopedia of Plant Physiology.* 25: 505-509:

Zrenner, R., Salanoubat, M., Willmitzer, L., and Sonnewald, U. 1995. Evidence of crucial role of sucrose synthase for sink strength using transgenic potato plants (*Solanum tuberosum* L.). *Plant J.* 7:97-107.

The present invention is not limited to the embodiments described and exemplified above, but is capable of variation and modification within the scope of the appended claims.

What is claimed is:

1. A nucleic acid molecule isolated from coffee comprising a coding sequence that encodes an invertase inhibitor, wherein the invertase inhibitor comprises an amino acid sequence that is 95% or more identical to that of SEQ ID NO: 14.

2. The nucleic acid molecule of claim 1, wherein the invertase inhibitor comprises the amino acid sequence of SEQ ID NO: 14.

3. A The coding sequence of the nucleic acid molecule of claim 1, contained within a vector.

4. The vector of claim 3, which is an expression vector selected from the group of vectors consisting of plasmid, phagemid, cosmid, baculovirus, bacmid, bacterial, yeast and viral vectors.

5. The vector of claim 3, wherein the coding sequence of the nucleic acid molecule is operably linked to a constitutive promoter, or an inducible promoter, or a tissue-specific promoter.

6. The vector of claim 5, wherein the tissue specific promoter is a seed specific promoter.

7. The vector of claim 6, wherein the seed specific promoter is a coffee seed specific promoter.

8. A host cell transformed with the vector of claim 3.

9. The host cell of claim 8, selected from the group consisting of plant cells, bacterial cells, fungal cells, insect cells and mammalian cells.

10. The host cell of claim 8, which is a plant cell selected from the group of plants consisting of coffee, tobacco, Arabidopsis, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, zinnia, and turfgrasses.

11. A fertile plant produced from the plant cell of claim 10.

12. A method of modulating flavor or aroma of coffee beans, the method comprising increasing expression of one or more invertase inhibitors within coffee seeds by introducing one or more transgenes encoding the one or more invertase inhibitors into a coffee plant, wherein the one or more invertase inhibitors comprise an amino acid sequence that is 95% or more identical to that of SEQ ID NO: 14.

13. The method of claim 12, wherein endogenous invertase activity in the plant is decreased as compared with an equivalent plant in which expression of the invertase inhibitor is not increased.

14. The method of claim 12, wherein the plant comprises more sucrose in its seeds than does an equivalent plant in which expression of the invertase inhibitor is not increased.

15. A method of modulating flavor or aroma of coffee beans, the method comprising decreasing expression of one or more endogenous invertase inhibitors, wherein said decreased expression is effectuated by one or both of RNAi and antisense suppression methods, and wherein the one or more endogenous invertase inhibitors comprise an amino acid sequence that is 95% or more identical to that of SEQ ID NO: 14.

16. The method of claim 15, wherein the plant comprises less sucrose in its seeds than does an equivalent plant in which expression of the endogenous invertase inhibitor is not decreased.

* * * * *

SEQUENCE LISTING

```
<160> NUMBER OF SEQ ID NOS: 78

<210> SEQ ID NO 1
<211> LENGTH: 1731
<212> TYPE: DNA
<213> ORGANISM: Coffea canephora
```

<400> SEQUENCE: 1

```
atggctagct tttacctctg gctaatgtgc ctgtgctgga tggtagtgct cggacatggc     60
attcttgaag cagaagcatc ccacggagtt tacagaaatc ttgcatctct tcaacctgca    120
tctccaagtc aaacttacag aacttcttat cacttccaac ctcccaagaa ctggatgaac    180
gatcctaatg gaccaacggt ttatagggga ctttaccatc tattctatca gtacaatcca    240
ctcggtccag attgggggaa cattgtttgg gctcactcca cctctaaaga tttaatcaac    300
tggaaccctc acaaagcagc catttttccg tctcagaagg gtgatgtgaa tggttgctgg    360
tcaggatcaa cgacaatgct tcgaggggaa aacccagcca ttctctacac tggcatagac    420
cctaagagcc agcaagttca aaatcttgct gtccccagaa atctttctga cccatacctg    480
atagaatggg tcaaatcgcc ttacaatcca ctgatgactc cgactccaga gaacaaaatc    540
gattcaagct cattcagaga cccaactact gcctggttgg gccctgatgg ccgatggaga    600
gtcatcgttg gaaataaatt aaatcgtcga ggaaaagcac ttctgtacag aagcaaggat    660
tttgttcgtt ggaccaaagc tcagcaccca ctgtattcaa tacaaggcac tggaatgtgg    720
gaatgccctg atttttaccc tgtttcgagc agccctattg gtttagacac atcaaccatt    780
ggcgaaggcg ttaaacatgt tcttaaggta agcctggatg acaccaagca cgatcagtac    840
gcgattggaa catatgtgca ttccaaggat gttttcgtgc cgaatgctgg agccgcagaa    900
aagttttcag gcttgagata cgattatggg aagtcctatg cttcaaaaac attctacgat    960
agtttgaaga agcgaagaat tctttggggt tggatcaacg agtcattatc tcgagaagat   1020
tatattgctc agggatggtc cggagttcag gcaattccta ggctggtatg gctagataaa   1080
tcaggaaaac aactggtcca gtggccaatt tcagagattg aaacgctacg acaaaaaaaa   1140
gttggctatc ctcttacgct gctcaagagc ggatccacac tagaagttca aggcatcaaa   1200
gctgcccaag cggacgtaga tgtgtcgttc caagtagcac cccagttgga gcaagctgat   1260
gcactcgacc caagttggac ggacccccaa ctgctgtgta gtcaaaaggg tgcatcagtc   1320
agaggaggga caggaccatt tggactaaaa gttttggctt caaaggatct gcaggaatat   1380
acggccgtct tctttagaat tttcaaagcc cggaacaaat atgtggtgct gatgtgcagt   1440
gatcagagca ggtcctcgct caatgaaaaa ccagataaga cgacttatgg ggcatttctg   1500
gacgtggatc ctttgcacga agaattatct ttgaggagct tgattgatca ttcaatagtg   1560
gaaagctttg gtggaaaggg caaggcatgc atcacttcaa gggtatatcc tactaaagct   1620
ttaggcaacg aggcacgctt gtacgtcttc aattatggaa aggccaacgt cgcaatctca   1680
agcatgaatg cttggaccat gaagaatgcc agtatcaatc gaaagaattg a            1731
```

<210> SEQ ID NO 2
<211> LENGTH: 2212
<212> TYPE: DNA
<213> ORGANISM: Coffea canephora

<400> SEQUENCE: 2

```
ctgaacttgc cgccgtctcc gatgctcctt tgctagagca atccgatgaa gcagaggttt     60
gtcggtcctc gggtcaaagt agacaacggc ccgttaaggt tctggccggc attttcctgt    120
cctcattgtt tctgcttacc ttaatcttga ccctttttcca aggacaagaa gaacctcgcg    180
atcaatctca aatgatcaat gccaatttaa acaagtcatc cccttcctca cctgtctccc    240
ctcattctct cattccagct tccagagggg ttcctcaagg agtctcggag aagactttcc    300
ggggagtctc tgatgcgaat gatgtctatc cttggaccaa tgctatgcta tcttggcaaa    360
```

```
gaacttccta ccatttccag ccggagaaga actggatgaa cgatcctaat ggtccattgt    420

tccacatggg ttggtaccac cttttctacc aatacaatcc ggattcagct atttggggaa    480

acatcacatg ggacatgcg gtttcaaggg accttattca ctggctgtat ctgcccttcg    540

ccatggtccc cgataggccg ttcgatatca acggtgtatg gaccggttca gccaccattc    600

ttcctggtgg tcaaatcgtg atcctgtaca ctggggacac tgctgatctg gtgcaggtgc    660

aaaaccttgc gtaccccgcc aacctatccg atcctctcct ccttgactgg atcaagtacc    720

cgggtaaccc ggtcatgatc cccccacctg gcattggcaa gaaggacttt agggaccccca    780

ccaccgcctg gctggcgccc gatgggacca agtggttggt tactctcggg tccaaggtca    840

ataaaacggg cattgccctg gtttatgaaa ccagcgactt caagggctac cggctcttgg    900

atggggtttt acacgcggtt ccccgcacag gcatgtggga gtgcgtggat ttctacccgg    960

tttccaccac gggggataat gggctggata catcggctaa tgggcctggc accaagcacg   1020

tcctgaaggc aagcttggac gagaacaagc acgattacta cgcactgggc acctatgatc   1080

cgaaaaacaa taagtggacc cctgacgatc cggaactgga tgtgggtatc gggttgcgtc   1140

tggactatgg caagtattac gcgtcaaaga cattttacga ccagaacaag aagaggagga   1200

ttttgtgggg ttggattgga gaaactgaca gcgaagctgc tgacctcatg aagggatggg   1260

catcggttca gacaatccca agaacggtgg tttttgacaa gaagactgga acaaacatac   1320

ttcaatggcc ggttgaagaa gcggagagct tgagatttaa tgctactgaa tttgacaccg   1380

tcaagctgga accaggatcc atcgcgcccc taaatattgg ctcagcaacg cagttagaca   1440

tcattgcttc atttgaagtg gatagtgagg cattggaggc gacagtagag gctgacgtgg   1500

ggtacaactg caccacaagt ggtggcgctg ccagcagggg aaagttggga cccttcggtc   1560

ttctagttct tgctgatggt tcactgtctg agctaacccc cgtctacttc tatatctcca   1620

aaagcactga tggtagtgca gagactcact tctgctctga cgaatcgagg tcttcaaagg   1680

cacctgatgt tgggaaacta gtttacggga gcacggttcc tgttcttgat ggtgaaaaat   1740

tgtcggcgcg gttactggtt gatcactccg tagtagaaag ctttgctcaa gggggaagaa   1800

gagtgattac ttcaagagtt tatccgacca aggcaatcta tggagcagcg cgactcttcc   1860

ttttcaacaa tgccacaggg gtgagtgtca ccgcatcagc aaagatttgg cacatgcgat   1920

cagcagacat tcgaaccttc ccagatttgt gaatgccatc caaatctctg gaaatacaat   1980

tgcttgttca ctcgggtggt tcccaagatt cggaatgaag gaaggaagaa ggccaagttc   2040

agaaaccctt tgtagcatag tgattaaaga gttcttgtac caaagcaaaa aaaaagaggg   2100

cgactcgcta ccatgaagca tctcagggtc tgggatattt atagcaaatt attcagtcac   2160

tgcttgtttg tatctatata cgtgatgcag cactgatatt tactcaaaaa aa           2212
```

<210> SEQ ID NO 3
<211> LENGTH: 1675
<212> TYPE: DNA
<213> ORGANISM: Coffea arabica

<400> SEQUENCE: 3

```
atggagtgtg ttagagaata tcaacttagg aatgttagct cgcattgttc tatctcggaa     60

atggatgatt atgatctctc aaagcttctt gataagccag ataaacccag attaaacata    120

gaaaggcaga gatcctttga tgagagatca ctgagtgagt tgtctattgg tttatctaga    180

gcgttagatg catatgaaac agcttattca ccaggccggt ctgcgttaga cactccggtt    240

tcatctgcga ggaattcctt tgagccccac cctatggttg ctgatgcttg ggaagctctc    300
```

```
cgcagatctt tggtgttttt ccgtgaccaa cctgttggca caatcgctgc atatgatcat    360

gcctctgagg aggttttaaa ctatgaccag gtttttgtac gagactttgt gccaagtgct    420

ctggcatttt taatgaatgg tgagcctgaa attgtaaaga attttctatt gaagacactt    480

cagcttcaag gctgggaaaa aagaattgat agatttaagc ttggggaagg ggccatgcca    540

gctagtttca aagttttaca cgacccagat cgtaagacag atacaatagt agctgatttt    600

ggtgagagtg caattggaag ggttgctcca gttgactctg gattttggtg gatcattctt    660

ctacgtgcgt atactaagtc tactggagac ctaagtctgg ctgaaacacc ggagtgccaa    720

aaagggatga ggcttatatt gagcttgtgt ttgtctgaag gatttgatac ttttccaact    780

ttactttgtg ctgatggatg ctccatgatt gatagaagaa tggggattta tggttatcct    840

attgaaatcc aagcactctt ctttatggca ctgagatgtg ccttggtgat gttgaggcat    900

gacacggaag ggaaagagtt cattgagaga atagtaaagc gcttgcatgc gttaagcttt    960

cacatgagaa gttatttctg gcttgacttc caacaattaa atgacatata tcgctataaa   1020

actgaagaat actcgcatac tgcagtaaat aagtttaatg ttattccaga ttcaatttta   1080

gattgggtgt ttgattttat gccaacacgt ggtggttatt tcattggcaa tgttagtcct   1140

gcaagaatgg atatgagatg gtttgcattg ggaaattgtg ttgctatttt atcttgtcta   1200

gctactgctg agcaagctgc tgctattatg gatcttatag aggctcgttg ggatgagctt   1260

gttggggaaa tgcctatgaa aatatgttat cctgcaatag aaagtcatga gtggagaatt   1320

gttactggct gtgatccaaa gaatacaaga tggagttacc acaatggtgg atcttggcca   1380

gtgcttttgt ggttgctaac ggctgcatgc atcaagaccg gacgaataca aattgctaga   1440

cgtgcaattg atcttgctga gagccttttg ctcaaggaca gttggcctga gtactatgat   1500

ggcaaacttg gtagatatat tggtaaacaa gctagaaagt tccagacatg gtcaatcgct   1560

ggatatctgg ttgcaaagat gatgttagag gatccttcac acttggggat gatttctctt   1620

gaagaagaca agcaaatgaa gcctctgatt aagatcctcc tcgtggacct gctga        1675
```

<210> SEQ ID NO 4
<211> LENGTH: 687
<212> TYPE: DNA
<213> ORGANISM: Coffea canephora

<400> SEQUENCE: 4

```
acatgatcgg catagacccg gaaatggttt actttatctg caattcatga actgaaacat     60

ctttttctcg ggtccctttt cctgagattt ttcctgggct agacaaaaaa cactcaaggg    120

atagatgttt ctgcgtttgc taccaagaag tggaaaactg aacatgtttc tgttcttcag    180

agtcagattt atgcttcact ttttcttttt ttcttttttt tctatagatt gaccattcga    240

tcattgaaag ttttggaggt gaaggaaaga cttgcatcac ttctagagtc tatccgacgt    300

tggcaattgg tcaggaatcc catctttatg tattcaacta tggcacagaa agcatcagaa    360

tctccaattt aagcgcttgg agcatgagga gagctcaatt tttccagtcg tccacaaagg    420

aagaaaagcc gaaattgatt gaggaataga tttttggcga tcaaattcaa tgcatgcttc    480

tgagctcctg ttgctttatg attccttcca atatcatcaa tcgcatcttt ggtaggatac    540

cagtatgtag ccaaggcatg atgaaattaa ttaatccagg gcaggtttgc taatagatac    600

attgcaatct gccactggtc tgtaatgacc tcctttgtta ctttttctgt tttattaatt    660

tttttaaat aacaaaacta atatttt                                          687
```

<210> SEQ ID NO 5
<211> LENGTH: 670
<212> TYPE: DNA
<213> ORGANISM: Coffea canephora

<400> SEQUENCE: 5

```
aaaacatgcc atattaaaca agaaaaatga ggccttccat ctcctctgcc ctcttgatca     60
ctttattcct cctgtgtttc atccatggag ccaccagcca agagaacctg atcagggaca    120
gttgcagaac atttgccaaa gatgatccaa acatcaactt caatttctgc acgacttctc    180
tccaagctgc accagctagc cactgtgctg ctcttcgcgg cctggggacg atttccttca    240
ggctgatccg gtacaacgtt actgatacaa ggtgcatgat cagacaattg ctcaagggca    300
agaagctgga tccttatgtc cggcagtgct tgaatgattg cttcgagctt tattcagatg    360
caatagacac tatgaagcag gccatgaaag cttacaatac taaaagattc gccgatgcta    420
atatagagat aagttcgatt atggatgcag cgacaacttg tgaagatggt ttcaatgaga    480
gaaaaggtgt actttcacca ttaacaaaga gaaataacaa caccttcgag ttgtctgcaa    540
tagcacttaa tgtcatgcgt attcttcaga cacggtcaga ctaatcttcc tggaatattg    600
aactactgcg taatattacc agttatcagg gtttctttct tgttaaaaaa aaaaaaaaaa    660
aaaaaaaaac                                                           670
```

<210> SEQ ID NO 6
<211> LENGTH: 629
<212> TYPE: DNA
<213> ORGANISM: Coffea canephora

<400> SEQUENCE: 6

```
caattttctc tcataaacag gatgagaaat ttcacttctt tcatgcttct ttttccttat     60
gcgctagttg ttctaaccat tgttccgcca ctaatctctt gcgatctcat ctctgaaaca    120
tgtgaccaaa ccccaaatga tcgcctttgt gttaaaattc tgaggaaaga caatcggagt    180
cttgatgcag atgttgccgg tctggccctg gtcgccgttg aggcagttag agacaaggca    240
aactcaacgt tgcaaagcat caaggagcta aaaaggtcta atctaacatt ggcaaatgcg    300
ctaatggaat gccaagaaaa ctactatgta atcctcagaa ttgatgttcc aaaagctgtg    360
ggatcaatga gagaaaaccc aagacttgct gaacatggga tggctgatgc tgttatagaa    420
gctcaggggt gtgaagcaag tttgaacaaa ctagagcagt caccactggc tgacgtgaac    480
gctgccgttt atgacctgtc tgttgtggct ctgtccataa tcaggataat gttgcataga    540
atctatactg ttaattagaa catggttgga ttcaatgaat aaaaaaatga tgattgacgt    600
ctaaaaaaaa aaaaaaaaaa aaaaaaaaa                                      629
```

<210> SEQ ID NO 7
<211> LENGTH: 704
<212> TYPE: DNA
<213> ORGANISM: Coffea canephora

<400> SEQUENCE: 7

```
ccttaagcag tggtaacaac gcagagtacg cggggattgc attcttggtt catcagcgtt     60
tggctggaca attttctctt cttccttgtg ctggaatggc ttcctttggt cgattttgct    120
tgttcgcctg gcttttgtgg ggaaacttag gagtccgagg cgatgactcg gcgatcgttg    180
gtgtatgcaa aaagattggc atttattatt atatgtgcta tgactgccta aagagcaacc    240
cacaagaacc agactttgct gccaaatcca taatctgcgc tactgatgca tatgttatca    300
tccgaaaatc agctttcgat ttttcgttga attctactgg ccgctttcgg gaggtggcca    360
```

```
aattgtgtgt ggatcaattt gacataactt tgggttactg caaagccgcg tttaaagcat    420

ggagattgaa gcgaaaacta gccaccttag catttcttca cagcggcttg gattattact    480

tcaagtgcgt tgatcacctc tccgaaccca ttccaaatga atatggcata caattagata    540

ctgctaaatc tttcaatgag gtgtcaatta aagtcgcctc tctaccatga tcatggtttt    600

gatccaaata ttggatagct aatgtaaaat atatcatctt aatcttcatg gactgcagtt    660

gatgcgtgtt tttcaaaaaa aaaaaaaaaa aaaaaaaaaa aagt                     704


<210> SEQ ID NO 8
<211> LENGTH: 640
<212> TYPE: DNA
<213> ORGANISM: Coffea canephora

<400> SEQUENCE: 8

gaaaagagag aaaaaaaatg gagttatctt ggagccatag atcgtcatat tttccattgc     60

ttttattttt cctagcattt ctgggctatt attcttcatg tggggaagca actcaagatc    120

taattgaacg tgtttgctct aaatcaaaag acccttcatt ttgtaccaaa gccttagagt    180

cagaccctcg ttctcgcact gcaaatcttg ccggcctctg ccaaatttcg attgatttat    240

caaccaccaa tgccaaatca acccaagccc tggtcacttc ccttggaaaa aaggcaactg    300

ataagatatc aaaagagata tacaatactt gcttggaaaa ctatacaaac agcatttccg    360

ttcttggtga ttgtaccaag cgattgcaag ctggtgatta tgcaggcgtg aatatcaaag    420

catcagcagc tcaaactgaa gttgatactt gtgatgaatg tttcaaggaa cgtaaactac    480

ctgaaccacc aacacttaca aatgcttgtc agaaagagca aaaactttgt aatattattt    540

tggttacagc aaatatgttg caaggaaatt aatatgtgaa aaaaagacat atttcttaaa    600

aaaaaaaaaa aaaaaaaaaa ataaaaaaaa aaaaaaaaaa                          640


<210> SEQ ID NO 9
<211> LENGTH: 576
<212> TYPE: PRT
<213> ORGANISM: Coffea canephora

<400> SEQUENCE: 9

Met Ala Ser Phe Tyr Leu Trp Leu Met Cys Leu Cys Trp Met Val Val
1               5                   10                  15

Leu Gly His Gly Ile Leu Glu Ala Glu Ala Ser His Gly Val Tyr Arg
            20                  25                  30

Asn Leu Ala Ser Leu Gln Pro Ala Ser Pro Ser Gln Thr Tyr Arg Thr
        35                  40                  45

Ser Tyr His Phe Gln Pro Pro Lys Asn Trp Met Asn Asp Pro Asn Gly
    50                  55                  60

Pro Thr Val Tyr Arg Gly Leu Tyr His Leu Phe Tyr Gln Tyr Asn Pro
65                  70                  75                  80

Leu Gly Pro Asp Trp Gly Asn Ile Val Trp Ala His Ser Thr Ser Lys
                85                  90                  95

Asp Leu Ile Asn Trp Asn Pro His Lys Ala Ala Ile Phe Pro Ser Gln
            100                 105                 110

Lys Gly Asp Val Asn Gly Cys Trp Ser Gly Ser Thr Thr Met Leu Arg
        115                 120                 125

Gly Glu Asn Pro Ala Ile Leu Tyr Thr Gly Ile Asp Pro Lys Ser Gln
    130                 135                 140

Gln Val Gln Asn Leu Ala Val Pro Arg Asn Leu Ser Asp Pro Tyr Leu
145                 150                 155                 160
```

```
Ile Glu Trp Val Lys Ser Pro Tyr Asn Pro Leu Met Thr Pro Thr Pro
                165                 170                 175

Glu Asn Lys Ile Asp Ser Ser Ser Phe Arg Asp Pro Thr Thr Ala Trp
            180                 185                 190

Leu Gly Pro Asp Gly Arg Trp Arg Val Ile Val Gly Asn Lys Leu Asn
        195                 200                 205

Arg Arg Gly Lys Ala Leu Leu Tyr Arg Ser Lys Asp Phe Val Arg Trp
    210                 215                 220

Thr Lys Ala Gln His Pro Leu Tyr Ser Ile Gln Gly Thr Gly Met Trp
225                 230                 235                 240

Glu Cys Pro Asp Phe Tyr Pro Val Ser Ser Ser Pro Ile Gly Leu Asp
                245                 250                 255

Thr Ser Thr Ile Gly Glu Gly Val Lys His Val Leu Lys Val Ser Leu
            260                 265                 270

Asp Asp Thr Lys His Asp Gln Tyr Ala Ile Gly Thr Tyr Val His Ser
        275                 280                 285

Lys Asp Val Phe Val Pro Asn Ala Gly Ala Ala Glu Lys Phe Ser Gly
    290                 295                 300

Leu Arg Tyr Asp Tyr Gly Lys Ser Tyr Ala Ser Lys Thr Phe Tyr Asp
305                 310                 315                 320

Ser Leu Lys Lys Arg Arg Ile Leu Trp Gly Trp Ile Asn Glu Ser Leu
                325                 330                 335

Ser Arg Glu Asp Tyr Ile Ala Gln Gly Trp Ser Gly Val Gln Ala Ile
            340                 345                 350

Pro Arg Leu Val Trp Leu Asp Lys Ser Gly Lys Gln Leu Val Gln Trp
        355                 360                 365

Pro Ile Ser Glu Ile Glu Thr Leu Arg Gln Lys Lys Val Gly Tyr Pro
    370                 375                 380

Leu Thr Leu Leu Lys Ser Gly Ser Thr Leu Glu Val Gln Gly Ile Lys
385                 390                 395                 400

Ala Ala Gln Ala Asp Val Asp Val Ser Phe Gln Val Ala Pro Gln Leu
                405                 410                 415

Glu Gln Ala Asp Ala Leu Asp Pro Ser Trp Thr Asp Pro Gln Leu Leu
            420                 425                 430

Cys Ser Gln Lys Gly Ala Ser Val Arg Gly Gly Thr Gly Pro Phe Gly
        435                 440                 445

Leu Lys Val Leu Ala Ser Lys Asp Leu Gln Glu Tyr Thr Ala Val Phe
    450                 455                 460

Phe Arg Ile Phe Lys Ala Arg Asn Lys Tyr Val Val Leu Met Cys Ser
465                 470                 475                 480

Asp Gln Ser Arg Ser Ser Leu Asn Glu Lys Pro Asp Lys Thr Thr Tyr
                485                 490                 495

Gly Ala Phe Leu Asp Val Asp Pro Leu His Glu Glu Leu Ser Leu Arg
            500                 505                 510

Ser Leu Ile Asp His Ser Ile Val Glu Ser Phe Gly Gly Lys Gly Lys
        515                 520                 525

Ala Cys Ile Thr Ser Arg Val Tyr Pro Thr Lys Ala Leu Gly Asn Glu
    530                 535                 540

Ala Arg Leu Tyr Val Phe Asn Tyr Gly Lys Ala Asn Val Ala Ile Ser
545                 550                 555                 560

Ser Met Asn Ala Trp Thr Met Lys Asn Ala Ser Ile Asn Arg Lys Asn
                565                 570                 575
```

<210> SEQ ID NO 10
<211> LENGTH: 586
<212> TYPE: PRT
<213> ORGANISM: Coffea canephora

<400> SEQUENCE: 10

```
Met Ile Asn Ala Asn Leu Asn Lys Ser Ser Pro Ser Ser Pro Val Ser
1               5                   10                  15

Pro His Ser Leu Ile Pro Ala Ser Arg Gly Val Pro Gln Gly Val Ser
            20                  25                  30

Glu Lys Thr Phe Arg Gly Val Ser Asp Ala Asn Asp Val Tyr Pro Trp
        35                  40                  45

Thr Asn Ala Met Leu Ser Trp Gln Arg Thr Ser Tyr His Phe Gln Pro
    50                  55                  60

Glu Lys Asn Trp Met Asn Asp Pro Asn Gly Pro Leu Phe His Met Gly
65                  70                  75                  80

Trp Tyr His Leu Phe Tyr Gln Tyr Asn Pro Asp Ser Ala Ile Trp Gly
                85                  90                  95

Asn Ile Thr Trp Gly His Ala Val Ser Arg Asp Leu Ile His Trp Leu
            100                 105                 110

Tyr Leu Pro Phe Ala Met Val Pro Asp Arg Pro Phe Asp Ile Asn Gly
        115                 120                 125

Val Trp Thr Gly Ser Ala Thr Ile Leu Pro Gly Gly Gln Ile Val Ile
    130                 135                 140

Leu Tyr Thr Gly Asp Thr Ala Asp Leu Val Gln Val Gln Asn Leu Ala
145                 150                 155                 160

Tyr Pro Ala Asn Leu Ser Asp Pro Leu Leu Leu Asp Trp Ile Lys Tyr
                165                 170                 175

Pro Gly Asn Pro Val Met Ile Pro Pro Pro Gly Ile Gly Lys Lys Asp
            180                 185                 190

Phe Arg Asp Pro Thr Thr Ala Trp Leu Ala Pro Asp Gly Thr Lys Trp
        195                 200                 205

Leu Val Thr Leu Gly Ser Lys Val Asn Lys Thr Gly Ile Ala Leu Val
    210                 215                 220

Tyr Glu Thr Ser Asp Phe Lys Gly Tyr Arg Leu Leu Asp Gly Val Leu
225                 230                 235                 240

His Ala Val Pro Arg Thr Gly Met Trp Glu Cys Val Asp Phe Tyr Pro
                245                 250                 255

Val Ser Thr Thr Gly Asp Asn Gly Leu Asp Thr Ser Ala Asn Gly Pro
            260                 265                 270

Gly Thr Lys His Val Leu Lys Ala Ser Leu Asp Glu Asn Lys His Asp
        275                 280                 285

Tyr Tyr Ala Leu Gly Thr Tyr Asp Pro Lys Asn Asn Lys Trp Thr Pro
    290                 295                 300

Asp Asp Pro Glu Leu Asp Val Gly Ile Gly Leu Arg Leu Asp Tyr Gly
305                 310                 315                 320

Lys Tyr Tyr Ala Ser Lys Thr Phe Tyr Asp Gln Asn Lys Lys Arg Arg
                325                 330                 335

Ile Leu Trp Gly Trp Ile Gly Glu Thr Asp Ser Glu Ala Ala Asp Leu
            340                 345                 350

Met Lys Gly Trp Ala Ser Val Gln Thr Ile Pro Arg Thr Val Val Phe
        355                 360                 365

Asp Lys Lys Thr Gly Thr Asn Ile Leu Gln Trp Pro Val Glu Glu Ala
    370                 375                 380

Glu Ser Leu Arg Phe Asn Ala Thr Glu Phe Asp Thr Val Lys Leu Glu
```

```
385                 390                 395                 400

Pro Gly Ser Ile Ala Pro Leu Asn Ile Gly Ser Ala Thr Gln Leu Asp
                405                 410                 415

Ile Ile Ala Ser Phe Glu Val Asp Ser Glu Ala Leu Glu Ala Thr Val
            420                 425                 430

Glu Ala Asp Val Gly Tyr Asn Cys Thr Thr Ser Gly Gly Ala Ala Ser
        435                 440                 445

Arg Gly Lys Leu Gly Pro Phe Gly Leu Leu Val Leu Ala Asp Gly Ser
    450                 455                 460

Leu Ser Glu Leu Thr Pro Val Tyr Phe Tyr Ile Ser Lys Ser Thr Asp
465                 470                 475                 480

Gly Ser Ala Glu Thr His Phe Cys Ser Asp Glu Ser Arg Ser Ser Lys
                485                 490                 495

Ala Pro Asp Val Gly Lys Leu Val Tyr Gly Ser Thr Val Pro Val Leu
            500                 505                 510

Asp Gly Glu Lys Leu Ser Ala Arg Leu Leu Val Asp His Ser Val Val
        515                 520                 525

Glu Ser Phe Ala Gln Gly Gly Arg Arg Val Ile Thr Ser Arg Val Tyr
    530                 535                 540

Pro Thr Lys Ala Ile Tyr Gly Ala Ala Arg Leu Phe Leu Phe Asn Asn
545                 550                 555                 560

Ala Thr Gly Val Ser Val Thr Ala Ser Ala Lys Ile Trp His Met Arg
                565                 570                 575

Ser Ala Asp Ile Arg Thr Phe Pro Asp Leu
            580                 585


<210> SEQ ID NO 11
<211> LENGTH: 558
<212> TYPE: PRT
<213> ORGANISM: Coffea arabica

<400> SEQUENCE: 11

Met Glu Cys Val Arg Glu Tyr Gln Leu Arg Asn Val Ser Ser His Cys
1               5                   10                  15

Ser Ile Ser Glu Met Asp Asp Tyr Asp Leu Ser Lys Leu Leu Asp Lys
            20                  25                  30

Pro Asp Lys Pro Arg Leu Asn Ile Glu Arg Gln Arg Ser Phe Asp Glu
        35                  40                  45

Arg Ser Leu Ser Glu Leu Ser Ile Gly Leu Ser Arg Ala Leu Asp Ala
    50                  55                  60

Tyr Glu Thr Ala Tyr Ser Pro Gly Arg Ser Ala Leu Asp Thr Pro Val
65                  70                  75                  80

Ser Ser Ala Arg Asn Ser Phe Glu Pro His Pro Met Val Ala Asp Ala
                85                  90                  95

Trp Glu Ala Leu Arg Arg Ser Leu Val Phe Phe Arg Asp Gln Pro Val
            100                 105                 110

Gly Thr Ile Ala Ala Tyr Asp His Ala Ser Glu Glu Val Leu Asn Tyr
        115                 120                 125

Asp Gln Val Phe Val Arg Asp Phe Val Pro Ser Ala Leu Ala Phe Leu
    130                 135                 140

Met Asn Gly Glu Pro Glu Ile Val Lys Asn Phe Leu Leu Lys Thr Leu
145                 150                 155                 160

Gln Leu Gln Gly Trp Glu Lys Arg Ile Asp Arg Phe Lys Leu Gly Glu
                165                 170                 175

Gly Ala Met Pro Ala Ser Phe Lys Val Leu His Asp Pro Asp Arg Lys
```

```
            180                 185                 190

Thr Asp Thr Ile Val Ala Asp Phe Gly Glu Ser Ala Ile Gly Arg Val
        195                 200                 205

Ala Pro Val Asp Ser Gly Phe Trp Trp Ile Ile Leu Leu Arg Ala Tyr
    210                 215                 220

Thr Lys Ser Thr Gly Asp Leu Ser Leu Ala Glu Thr Pro Glu Cys Gln
225                 230                 235                 240

Lys Gly Met Arg Leu Ile Leu Ser Leu Cys Leu Ser Glu Gly Phe Asp
                245                 250                 255

Thr Phe Pro Thr Leu Leu Cys Ala Asp Gly Cys Ser Met Ile Asp Arg
            260                 265                 270

Arg Met Gly Ile Tyr Gly Tyr Pro Ile Glu Ile Gln Ala Leu Phe Phe
        275                 280                 285

Met Ala Leu Arg Cys Ala Leu Val Met Leu Arg His Asp Thr Glu Gly
    290                 295                 300

Lys Glu Phe Ile Glu Arg Ile Val Lys Arg Leu His Ala Leu Ser Phe
305                 310                 315                 320

His Met Arg Ser Tyr Phe Trp Leu Asp Phe Gln Gln Leu Asn Asp Ile
                325                 330                 335

Tyr Arg Tyr Lys Thr Glu Glu Tyr Ser His Thr Ala Val Asn Lys Phe
            340                 345                 350

Asn Val Ile Pro Asp Ser Ile Leu Asp Trp Val Phe Asp Phe Met Pro
        355                 360                 365

Thr Arg Gly Gly Tyr Phe Ile Gly Asn Val Ser Pro Ala Arg Met Asp
    370                 375                 380

Met Arg Trp Phe Ala Leu Gly Asn Cys Val Ala Ile Leu Ser Cys Leu
385                 390                 395                 400

Ala Thr Ala Glu Gln Ala Ala Ala Ile Met Asp Leu Ile Glu Ala Arg
                405                 410                 415

Trp Asp Glu Leu Val Gly Glu Met Pro Met Lys Ile Cys Tyr Pro Ala
            420                 425                 430

Ile Glu Ser His Glu Trp Arg Ile Val Thr Gly Cys Asp Pro Lys Asn
        435                 440                 445

Thr Arg Trp Ser Tyr His Asn Gly Gly Ser Trp Pro Val Leu Leu Trp
    450                 455                 460

Leu Leu Thr Ala Ala Cys Ile Lys Thr Gly Arg Ile Gln Ile Ala Arg
465                 470                 475                 480

Arg Ala Ile Asp Leu Ala Glu Ser Leu Leu Leu Lys Asp Ser Trp Pro
                485                 490                 495

Glu Tyr Tyr Asp Gly Lys Leu Gly Arg Tyr Ile Gly Lys Gln Ala Arg
            500                 505                 510

Lys Phe Gln Thr Trp Ser Ile Ala Gly Tyr Leu Val Ala Lys Met Met
        515                 520                 525

Leu Glu Asp Pro Ser His Leu Gly Met Ile Ser Leu Glu Glu Asp Lys
    530                 535                 540

Gln Met Lys Pro Leu Ile Lys Ile Leu Leu Val Asp Leu Leu
545                 550                 555

<210> SEQ ID NO 12
<211> LENGTH: 73
<212> TYPE: PRT
<213> ORGANISM: Coffea canephora

<400> SEQUENCE: 12

Ile Asp His Ser Ile Ile Glu Ser Phe Gly Gly Glu Gly Lys Thr Cys
```

```
1               5                   10                  15

Ile Thr Ser Arg Val Tyr Pro Thr Leu Ala Ile Gly Gln Glu Ser His
            20                  25                  30

Leu Tyr Val Phe Asn Tyr Gly Thr Glu Ser Ile Arg Ile Ser Asn Leu
        35                  40                  45

Ser Ala Trp Ser Met Arg Arg Ala Gln Phe Phe Gln Ser Ser Thr Lys
    50                  55                  60

Glu Glu Lys Pro Lys Leu Ile Glu Glu
65                  70


<210> SEQ ID NO 13
<211> LENGTH: 178
<212> TYPE: PRT
<213> ORGANISM: Coffea canephora

<400> SEQUENCE: 13

Met Arg Asn Phe Thr Ser Phe Met Leu Leu Phe Pro Tyr Ala Leu Val
1               5                   10                  15

Val Leu Thr Ile Val Pro Pro Leu Ile Ser Cys Asp Leu Ile Ser Glu
            20                  25                  30

Thr Cys Asp Gln Thr Pro Asn Asp Arg Leu Cys Val Lys Ile Leu Arg
        35                  40                  45

Lys Asp Asn Arg Ser Leu Asp Ala Asp Val Ala Gly Leu Ala Leu Val
    50                  55                  60

Ala Val Glu Ala Val Arg Asp Lys Ala Asn Ser Thr Leu Gln Ser Ile
65                  70                  75                  80

Lys Glu Leu Lys Arg Ser Asn Leu Thr Leu Ala Asn Ala Leu Met Glu
                85                  90                  95

Cys Gln Glu Asn Tyr Tyr Val Ile Leu Arg Ile Asp Val Pro Lys Ala
            100                 105                 110

Val Gly Ser Met Arg Glu Asn Pro Arg Leu Ala Glu His Gly Met Ala
        115                 120                 125

Asp Ala Val Ile Glu Ala Gln Gly Cys Glu Ala Ser Leu Asn Lys Leu
    130                 135                 140

Glu Gln Ser Pro Leu Ala Asp Val Asn Ala Ala Val Tyr Asp Leu Ser
145                 150                 155                 160

Val Val Ala Leu Ser Ile Ile Arg Ile Met Leu His Arg Ile Tyr Thr
                165                 170                 175

Val Asn


<210> SEQ ID NO 14
<211> LENGTH: 185
<212> TYPE: PRT
<213> ORGANISM: Coffea canephora

<400> SEQUENCE: 14

Met Arg Pro Ser Ile Ser Ser Ala Leu Leu Ile Thr Leu Phe Leu Leu
1               5                   10                  15

Cys Phe Ile His Gly Ala Thr Ser Gln Glu Asn Leu Ile Arg Asp Ser
            20                  25                  30

Cys Arg Thr Phe Ala Lys Asp Asp Pro Asn Ile Asn Phe Asn Phe Cys
        35                  40                  45

Thr Thr Ser Leu Gln Ala Ala Pro Ala Ser His Cys Ala Ala Leu Arg
    50                  55                  60

Gly Leu Gly Thr Ile Ser Phe Arg Leu Ile Arg Tyr Asn Val Thr Asp
65                  70                  75                  80
```

```
Thr Arg Cys Met Ile Arg Gln Leu Leu Lys Gly Lys Lys Leu Asp Pro
                85                  90                  95

Tyr Val Arg Gln Cys Leu Asn Asp Cys Phe Glu Leu Tyr Ser Asp Ala
            100                 105                 110

Ile Asp Thr Met Lys Gln Ala Met Lys Ala Tyr Asn Thr Lys Arg Phe
        115                 120                 125

Ala Asp Ala Asn Ile Glu Ile Ser Ser Ile Met Asp Ala Ala Thr Thr
    130                 135                 140

Cys Glu Asp Gly Phe Asn Glu Arg Lys Gly Val Leu Ser Pro Leu Thr
145                 150                 155                 160

Lys Arg Asn Asn Asn Thr Phe Glu Leu Ser Ala Ile Ala Leu Asn Val
                165                 170                 175

Met Arg Ile Leu Gln Thr Arg Ser Asp
            180                 185


<210> SEQ ID NO 15
<211> LENGTH: 164
<212> TYPE: PRT
<213> ORGANISM: Coffea canephora

<400> SEQUENCE: 15

Met Ala Ser Phe Gly Arg Phe Cys Leu Phe Ala Trp Leu Leu Trp Gly
1               5                   10                  15

Asn Leu Gly Val Arg Gly Asp Asp Ser Ala Ile Val Gly Val Cys Lys
            20                  25                  30

Lys Ile Gly Ile Tyr Tyr Tyr Met Cys Tyr Asp Cys Leu Lys Ser Asn
        35                  40                  45

Pro Gln Glu Pro Asp Phe Ala Ala Lys Ser Ile Ile Cys Ala Thr Asp
    50                  55                  60

Ala Tyr Val Ile Ile Arg Lys Ser Ala Phe Asp Phe Ser Leu Asn Ser
65                  70                  75                  80

Thr Gly Arg Phe Arg Glu Val Ala Lys Leu Cys Val Asp Gln Phe Asp
                85                  90                  95

Ile Thr Leu Gly Tyr Cys Lys Ala Ala Phe Lys Ala Trp Arg Leu Lys
            100                 105                 110

Arg Lys Leu Ala Thr Leu Ala Phe Leu His Ser Gly Leu Asp Tyr Tyr
        115                 120                 125

Phe Lys Cys Val Asp His Leu Ser Glu Pro Ile Pro Asn Glu Tyr Gly
    130                 135                 140

Ile Gln Leu Asp Thr Ala Lys Ser Phe Asn Glu Val Ser Ile Lys Val
145                 150                 155                 160

Ala Ser Leu Pro


<210> SEQ ID NO 16
<211> LENGTH: 184
<212> TYPE: PRT
<213> ORGANISM: Coffea canephora

<400> SEQUENCE: 16

Met Glu Leu Ser Trp Ser His Arg Ser Ser Tyr Phe Pro Leu Leu Leu
1               5                   10                  15

Phe Phe Leu Ala Phe Leu Gly Tyr Tyr Ser Ser Cys Gly Glu Ala Thr
            20                  25                  30

Gln Asp Leu Ile Glu Arg Val Cys Ser Lys Ser Lys Asp Pro Ser Phe
        35                  40                  45

Cys Thr Lys Ala Leu Glu Ser Asp Pro Arg Ser Arg Thr Ala Asn Leu
    50                  55                  60
```

```
Ala Gly Leu Cys Gln Ile Ser Ile Asp Leu Ser Thr Thr Asn Ala Lys
65                  70                  75                  80

Ser Thr Gln Ala Leu Val Thr Ser Leu Gly Lys Lys Ala Thr Asp Lys
                85                  90                  95

Ile Ser Lys Glu Ile Tyr Asn Thr Cys Leu Glu Asn Tyr Thr Asn Ser
            100                 105                 110

Ile Ser Val Leu Gly Asp Cys Thr Lys Arg Leu Gln Ala Gly Asp Tyr
        115                 120                 125

Ala Gly Val Asn Ile Lys Ala Ser Ala Ala Gln Thr Glu Val Asp Thr
    130                 135                 140

Cys Asp Glu Cys Phe Lys Glu Arg Lys Leu Pro Glu Pro Pro Thr Leu
145                 150                 155                 160

Thr Asn Ala Cys Gln Lys Glu Gln Lys Leu Cys Asn Ile Ile Leu Val
                165                 170                 175

Thr Ala Asn Met Leu Gln Gly Asn
            180


<210> SEQ ID NO 17
<211> LENGTH: 636
<212> TYPE: PRT
<213> ORGANISM: Lycopersicon esculentum

<400> SEQUENCE: 17

Met Ala Thr Gln Cys Tyr Asp Pro Glu Asn Ser Ala Ser Arg Tyr Thr
1               5                   10                  15

Leu Leu Pro Asp Gln Pro Asp Ser Gly His Arg Lys Ser Leu Lys Ile
            20                  25                  30

Ile Ser Gly Ile Phe Leu Ser Val Phe Leu Leu Leu Ser Val Ala Phe
        35                  40                  45

Phe Pro Ile Leu Asn Asn Gln Ser Pro Asp Leu Gln Ile Asp Ser Arg
    50                  55                  60

Ser Pro Ala Pro Pro Ser Arg Gly Val Ser Gln Gly Val Ser Asp Lys
65                  70                  75                  80

Thr Phe Arg Asp Val Ala Gly Ala Ser His Val Ser Tyr Ala Trp Ser
                85                  90                  95

Asn Ala Met Leu Ser Trp Gln Arg Thr Ala Tyr His Phe Gln Pro Gln
            100                 105                 110

Lys Asn Trp Met Asn Asp Pro Asn Gly Pro Leu Tyr His Lys Gly Trp
        115                 120                 125

Tyr His Leu Phe Tyr Gln Tyr Asn Pro Asp Ser Ala Ile Trp Gly Asn
    130                 135                 140

Ile Thr Trp Gly His Ala Val Ser Lys Asp Leu Ile His Trp Leu Tyr
145                 150                 155                 160

Leu Pro Phe Ala Met Val Pro Asp Gln Trp Tyr Asp Ile Asn Gly Val
                165                 170                 175

Trp Thr Gly Ser Ala Thr Ile Leu Pro Asp Gly Gln Ile Met Met Leu
            180                 185                 190

Tyr Thr Gly Asp Thr Asp Asp Tyr Val Gln Val Gln Asn Leu Ala Tyr
        195                 200                 205

Pro Ala Asn Leu Ser Asp Pro Leu Leu Leu Asp Trp Val Lys Phe Lys
    210                 215                 220

Gly Asn Pro Val Leu Val Pro Pro Pro Gly Ile Gly Val Lys Asp Phe
225                 230                 235                 240

Arg Asp Pro Thr Thr Ala Trp Thr Gly Pro Gln Asn Gly Gln Trp Leu
                245                 250                 255
```

```
Leu Thr Ile Gly Ser Lys Ile Gly Lys Thr Gly Val Ala Leu Val Tyr
            260                 265                 270

Glu Thr Ser Asn Phe Thr Ser Phe Lys Leu Leu Asp Gly Val Leu His
        275                 280                 285

Ala Val Pro Gly Thr Gly Met Trp Glu Cys Val Asp Phe Tyr Pro Val
    290                 295                 300

Ser Thr Lys Lys Thr Asn Gly Leu Asp Thr Ser Tyr Asn Gly Pro Gly
305                 310                 315                 320

Val Lys His Val Leu Lys Ala Ser Leu Asp Asp Asn Lys Gln Asp His
                325                 330                 335

Tyr Ala Ile Gly Thr Tyr Asp Leu Gly Lys Asn Lys Trp Thr Pro Asp
            340                 345                 350

Asn Pro Glu Leu Asp Cys Gly Ile Gly Leu Arg Leu Asp Tyr Gly Lys
        355                 360                 365

Tyr Tyr Ala Ser Lys Thr Phe Tyr Asp Pro Lys Lys Glu Arg Arg Val
    370                 375                 380

Leu Trp Gly Trp Ile Gly Glu Thr Asp Ser Glu Ser Ala Asp Leu Gln
385                 390                 395                 400

Lys Gly Trp Ala Ser Val Gln Ser Ile Pro Arg Thr Val Leu Tyr Asp
                405                 410                 415

Lys Lys Thr Gly Thr His Leu Leu Gln Trp Pro Val Glu Glu Ile Glu
            420                 425                 430

Ser Leu Arg Val Gly Asp Pro Thr Val Lys Gln Val Asp Leu Gln Pro
        435                 440                 445

Gly Ser Ile Glu Leu Leu Arg Val Asp Ser Ala Ala Glu Leu Asp Ile
    450                 455                 460

Glu Ala Ser Phe Glu Val Asp Lys Val Ala Leu Gln Gly Ile Ile Glu
465                 470                 475                 480

Ala Asp His Val Gly Phe Ser Cys Ser Thr Ser Gly Gly Ala Ala Ser
                485                 490                 495

Arg Gly Ile Leu Gly Pro Phe Gly Val Ile Val Ile Ala Asp Gln Thr
            500                 505                 510

Leu Ser Glu Leu Thr Pro Val Tyr Phe Tyr Ile Ser Lys Gly Ala Asp
        515                 520                 525

Gly Arg Ala Glu Thr His Phe Cys Ala Asp Gln Thr Arg Ser Ser Glu
    530                 535                 540

Ala Pro Gly Val Gly Lys Gln Val Tyr Gly Ser Ser Val Pro Val Leu
545                 550                 555                 560

Asp Gly Glu Lys His Ser Met Arg Leu Leu Val Asp His Ser Ile Val
                565                 570                 575

Glu Ser Phe Ala Gln Gly Gly Arg Thr Val Ile Thr Ser Arg Ile Tyr
            580                 585                 590

Pro Thr Lys Ala Val Asn Gly Ala Ala Arg Leu Phe Val Phe Asn Asn
        595                 600                 605

Ala Thr Gly Ala Ser Val Thr Ala Ser Val Lys Ile Trp Ser Leu Glu
    610                 615                 620

Ser Ala Asn Ile Gln Ser Phe Pro Leu Gln Asp Leu
625                 630                 635


<210> SEQ ID NO 18
<211> LENGTH: 650
<212> TYPE: PRT
<213> ORGANISM: Daucus carota

<400> SEQUENCE: 18
```

```
Met Glu His Pro Ile Thr Ile Ser His Tyr Thr Pro Leu Pro Asp Gly
1               5                   10                  15

Glu His Ser Pro Ser Leu Thr Thr Thr Asn Thr Ala Glu Gln Ser Ser
            20                  25                  30

Arg Arg Arg Ser Leu Thr Phe Val Leu Leu Phe Ser Ser Ile Leu Ala
        35                  40                  45

Ala Cys Leu Val Met Gly Thr Met Val Leu Phe Pro Asn Ser Gly Asn
    50                  55                  60

Glu Ala Val Glu Lys Ser Thr Val Val Pro Glu Glu Thr Val Glu Val
65                  70                  75                  80

Ala Pro Arg Gly Val Ala Glu Gly Val Ser Met Lys Ser Phe Arg Arg
                85                  90                  95

Pro Ala Leu Asn Ala Glu Pro Pro Ala Asn Phe Pro Trp Asn Ser Asn
            100                 105                 110

Val Leu Ser Trp Gln Arg Ser Ser Phe His Phe Gln Pro Asn Gln Asn
        115                 120                 125

Trp Met Asn Asp Pro Asn Gly Pro Leu Phe Tyr Lys Gly Trp Tyr His
    130                 135                 140

Leu Phe Tyr Gln Tyr Asn Pro Asp Gly Ala Ile Trp Gly Asn Lys Ile
145                 150                 155                 160

Val Trp Gly His Ala Val Ser Ser Asp Leu Ile His Trp Lys His Leu
                165                 170                 175

Pro Val Ala Met Val Thr Asp His Trp Tyr Asp Val Asn Gly Val Trp
            180                 185                 190

Thr Gly Ser Ala Thr Ile Leu Pro Asp Gly Gln Ile Val Met Leu Tyr
        195                 200                 205

Thr Gly Ser Thr Asn Glu Ser Val Gln Val Gln Asn Leu Ala Tyr Pro
    210                 215                 220

Ala Asp Pro Ser Asp Pro Leu Leu Ile Glu Trp Val Lys Tyr Pro Gly
225                 230                 235                 240

Asn Pro Val Leu Val Pro Pro Pro Gly Ile Asp Phe Lys Asp Phe Arg
                245                 250                 255

Asp Pro Thr Thr Ala Trp Arg Thr Pro Glu Gly Lys Trp Arg Leu Ile
            260                 265                 270

Ile Gly Ser Lys Leu Asn Lys Thr Gly Ile Ser Leu Val Tyr Asp Thr
        275                 280                 285

Val Asp Phe Lys Asn Phe Thr Leu Leu Asp Gly Val Leu His Ala Val
    290                 295                 300

His Gly Thr Gly Met Trp Glu Cys Val Asp Phe Tyr Pro Val Ser Lys
305                 310                 315                 320

Phe Gly Glu Asn Gly Leu Asp Thr Ser Phe Asp Gly Val Gly Val Lys
                325                 330                 335

His Val Met Lys Ala Ser Leu Asp Asp Asp Arg Asn Asp Tyr Tyr Ala
            340                 345                 350

Ile Gly Thr Tyr Asp Pro Val Ser Gly Lys Trp Val Pro Asp Asn Pro
        355                 360                 365

Glu Leu Asp Val Gly Ile Gly Leu Arg Tyr Asp Tyr Gly Ile Tyr Tyr
    370                 375                 380

Ala Ser Lys Thr Phe Tyr Asp Ser Asn Lys Lys Arg Arg Val Leu Trp
385                 390                 395                 400

Ser Trp Ile Lys Glu Thr Asp Ser Glu Ile Ser Asp Val Arg Lys Gly
                405                 410                 415

Trp Ala Ser Val Gln Gly Ile Pro Arg Thr Ile Leu Phe Asp Pro Lys
```

```
            420                 425                 430

Thr Gly Ser Asn Leu Leu Gln Trp Pro Val Glu Glu Val Asn Lys Leu
        435                 440                 445

Arg Leu Asn Lys Thr Val Phe Glu Asn Val Glu Ile Asn Thr Gly Ala
    450                 455                 460

Val Leu Pro Leu Glu Ile Gly Ser Gly Ser Gln Leu Asp Ile Thr Ala
465                 470                 475                 480

Glu Phe Glu Val Asp Lys Glu Ser Leu Glu Arg Val Gln Glu Thr Asn
                485                 490                 495

Glu Val Tyr Asp Cys Lys Asn Asn Gly Gly Ser Ser Gly Arg Gly Ala
            500                 505                 510

Leu Gly Pro Phe Gly Leu Leu Ile Leu Ala Asp Lys Asp Leu Ser Glu
        515                 520                 525

Gln Thr Pro Val Tyr Phe Tyr Ile Ala Lys Gly Ser Gly Gly Asn Leu
    530                 535                 540

Arg Thr Phe Phe Cys Ala Asp His Ser Arg Ser Ser Lys Ala Val Asp
545                 550                 555                 560

Val Asp Lys Glu Ile Tyr Gly Ser Val Val Pro Val Leu Arg Gly Glu
                565                 570                 575

Lys Leu Thr Met Arg Ile Leu Val Asp His Ser Ile Val Glu Ser Phe
            580                 585                 590

Ser Gln Gly Gly Arg Thr Cys Ile Thr Ser Arg Val Tyr Pro Thr Lys
        595                 600                 605

Ala Ile Tyr Asn Asn Ala Lys Val Phe Leu Phe Asn Asn Ala Thr Glu
    610                 615                 620

Ala Arg Ile Ile Ala Ser Leu Asn Ile Trp Gln Met Asn Thr Ala Gln
625                 630                 635                 640

Arg Gln Thr His Phe Ala Asp Leu Val Ile
                645                 650


<210> SEQ ID NO 19
<211> LENGTH: 639
<212> TYPE: PRT
<213> ORGANISM: Solanum tuberosum

<400> SEQUENCE: 19

Met Ala Thr Gln Tyr His Ser Ser Tyr Asp Pro Glu Asn Ser Ala Ser
1               5                   10                  15

His Tyr Thr Phe Leu Pro Asp Gln Pro Asp Ser Gly His Arg Lys Ser
            20                  25                  30

Leu Lys Ile Ile Ser Gly Ile Phe Leu Ser Ser Phe Leu Leu Leu Ser
        35                  40                  45

Val Ala Phe Phe Pro Ile Leu Asn Asn Gln Ser Pro Asp Leu Gln Ser
    50                  55                  60

Asn Ser Arg Ser Pro Ala Pro Pro Ser Arg Gly Val Ser Gln Gly Val
65                  70                  75                  80

Ser Asp Lys Thr Phe Arg Asp Val Val Asn Ala Ser His Ile Ser Tyr
                85                  90                  95

Ala Trp Ser Asn Ala Met Leu Ser Trp Gln Arg Thr Ala Tyr His Phe
            100                 105                 110

Gln Pro Gln Lys Asn Trp Met Asn Asp Pro Asn Gly Pro Leu Tyr His
        115                 120                 125

Lys Gly Trp Tyr His Leu Phe Tyr Gln Tyr Asn Pro Asp Ser Ala Ile
    130                 135                 140

Trp Gly Asn Ile Thr Trp Gly His Ala Val Ser Lys Asp Leu Ile His
```

-continued

```
145                 150                 155                 160

Trp Leu Tyr Leu Pro Phe Ala Met Val Pro Asp Gln Trp Tyr Asp Ile
                165                 170                 175

Asn Gly Val Trp Thr Gly Ser Ala Thr Ile Leu Pro Asp Gly Gln Ile
            180                 185                 190

Met Met Leu Tyr Thr Gly Asp Thr Asp Asp Tyr Val Gln Val Gln Asn
        195                 200                 205

Leu Ala Tyr Pro Thr Asn Leu Ser Asp Pro Leu Leu Leu Asp Trp Val
    210                 215                 220

Lys Tyr Lys Gly Asn Pro Val Leu Val Pro Pro Pro Gly Ile Gly Val
225                 230                 235                 240

Lys Asp Phe Arg Asp Pro Thr Thr Ala Trp Thr Gly Pro Gln Asn Gly
                245                 250                 255

Gln Trp Leu Leu Thr Ile Gly Ser Lys Ile Gly Lys Thr Gly Ile Ala
            260                 265                 270

Leu Val Tyr Glu Thr Ser Asn Phe Thr Ser Phe Lys Leu Leu Gly Glu
        275                 280                 285

Val Leu His Ala Val Pro Gly Thr Gly Met Trp Glu Cys Val Asp Phe
    290                 295                 300

Tyr Pro Val Ser Thr Glu Lys Thr Asn Gly Leu Asp Thr Ser Tyr Asn
305                 310                 315                 320

Gly Pro Gly Val Lys His Val Leu Lys Ala Ser Leu Asp Asp Asn Lys
                325                 330                 335

Gln Asp His Tyr Ala Ile Gly Thr Tyr Asp Leu Thr Lys Asn Lys Trp
            340                 345                 350

Thr Pro Asp Asn Pro Glu Leu Asp Cys Gly Ile Gly Leu Lys Leu Asp
        355                 360                 365

Tyr Gly Lys Tyr Tyr Ala Ser Lys Thr Phe Tyr Asp Pro Lys Lys Gln
    370                 375                 380

Arg Arg Val Leu Trp Gly Trp Ile Gly Glu Thr Asp Ser Glu Ser Ala
385                 390                 395                 400

Asp Leu Gln Lys Gly Trp Ala Ser Val Gln Ser Ile Pro Arg Thr Val
                405                 410                 415

Leu Tyr Asp Lys Lys Thr Gly Thr His Leu Leu Gln Trp Pro Val Glu
            420                 425                 430

Glu Ile Glu Ser Leu Arg Ala Gly Asp Pro Ile Val Lys Gln Val Asn
        435                 440                 445

Leu Gln Pro Gly Ser Ile Glu Leu Leu His Val Asp Ser Ala Ala Glu
    450                 455                 460

Leu Asp Ile Glu Ala Ser Phe Glu Val Asp Lys Val Ala Leu Gln Gly
465                 470                 475                 480

Ile Ile Glu Ala Asp His Val Gly Phe Ser Cys Ser Thr Ser Gly Gly
                485                 490                 495

Ala Ala Ser Arg Gly Ile Leu Gly Pro Phe Gly Val Val Val Ile Ala
            500                 505                 510

Asp Gln Thr Leu Ser Glu Leu Thr Pro Val Tyr Phe Phe Ile Ser Lys
        515                 520                 525

Gly Ala Asp Gly Arg Ala Glu Thr His Phe Cys Ala Asp Gln Thr Arg
    530                 535                 540

Ser Ser Glu Ala Pro Gly Val Ala Lys Gln Val Tyr Gly Ser Ser Val
545                 550                 555                 560

Pro Val Leu Asp Gly Glu Lys His Ser Met Arg Leu Leu Val Asp His
                565                 570                 575
```

```
Ser Ile Val Glu Ser Phe Ala Gln Gly Gly Arg Thr Val Ile Thr Ser
            580                 585                 590

Arg Ile Tyr Pro Thr Lys Ala Val Asn Gly Ala Ala Arg Leu Phe Val
        595                 600                 605

Phe Asn Asn Ala Thr Gly Ala Ser Val Thr Ala Ser Val Lys Ile Trp
    610                 615                 620

Ser Leu Glu Ser Ala Asn Ile Arg Ser Phe Pro Leu Gln Asp Leu
625                 630                 635


<210> SEQ ID NO 20
<211> LENGTH: 161
<212> TYPE: PRT
<213> ORGANISM: Coffea arabica

<400> SEQUENCE: 20

Ala Val Trp Gly Asn Ile Val Trp Gly His Ala Val Ser Arg Asp Leu
1               5                   10                  15

Ile His Trp Leu Tyr Leu Pro Phe Ala Met Val Pro Asp Arg Pro Phe
            20                  25                  30

Asp Val Asn Gly Val Trp Thr Gly Ser Ala Thr Ile Leu Pro Gly Gly
        35                  40                  45

Lys Ile Val Met Leu Tyr Thr Gly Asp Thr Asp Asp Leu Val Gln Val
    50                  55                  60

Gln Asn Leu Ala Tyr Pro Ala Asn Leu Ser Asp Pro Leu Leu Leu Asp
65                  70                  75                  80

Trp Ile Lys Tyr Pro Gly Asn Pro Val Met Ile Pro Pro Pro Gly Ile
                85                  90                  95

Gly Lys Lys Asp Phe Arg Asp Pro Thr Thr Ala Trp Leu Ala Pro Asp
            100                 105                 110

Gly Thr Lys Trp Leu Val Thr Leu Gly Ser Lys Ile Asn Lys Thr Gly
        115                 120                 125

Ile Ala Met Val Tyr Glu Thr Ser Asp Phe Lys Gly Tyr Arg Leu Leu
    130                 135                 140

Asp Gly Val Leu His Ala Val Pro His Thr Gly Met Trp Glu Cys Pro
145                 150                 155                 160

Asp


<210> SEQ ID NO 21
<211> LENGTH: 558
<212> TYPE: PRT
<213> ORGANISM: Arabidopsis thaliana

<400> SEQUENCE: 21

Met Glu Glu Gly His Lys Glu Pro Leu Val Leu Arg Val Glu Gly Ser
1               5                   10                  15

His Cys Ser Leu Ser Glu Met Asp Asp Phe Asp Leu Thr Arg Ala Leu
            20                  25                  30

Glu Lys Pro Arg Gln Leu Lys Ile Glu Arg Lys Arg Ser Phe Asp Glu
        35                  40                  45

Arg Ser Met Ser Glu Leu Ser Thr Gly Tyr Val Arg Gln Asp Ser Ile
    50                  55                  60

Leu Glu Met Ala His Ser Pro Gly Ser Arg Ser Met Val Asp Thr Pro
65                  70                  75                  80

Leu Ser Val Arg Asn Ser Phe Glu Pro His Pro Met Val Ala Glu Ala
                85                  90                  95

Trp Glu Ala Leu Arg Arg Ser Met Val Phe Phe Arg Gly Gln Pro Val
            100                 105                 110
```

```
Gly Thr Ile Ala Ala Tyr Asp His Ala Ser Glu Glu Val Leu Asn Tyr
        115                 120                 125

Asp Gln Val Phe Val Arg Asp Phe Val Pro Ser Ala Leu Ala Phe Leu
    130                 135                 140

Met Asn Gly Glu Pro Asp Ile Val Lys Asn Phe Leu Leu Lys Thr Leu
145                 150                 155                 160

Gln Leu Gln Gly Trp Glu Lys Arg Val Asp Arg Phe Lys Leu Gly Glu
                165                 170                 175

Gly Val Met Pro Ala Ser Phe Lys Val Leu His Asp Pro Val Arg Lys
            180                 185                 190

Thr Asp Thr Ile Ile Ala Asp Phe Gly Glu Ser Ala Ile Gly Arg Val
        195                 200                 205

Ala Pro Val Asp Ser Gly Phe Trp Trp Ile Ile Leu Leu Arg Ala Tyr
    210                 215                 220

Thr Lys Ser Thr Gly Asp Leu Thr Leu Ser Glu Thr Pro Glu Cys Gln
225                 230                 235                 240

Arg Gly Met Arg Leu Ile Leu Ser Leu Cys Leu Ser Glu Gly Phe Asp
                245                 250                 255

Thr Phe Pro Thr Leu Leu Cys Ala Asp Gly Cys Ser Met Val Asp Arg
            260                 265                 270

Arg Met Gly Val Tyr Gly Tyr Pro Ile Glu Ile Gln Ala Leu Phe Phe
        275                 280                 285

Met Ala Leu Arg Cys Ala Leu Ser Met Leu Lys Pro Asp Glu Glu Gly
    290                 295                 300

Arg Asp Phe Ile Glu Arg Ile Val Lys Arg Leu His Ala Leu Ser Phe
305                 310                 315                 320

His Met Arg Ser Tyr Phe Trp Leu Asp Phe Gln Gln Leu Asn Asp Ile
                325                 330                 335

Tyr Arg Tyr Lys Thr Glu Glu Tyr Ser His Thr Ala Val Asn Lys Phe
            340                 345                 350

Asn Val Met Pro Asp Ser Ile Pro Asp Trp Val Phe Asp Phe Met Pro
        355                 360                 365

Leu Arg Gly Gly Tyr Phe Val Gly Asn Val Ser Pro Ala Arg Met Asp
    370                 375                 380

Phe Arg Trp Phe Ser Leu Gly Asn Cys Val Ser Ile Leu Ser Ser Leu
385                 390                 395                 400

Ala Thr Pro Asp Gln Ser Met Ala Ile Met Asp Leu Leu Glu His Arg
                405                 410                 415

Trp Glu Glu Leu Val Gly Glu Met Pro Leu Lys Ile Cys Tyr Pro Cys
            420                 425                 430

Ile Glu Ser His Glu Trp Arg Ile Val Thr Gly Cys Asp Pro Lys Asn
        435                 440                 445

Thr Arg Trp Ser Tyr His Asn Gly Gly Ser Trp Pro Val Leu Leu Trp
    450                 455                 460

Thr Leu Thr Ala Ala Cys Ile Lys Thr Gly Arg Pro Gln Ile Ala Arg
465                 470                 475                 480

Arg Ala Ile Asp Leu Ile Glu Ser Arg Leu His Arg Asp Cys Trp Pro
                485                 490                 495

Glu Tyr Tyr Asp Gly Lys Gln Gly Arg Tyr Val Gly Lys Gln Ala Arg
            500                 505                 510

Lys Tyr Gln Thr Trp Ser Ile Ala Gly Tyr Leu Val Ala Lys Met Met
        515                 520                 525

Leu Glu Asp Pro Ser His Ile Gly Met Ile Ser Leu Glu Glu Asp Lys
```

```
    530                 535                 540

Gln Met Lys Pro Val Ile Lys Arg Ser Ala Ser Trp Thr Cys
545                 550                 555


<210> SEQ ID NO 22
<211> LENGTH: 556
<212> TYPE: PRT
<213> ORGANISM: Lotus corniculatus var. japonicus

<400> SEQUENCE: 22

Met Asp Gly Pro Val Gly Leu Lys Lys Ile Ser Ser Gln Cys Ser Ile
1               5                   10                  15

Pro Glu Met Asp Asp Phe Asp Gln Leu Ser Arg Leu Leu Asp Lys Pro
            20                  25                  30

Arg Leu Asn Ile Glu Arg Gln Arg Ser Phe Asp Glu Arg Ser Leu Ser
        35                  40                  45

Glu Leu Ser Gln Gly Phe Ala Arg Ala Gly Val Asp Asn Tyr Glu Asn
    50                  55                  60

Tyr Ser Pro Gly Val Arg Ser Gly Phe Asn Thr Pro Ala Ser Ser Ala
65                  70                  75                  80

Arg Asn Ser Phe Glu Pro His Pro Met Val Ala Asp Ala Trp Glu Ser
                85                  90                  95

Leu Arg Arg Ser Leu Val Tyr Phe Lys Gly Gln Pro Val Gly Thr Ile
            100                 105                 110

Ala Ala Val Asp His Gln Ala Glu Glu Val Leu Asn Tyr Asp Gln Val
        115                 120                 125

Phe Val Arg Asp Phe Val Pro Ser Ala Leu Ala Phe Leu Met Asn Gly
    130                 135                 140

Glu Pro Asp Ile Val Arg Asn Phe Leu Leu Lys Thr Leu His Leu Gln
145                 150                 155                 160

Gly Trp Glu Lys Arg Ile Asp Arg Phe Lys Leu Gly Glu Gly Val Met
                165                 170                 175

Pro Ala Ser Phe Lys Val Leu His Asp Pro Val Arg Lys Thr Asp Thr
            180                 185                 190

Leu Ile Ala Asp Phe Gly Glu Ser Ala Ile Gly Arg Val Ala Pro Val
        195                 200                 205

Asp Ser Gly Phe Trp Trp Ile Ile Leu Leu Arg Ala Tyr Thr Lys Ser
    210                 215                 220

Thr Gly Asp Leu Thr Leu Ala Glu Ser Pro Asp Cys Gln Lys Gly Met
225                 230                 235                 240

Lys Leu Ile Leu Thr Leu Cys Leu Ser Glu Gly Phe Asp Thr Phe Pro
                245                 250                 255

Thr Leu Leu Cys Ala Asp Gly Cys Ser Met Ile Asp Arg Arg Met Gly
            260                 265                 270

Ile Tyr Gly Tyr Pro Ile Glu Ile Gln Ala Leu Phe Phe Met Ala Leu
        275                 280                 285

Arg Cys Ala Leu Ser Met Leu Lys Gln Asp Asp Ala Glu Gly Lys Glu
    290                 295                 300

Cys Val Glu Arg Ile Val Lys Arg Leu His Ala Leu Ser Tyr His Met
305                 310                 315                 320

Arg Gly Tyr Phe Trp Leu Asp Phe Gln Gln Leu Asn Asp Ile Tyr Arg
                325                 330                 335

Tyr Lys Thr Glu Glu Tyr Ser His Thr Ala Val Asn Lys Phe Asn Val
            340                 345                 350

Ile Pro Asp Ser Ile Pro Glu Trp Val Phe Asp Phe Met Pro Thr Arg
```

```
        355                 360                 365

Gly Gly Tyr Phe Ile Gly Asn Val Ser Pro Ala Arg Met Asp Phe Arg
    370                 375                 380

Trp Phe Ala Leu Gly Asn Cys Val Ala Ile Leu Ser Ser Leu Ala Thr
385                 390                 395                 400

Pro Glu Gln Ser Met Ala Ile Met Asp Leu Ile Glu Ala Arg Trp Asp
                405                 410                 415

Glu Leu Val Gly Glu Met Pro Leu Lys Ile Ser Tyr Pro Ala Ile Glu
            420                 425                 430

Ser His Glu Trp Arg Ile Val Thr Gly Cys Asp Pro Lys Asn Thr Arg
        435                 440                 445

Trp Ser Tyr His Asn Gly Gly Ser Trp Pro Val Leu Leu Trp Leu Val
    450                 455                 460

Thr Ala Ala Cys Ile Lys Thr Gly Arg Pro Gln Ile Ala Arg Arg Ala
465                 470                 475                 480

Ile Glu Leu Ala Glu Ser Arg Leu Leu Lys Asp Gly Trp Pro Glu Tyr
                485                 490                 495

Tyr Asp Gly Lys Leu Gly Arg Tyr Val Gly Lys Gln Ala Arg Lys Tyr
            500                 505                 510

Gln Thr Trp Ser Ile Ala Gly Tyr Leu Val Ala Lys Met Met Leu Glu
        515                 520                 525

Asp Pro Ser His Leu Gly Met Ile Ser Leu Glu Glu Asp Lys Gln Met
    530                 535                 540

Lys Pro Val Ile Lys Arg Ser Ser Ser Trp Thr Cys
545                 550                 555


<210> SEQ ID NO 23
<211> LENGTH: 582
<212> TYPE: PRT
<213> ORGANISM: Lycopersicon esculentum

<400> SEQUENCE: 23

Met Glu Ile Leu Arg Lys Ser Ser Ser Leu Trp Ala Leu Pro Ile Leu
1               5                   10                  15

Val Leu Cys Phe Phe Ile Asn Asn Gly Val Phe Val Asp Ala Ser His
            20                  25                  30

Lys Val Tyr Met His Leu Gln Ser Thr Thr Ser His Val Asp Ala Ser
        35                  40                  45

Lys Val His Arg Thr Gly Tyr His Phe Gln Pro Pro Lys Asn Trp Ile
    50                  55                  60

Asn Asp Pro Asn Gly Pro Met Tyr Tyr Asn Gly Val Tyr His Leu Phe
65                  70                  75                  80

Tyr Gln Tyr Asn Pro Lys Gly Ala Thr Trp Gly Asn Ile Val Trp Ala
                85                  90                  95

His Ser Val Ser Lys Asp Leu Ile Asn Trp Ile Pro Leu Glu Pro Ala
            100                 105                 110

Ile Tyr Pro Ser Lys Val Phe Asp Lys Tyr Gly Thr Trp Ser Gly Ser
        115                 120                 125

Ala Thr Ile Leu Pro Gly Asn Lys Pro Val Ile Leu Tyr Thr Gly Ile
    130                 135                 140

Val Asp Ala Asn Lys Thr Gln Val Gln Asn Tyr Ala Ile Pro Ala Asn
145                 150                 155                 160

Met Ser Asp Pro Tyr Leu Arg Lys Trp Ile Lys Pro Asp Asn Asn Pro
                165                 170                 175

Leu Ile Val Ala Asp Lys Asn Ile Asn Lys Ile Gln Phe Arg Asp Pro
```

```
            180                 185                 190

Thr Thr Ala Trp Met Gly Arg Asp Gly Tyr Trp Arg Val Leu Val Gly
        195                 200                 205

Ser Val Arg Asn His Arg Gly Lys Val Ile Met Tyr Lys Ser Asn Lys
    210                 215                 220

Asn Phe Met Lys Trp Thr Lys Ala Lys His Pro Leu His Ser Ala Gln
225                 230                 235                 240

Gly Thr Gly Asn Trp Glu Cys Pro Asp Phe Phe Pro Val Ser Leu Lys
                245                 250                 255

Asn Glu Asn Gly Leu Asp Thr Ser Tyr Asp Gly Lys Asp Val Lys His
            260                 265                 270

Val Leu Lys Val Ser Phe Asp Val Thr Arg Phe Asp His Tyr Thr Val
        275                 280                 285

Gly Thr Tyr Asp Thr Lys Lys Asp Lys Tyr Phe Pro Asp Asn Thr Ser
    290                 295                 300

Ile Asp Gly Trp Lys Gly Leu Arg Leu Asp Tyr Gly Asn Tyr Tyr Ala
305                 310                 315                 320

Ser Lys Thr Phe Phe Asp Ser Gly Lys Asn Arg Arg Ile Leu Leu Gly
                325                 330                 335

Trp Ala Asn Glu Ser Asp Thr Val Asp Asn Asp Val Lys Lys Gly Trp
            340                 345                 350

Ala Gly Val His Pro Ile Pro Arg Lys Ile Trp Leu Asp Pro Ser Gly
        355                 360                 365

Lys Gln Leu Val Gln Trp Pro Val Gln Glu Leu Glu Thr Leu Arg Lys
    370                 375                 380

Lys Lys Val Gln Leu Asn Asn Lys Lys Leu Asn Lys Gly Glu Lys Val
385                 390                 395                 400

Glu Ile Lys Gly Ile Thr Val Ala Gln Ala Asp Val Glu Val Ile Phe
                405                 410                 415

Ser Phe Ala Ser Leu Asp Lys Ala Glu Pro Phe Asp Ser Ser Trp Ala
            420                 425                 430

Asp Leu Tyr Ala Gln Asp Val Cys Ala Ile Lys Gly Ser Thr Val Gln
        435                 440                 445

Gly Gly Leu Gly Pro Phe Gly Leu Leu Thr Leu Ala Ser Lys Asn Leu
    450                 455                 460

Glu Glu Tyr Thr Pro Val Phe Phe Arg Val Phe Lys Ala His Asp Asn
465                 470                 475                 480

Tyr Lys Val Leu Met Cys Ser Asp Ala Ser Arg Ser Ser Leu Lys Asn
                485                 490                 495

Glu Thr Thr Met Tyr Lys Pro Ser Phe Ala Gly Tyr Val Asp Val Asp
            500                 505                 510

Leu Ala Asp Lys Lys Leu Ser Leu Arg Ser Leu Ile Asp Asn Ser Ile
        515                 520                 525

Val Glu Ser Phe Gly Ala Gly Gly Lys Thr Cys Ile Thr Ser Arg Val
    530                 535                 540

Tyr Pro Thr Leu Ala Ile Phe Asp Lys Ala His Leu Phe Ala Phe Asn
545                 550                 555                 560

Asn Gly Ala Glu Thr Ile Thr Ile Glu Thr Leu Asn Ala Trp Ser Met
                565                 570                 575

Ala Asn Ala Lys Leu His
            580
```

<210> SEQ ID NO 24
<211> LENGTH: 584

```
<212> TYPE: PRT
<213> ORGANISM: Lycopersicon esculentum

<400> SEQUENCE: 24

Met Glu Leu Phe Met Lys Asn Ser Ser Leu Trp Gly Leu Lys Phe Tyr
1               5                   10                  15

Leu Phe Cys Leu Phe Ile Ile Leu Ser Asn Ile Asn Arg Ala Phe Ala
            20                  25                  30

Ser His Asn Ile Phe Leu Asp Leu Gln Ser Ser Ser Ala Ile Ser Val
        35                  40                  45

Lys Asn Val His Arg Thr Arg Phe His Phe Gln Pro Pro Lys His Trp
    50                  55                  60

Ile Asn Asp Pro Asn Ala Pro Met Tyr Tyr Asn Gly Val Tyr His Leu
65                  70                  75                  80

Phe Tyr Gln Tyr Asn Pro Lys Gly Ser Val Trp Gly Asn Ile Ile Trp
                85                  90                  95

Ala His Ser Val Ser Lys Asp Leu Ile Asn Trp Ile His Leu Glu Pro
            100                 105                 110

Ala Ile Tyr Pro Ser Lys Lys Phe Asp Lys Tyr Gly Thr Trp Ser Gly
        115                 120                 125

Ser Ser Thr Ile Leu Pro Asn Asn Lys Pro Val Ile Ile Tyr Thr Gly
    130                 135                 140

Val Val Asp Ser Tyr Asn Asn Gln Val Gln Asn Tyr Ala Ile Pro Ala
145                 150                 155                 160

Asn Leu Ser Asp Pro Phe Leu Arg Lys Trp Ile Lys Pro Asn Asn Asn
                165                 170                 175

Pro Leu Ile Val Pro Asp Asn Ser Ile Asn Arg Thr Glu Phe Arg Asp
            180                 185                 190

Pro Thr Thr Ala Trp Met Gly Gln Asp Gly Leu Trp Arg Ile Leu Ile
        195                 200                 205

Ala Ser Met Arg Lys His Arg Gly Met Ala Leu Leu Tyr Arg Ser Arg
    210                 215                 220

Asp Phe Met Lys Trp Ile Lys Ala Gln His Pro Leu His Ser Ser Thr
225                 230                 235                 240

Asn Thr Gly Asn Trp Glu Cys Pro Asp Phe Phe Pro Val Leu Phe Asn
                245                 250                 255

Ser Thr Asn Gly Leu Asp Val Ser Tyr Arg Gly Lys Asn Val Lys Tyr
            260                 265                 270

Val Leu Lys Asn Ser Leu Asp Val Ala Arg Phe Asp Tyr Tyr Thr Ile
        275                 280                 285

Gly Met Tyr His Thr Lys Ile Asp Arg Tyr Ile Pro Asn Asn Asn Ser
    290                 295                 300

Ile Asp Gly Trp Lys Gly Leu Arg Ile Asp Tyr Gly Asn Phe Tyr Ala
305                 310                 315                 320

Ser Lys Thr Phe Tyr Asp Pro Ser Arg Asn Arg Arg Val Ile Trp Gly
                325                 330                 335

Trp Ser Asn Glu Ser Asp Val Leu Pro Asp Asp Glu Ile Lys Lys Gly
            340                 345                 350

Trp Ala Gly Ile Gln Gly Ile Pro Arg Gln Val Trp Leu Asn Leu Ser
        355                 360                 365

Gly Lys Gln Leu Leu Gln Trp Pro Ile Glu Glu Leu Glu Thr Leu Arg
    370                 375                 380

Lys Gln Lys Val Gln Leu Asn Asn Lys Lys Leu Ser Lys Gly Glu Met
385                 390                 395                 400
```

```
Phe Glu Val Lys Gly Ile Ser Ala Ser Gln Ala Asp Val Glu Val Leu
                405                 410                 415

Phe Ser Phe Ser Ser Leu Asn Glu Ala Glu Gln Phe Asp Pro Arg Trp
            420                 425                 430

Ala Asp Leu Tyr Ala Gln Asp Val Cys Ala Ile Lys Gly Ser Thr Ile
        435                 440                 445

Gln Gly Gly Leu Gly Pro Phe Gly Leu Val Thr Leu Ala Ser Lys Asn
    450                 455                 460

Leu Glu Glu Tyr Thr Pro Val Phe Phe Arg Val Phe Lys Ala Gln Lys
465                 470                 475                 480

Ser Tyr Lys Ile Leu Met Cys Ser Asp Ala Arg Arg Ser Ser Met Arg
                485                 490                 495

Gln Asn Glu Ala Met Tyr Lys Pro Ser Phe Ala Gly Tyr Val Asp Val
            500                 505                 510

Asp Leu Glu Asp Met Lys Lys Leu Ser Leu Arg Ser Leu Ile Asp Asn
        515                 520                 525

Ser Val Val Glu Ser Phe Gly Ala Gly Gly Lys Thr Cys Ile Thr Ser
    530                 535                 540

Arg Val Tyr Pro Thr Leu Ala Ile Tyr Asp Asn Ala His Leu Phe Val
545                 550                 555                 560

Phe Asn Asn Gly Ser Glu Thr Ile Thr Ile Glu Thr Leu Asn Ala Trp
                565                 570                 575

Ser Met Asp Ala Cys Lys Met Asn
            580
```

<210> SEQ ID NO 25
<211> LENGTH: 592
<212> TYPE: PRT
<213> ORGANISM: Daucus carota

<400> SEQUENCE: 25

```
Met Gly Val Thr Ile Arg Asn Arg Asn Tyr Asp His Gly Ser Leu Pro
1               5                   10                  15

Phe Leu Gln Ser Leu Leu Ala Ile Leu Leu Val Thr Thr Thr Thr Leu
            20                  25                  30

His Ile Asn Gly Val Glu Ala Phe His Glu Ile His Tyr Asn Leu Gln
        35                  40                  45

Ser Val Gly Ala Glu Asn Val Lys Gln Val His Arg Thr Gly Tyr His
    50                  55                  60

Phe Gln Pro Lys Gln Asn Trp Ile Asn Asp Pro Asn Gly Pro Met Tyr
65                  70                  75                  80

Tyr Lys Gly Val Tyr His Leu Phe Tyr Gln Tyr Asn Pro Lys Gly Ala
                85                  90                  95

Val Trp Gly Asn Ile Val Trp Ala His Ser Val Ser Thr Asp Leu Ile
            100                 105                 110

Asn Trp Thr Pro Leu Glu Pro Ala Ile Phe Pro Ser Lys Pro Phe Asp
        115                 120                 125

Lys Tyr Gly Cys Trp Ser Gly Ser Ala Thr Ile Leu Pro Gly Asn Lys
    130                 135                 140

Pro Val Ile Leu Tyr Thr Gly Ile Val Glu Gly Pro Pro Lys Asn Val
145                 150                 155                 160

Gln Val Gln Asn Tyr Ala Ile Pro Ala Asn Leu Ser Asp Pro Tyr Leu
                165                 170                 175

Arg Lys Trp Ile Lys Pro Asp Asn Asn Pro Leu Val Val Ala Asn Asn
            180                 185                 190
```

```
Gly Glu Asn Ala Thr Ala Phe Arg Asp Pro Thr Thr Ala Trp Leu Asp
        195                 200                 205

Lys Ser Gly His Trp Lys Met Leu Val Gly Ser Lys Arg Asn Arg Arg
    210                 215                 220

Gly Ile Ala Tyr Leu Tyr Arg Ser Lys Asp Phe Ile Lys Trp Thr Lys
225                 230                 235                 240

Ala Lys His Pro Ile His Ser Gln Ala Asn Thr Gly Met Trp Glu Cys
                245                 250                 255

Pro Asp Phe Phe Pro Val Ser Leu Lys Gly Leu Asn Gly Leu Asp Thr
            260                 265                 270

Ser Val Thr Gly Glu Ser Val Lys His Val Leu Lys Val Ser Leu Asp
        275                 280                 285

Leu Thr Arg Tyr Glu Tyr Tyr Thr Val Gly Thr Tyr Leu Thr Asp Lys
    290                 295                 300

Asp Arg Tyr Ile Pro Asp Asn Thr Ser Val Asp Gly Trp Ala Gly Leu
305                 310                 315                 320

Arg Tyr Asp Tyr Gly Asn Phe Tyr Ala Ser Lys Thr Phe Phe Asp Pro
                325                 330                 335

Ser Lys Asn Arg Arg Ile Leu Trp Gly Trp Ala Asn Glu Ser Asp Ser
            340                 345                 350

Thr Ala His Asp Val Ala Lys Gly Trp Ala Gly Ile Gln Leu Ile Pro
        355                 360                 365

Arg Thr Leu Trp Leu Asp Pro Ser Gly Lys Gln Leu Met Gln Trp Pro
    370                 375                 380

Ile Glu Glu Leu Glu Thr Leu Arg Gly Ser Lys Val Lys Phe Ser Arg
385                 390                 395                 400

Lys Gln Asp Leu Ser Lys Gly Ile Leu Val Glu Val Lys Gly Ile Thr
                405                 410                 415

Ala Ala Gln Ala Asp Val Glu Val Thr Phe Ser Phe Lys Ser Leu Ala
            420                 425                 430

Lys Arg Glu Pro Phe Asp Pro Lys Trp Leu Glu Tyr Asp Ala Glu Lys
        435                 440                 445

Ile Cys Ser Leu Lys Gly Ser Thr Val Gln Gly Gly Val Gly Pro Phe
    450                 455                 460

Gly Leu Leu Thr Leu Ala Ser Glu Lys Leu Glu Glu Tyr Thr Pro Val
465                 470                 475                 480

Phe Phe Arg Val Phe Lys Val Gln Asn Thr His Lys Val Leu Met Cys
                485                 490                 495

Ser Asp Ala Thr Arg Ser Ser Leu Lys Glu Gly Leu Tyr Arg Pro Ser
            500                 505                 510

Phe Ala Gly Phe Val Asp Val Asp Leu Ala Thr Asp Lys Lys Ile Ser
        515                 520                 525

Leu Arg Ser Leu Ile Asp Asn Ser Val Val Glu Ser Phe Gly Ala Lys
    530                 535                 540

Gly Lys Thr Cys Ile Ser Ser Arg Val Tyr Pro Thr Leu Ala Val Tyr
545                 550                 555                 560

Glu Asn Ala His Leu Tyr Val Phe Asn Asn Gly Ser Glu Thr Ile Thr
                565                 570                 575

Val Glu Asn Leu Asp Ala Trp Ser Met Lys Lys Pro Leu Arg Met Asn
            580                 585                 590
```

<210> SEQ ID NO 26
<211> LENGTH: 163
<212> TYPE: PRT
<213> ORGANISM: Coffea arabica

<400> SEQUENCE: 26

```
Gly Arg Leu Trp Gly Asn Ile Val Trp Ala His Ser Thr Ser Lys Asp
1               5                   10                  15

Leu Ile Asn Trp Asn Pro His Lys Ala Ala Ile Phe Pro Ser Gln Lys
            20                  25                  30

Gly Asp Val Asn Gly Cys Trp Ser Gly Ser Thr Thr Met Leu Arg Gly
        35                  40                  45

Glu Asn Pro Ala Ile Leu Tyr Thr Gly Ile Asp Pro Lys Asn Gln Gln
    50                  55                  60

Val Gln Asn Leu Ala Val Pro Arg Asn Leu Ser Asp Pro Tyr Leu Ile
65                  70                  75                  80

Glu Trp Val Lys Ser Pro Tyr Asn Pro Leu Met Thr Pro Thr Pro Glu
                85                  90                  95

Asn Lys Ile Asn Ser Ser Ser Phe Arg Asp Pro Thr Thr Ala Trp Leu
            100                 105                 110

Gly Pro Asp Gly Arg Trp Arg Val Ile Val Gly Asn Lys Leu Asn Arg
        115                 120                 125

Arg Gly Lys Ala Leu Leu Tyr Arg Ser Lys Asp Phe Val Arg Trp Thr
    130                 135                 140

Lys Ala Gln His Pro Leu Tyr Ser Ile Gln Gly Thr Gly Met Trp Glu
145                 150                 155                 160

Cys Pro Asp
```

<210> SEQ ID NO 27
<211> LENGTH: 5
<212> TYPE: PRT
<213> ORGANISM: Artificial
<220> FEATURE:
<223> OTHER INFORMATION: BetaF motif of plant invertase

<400> SEQUENCE: 27

```
Asn Asp Pro Asn Gly
1               5
```

<210> SEQ ID NO 28
<211> LENGTH: 6
<212> TYPE: PRT
<213> ORGANISM: Artificial
<220> FEATURE:
<223> OTHER INFORMATION: WECPDF motif for periplasmic or cell-wall-bound invertase

<400> SEQUENCE: 28

```
Trp Glu Cys Pro Asp Phe
1               5
```

<210> SEQ ID NO 29
<211> LENGTH: 176
<212> TYPE: PRT
<213> ORGANISM: Zea mays

<400> SEQUENCE: 29

```
Met Lys Leu Leu Gln Ala Leu Cys Pro Leu Val Ile Leu Leu Ala Cys
1               5                   10                  15

Ser Thr Ser Asn Ala Ser Val Leu Gln Asp Ala Cys Lys Ser Phe Ala
            20                  25                  30

Ala Lys Ile Pro Asp Thr Gly Tyr Ala Tyr Cys Ile Lys Phe Phe Gln
        35                  40                  45

Ala Asp Arg Gly Ser Ala Gly Ala Asp Lys Arg Gly Leu Ala Ala Ile
```

```
    50                  55                  60

Ala Val Arg Ile Met Gly Ala Ala Ala Lys Ser Thr Ala Ser His Ile
65                  70                  75                  80

Ala Ala Leu Arg Ala Ser Glu Lys Asp Lys Glu Arg Leu Ala Cys Leu
                85                  90                  95

Ser Asp Cys Ser Glu Val Tyr Ala Gln Ala Val Asp Gln Thr Gly Val
            100                 105                 110

Ala Ala Lys Gly Ile Ala Ser Gly Thr Pro Arg Gly Arg Ala Asp Ala
        115                 120                 125

Val Met Ala Leu Ser Thr Val Glu Asp Ala Pro Gly Thr Cys Glu Gln
    130                 135                 140

Gly Phe Gln Asp Leu Ser Val Arg Ser Pro Leu Ala Ser Glu Asp Ala
145                 150                 155                 160

Gly Phe Arg Lys Asp Ala Ser Ile Ala Leu Ser Val Thr Ala Ala Leu
                165                 170                 175
```

<210> SEQ ID NO 30
<211> LENGTH: 172
<212> TYPE: PRT
<213> ORGANISM: Nicotiana tabacum

<400> SEQUENCE: 30

```
Met Arg Asn Leu Phe Pro Ile Phe Met Leu Ile Thr Asn Leu Ala Phe
1               5                   10                  15

Asn Asp Asn Asn Asn Ser Asn Asn Ile Ile Asn Thr Thr Cys Arg Ala
            20                  25                  30

Thr Thr Asn Tyr Pro Leu Cys Leu Thr Thr Leu His Ser Asp Pro Arg
        35                  40                  45

Thr Ser Glu Ala Glu Gly Ala Asp Leu Thr Thr Leu Gly Leu Val Met
    50                  55                  60

Val Asp Ala Val Lys Leu Lys Ser Ile Glu Ile Met Lys Ser Ile Lys
65                  70                  75                  80

Lys Leu Glu Lys Ser Asn Pro Glu Leu Arg Leu Pro Leu Ser Gln Cys
                85                  90                  95

Tyr Ile Val Tyr Tyr Ala Val Leu His Ala Asp Val Thr Val Ala Val
            100                 105                 110

Glu Ala Leu Lys Arg Gly Val Pro Lys Phe Ala Glu Asn Gly Met Val
        115                 120                 125

Asp Val Ala Val Glu Ala Glu Thr Cys Glu Phe Ser Phe Lys Tyr Asn
    130                 135                 140

Gly Leu Val Ser Pro Val Ser Asp Met Asn Lys Glu Ile Ile Glu Leu
145                 150                 155                 160

Ser Ser Val Ala Lys Ser Ile Ile Arg Met Leu Leu
                165                 170
```

<210> SEQ ID NO 31
<211> LENGTH: 22
<212> TYPE: DNA
<213> ORGANISM: Artificial
<220> FEATURE:
<223> OTHER INFORMATION: AP1

<400> SEQUENCE: 31

```
gtaatacgac tcactatagg gc                                              22
```

<210> SEQ ID NO 32
<211> LENGTH: 19
<212> TYPE: DNA

<213> ORGANISM: Artificial
<220> FEATURE:
<223> OTHER INFORMATION: AP2

<400> SEQUENCE: 32
actatagggc acgcgtggt 19

<210> SEQ ID NO 33
<211> LENGTH: 27
<212> TYPE: DNA
<213> ORGANISM: Artificial
<220> FEATURE:
<223> OTHER INFORMATION: INV1-GW1

<400> SEQUENCE: 33
gcgatttgac ccattctatc aggtacg 27

<210> SEQ ID NO 34
<211> LENGTH: 27
<212> TYPE: DNA
<213> ORGANISM: Artificial
<220> FEATURE:
<223> OTHER INFORMATION: INV1-GWN1

<400> SEQUENCE: 34
ttgctggttc ttagggtcta tgccagt 27

<210> SEQ ID NO 35
<211> LENGTH: 22
<212> TYPE: DNA
<213> ORGANISM: Artificial
<220> FEATURE:
<223> OTHER INFORMATION: INV3-GW1

<400> SEQUENCE: 35
acaatggtgg atcttggcca gt 22

<210> SEQ ID NO 36
<211> LENGTH: 23
<212> TYPE: DNA
<213> ORGANISM: Artificial
<220> FEATURE:
<223> OTHER INFORMATION: INV3-GWN1

<400> SEQUENCE: 36
tttgtcagca ggtccacgag gag 23

<210> SEQ ID NO 37
<211> LENGTH: 22
<212> TYPE: DNA
<213> ORGANISM: Artificial
<220> FEATURE:
<223> OTHER INFORMATION: INV3-GW2

<400> SEQUENCE: 37
acaatggtgg atcttggcca gt 22

<210> SEQ ID NO 38
<211> LENGTH: 23
<212> TYPE: DNA
<213> ORGANISM: Artificial
<220> FEATURE:
<223> OTHER INFORMATION: INV3-GWN2

<400> SEQUENCE: 38
tttgtcagca ggtccacgag gag 23

<210> SEQ ID NO 39
<211> LENGTH: 30
<212> TYPE: DNA
<213> ORGANISM: Artificial
<220> FEATURE:
<223> OTHER INFORMATION: INV3-GW3

<400> SEQUENCE: 39
ggatacaaaa ccagtaaagc cagaagtgct 30

<210> SEQ ID NO 40
<211> LENGTH: 27
<212> TYPE: DNA
<213> ORGANISM: Artificial
<220> FEATURE:
<223> OTHER INFORMATION: INV3-GWN3

<400> SEQUENCE: 40
gttgcagaat tggattactg ggtactg 27

<210> SEQ ID NO 41
<211> LENGTH: 28
<212> TYPE: DNA
<213> ORGANISM: Artificial
<220> FEATURE:
<223> OTHER INFORMATION: INV3-GW4

<400> SEQUENCE: 41
tccagagtca actggagcaa ctcttcca 28

<210> SEQ ID NO 42
<211> LENGTH: 29
<212> TYPE: DNA
<213> ORGANISM: Artificial
<220> FEATURE:
<223> OTHER INFORMATION: INV3-GWN4

<400> SEQUENCE: 42
atgccagagc acttggcaca aagtctcgt 29

<210> SEQ ID NO 43
<211> LENGTH: 28
<212> TYPE: DNA
<213> ORGANISM: Artificial
<220> FEATURE:
<223> OTHER INFORMATION: INV3-GW5

<400> SEQUENCE: 43
gagagcttcc caagcatcag caaccata 28

<210> SEQ ID NO 44
<211> LENGTH: 28
<212> TYPE: DNA
<213> ORGANISM: Artificial
<220> FEATURE:
<223> OTHER INFORMATION: INV3-GWN5

<400> SEQUENCE: 44
agacaactcg ctcagtgatc tctcatca 28

<210> SEQ ID NO 45
<211> LENGTH: 34
<212> TYPE: DNA
<213> ORGANISM: Artificial
<220> FEATURE:
<223> OTHER INFORMATION: dT(18)-Tail

<400> SEQUENCE: 45
cttccgatcc ctacgctttt tttttttttt tttt 34

<210> SEQ ID NO 46
<211> LENGTH: 23
<212> TYPE: DNA
<213> ORGANISM: Artificial
<220> FEATURE:
<223> OTHER INFORMATION: Inv1-3'a1

<400> SEQUENCE: 46
gacgtgaatg gttgctggtc agg 23

<210> SEQ ID NO 47
<211> LENGTH: 16
<212> TYPE: DNA
<213> ORGANISM: Artificial
<220> FEATURE:
<223> OTHER INFORMATION: Tail-3'RACE

<400> SEQUENCE: 47
cttccgatcc ctacgc 16

<210> SEQ ID NO 48
<211> LENGTH: 23
<212> TYPE: DNA
<213> ORGANISM: Artificial
<220> FEATURE:
<223> OTHER INFORMATION: Inv1-3'a2

<400> SEQUENCE: 48
tacagtgggt gctgagcttt ggt 23

<210> SEQ ID NO 49
<211> LENGTH: 29
<212> TYPE: DNA
<213> ORGANISM: Artificial
<220> FEATURE:
<223> OTHER INFORMATION: INV1-ATG

<400> SEQUENCE: 49
atggctagct tttacctctg gctaatgtg 29

<210> SEQ ID NO 50
<211> LENGTH: 29
<212> TYPE: DNA
<213> ORGANISM: Artificial
<220> FEATURE:
<223> OTHER INFORMATION: INV1-STOP

<400> SEQUENCE: 50
tcaattcttt cgattgatac tggcattct 29

<210> SEQ ID NO 51
<211> LENGTH: 26
<212> TYPE: DNA
<213> ORGANISM: Artificial
<220> FEATURE:
<223> OTHER INFORMATION: INV3-ATG

<400> SEQUENCE: 51
atggagtgtg ttagagaata tcaact 26

<210> SEQ ID NO 52
<211> LENGTH: 26
<212> TYPE: DNA

<213> ORGANISM: Artificial
<220> FEATURE:
<223> OTHER INFORMATION: INV3-STOP

<400> SEQUENCE: 52
tcagcaggtc cacgaggagg atctct 26

<210> SEQ ID NO 53
<211> LENGTH: 22
<212> TYPE: DNA
<213> ORGANISM: Artificial
<220> FEATURE:
<223> OTHER INFORMATION: CcInv1F2

<400> SEQUENCE: 53
gtgaatggtt gctggtcagg at 22

<210> SEQ ID NO 54
<211> LENGTH: 24
<212> TYPE: DNA
<213> ORGANISM: Artificial
<220> FEATURE:
<223> OTHER INFORMATION: CcInv1 R2

<400> SEQUENCE: 54
cagtgtagag aatggctggg tttt 24

<210> SEQ ID NO 55
<211> LENGTH: 19
<212> TYPE: DNA
<213> ORGANISM: Artificial
<220> FEATURE:
<223> OTHER INFORMATION: CcInv1 MGB2

<400> SEQUENCE: 55
aacgacaatg cttcgaggg 19

<210> SEQ ID NO 56
<211> LENGTH: 22
<212> TYPE: DNA
<213> ORGANISM: Artificial
<220> FEATURE:
<223> OTHER INFORMATION: CcInv2 F2

<400> SEQUENCE: 56
agtttatccg accaaggcaa tc 22

<210> SEQ ID NO 57
<211> LENGTH: 19
<212> TYPE: DNA
<213> ORGANISM: Artificial
<220> FEATURE:
<223> OTHER INFORMATION: CcInv2 R2

<400> SEQUENCE: 57
tcacccctgt ggcattgtt 19

<210> SEQ ID NO 58
<211> LENGTH: 13
<212> TYPE: DNA
<213> ORGANISM: Artificial
<220> FEATURE:
<223> OTHER INFORMATION: CcInv2 MGB2

<400> SEQUENCE: 58
cagcgcgact ctt 13

<210> SEQ ID NO 59
<211> LENGTH: 20
<212> TYPE: DNA
<213> ORGANISM: Artificial
<220> FEATURE:
<223> OTHER INFORMATION: CcInv3 F1

<400> SEQUENCE: 59
cttgctgaga gccgtttgct 20

<210> SEQ ID NO 60
<211> LENGTH: 29
<212> TYPE: DNA
<213> ORGANISM: Artificial
<220> FEATURE:
<223> OTHER INFORMATION: CcInv3 R1

<400> SEQUENCE: 60
caatatatct accaagtttg ccatcatag 29

<210> SEQ ID NO 61
<211> LENGTH: 18
<212> TYPE: DNA
<213> ORGANISM: Artificial
<220> FEATURE:
<223> OTHER INFORMATION: CcInv3 MGB1

<400> SEQUENCE: 61
aggacagttg gcctgagt 18

<210> SEQ ID NO 62
<211> LENGTH: 19
<212> TYPE: DNA
<213> ORGANISM: Artificial
<220> FEATURE:
<223> OTHER INFORMATION: CcInvI1 F1

<400> SEQUENCE: 62
cgccgttgag gcagttaga 19

<210> SEQ ID NO 63
<211> LENGTH: 22
<212> TYPE: DNA
<213> ORGANISM: Artificial
<220> FEATURE:
<223> OTHER INFORMATION: CcInvI1 R1

<400> SEQUENCE: 63
ttagctcctt gatgctttgc aa 22

<210> SEQ ID NO 64
<211> LENGTH: 14
<212> TYPE: DNA
<213> ORGANISM: Artificial
<220> FEATURE:
<223> OTHER INFORMATION: CcInvI1 MGB1

<400> SEQUENCE: 64
acaaggcaaa ctca 14

<210> SEQ ID NO 65
<211> LENGTH: 22
<212> TYPE: DNA
<213> ORGANISM: Artificial
<220> FEATURE:
<223> OTHER INFORMATION: CcInvI2 F1

<400> SEQUENCE: 65
aggtgcatga tcagacaatt gc 22

<210> SEQ ID NO 66
<211> LENGTH: 20
<212> TYPE: DNA
<213> ORGANISM: Artificial
<220> FEATURE:
<223> OTHER INFORMATION: CcInvI2 R1

<400> SEQUENCE: 66
gcactgccgg acataaggat 20

<210> SEQ ID NO 67
<211> LENGTH: 14
<212> TYPE: DNA
<213> ORGANISM: Artificial
<220> FEATURE:
<223> OTHER INFORMATION: CcInvI2 MGB1

<400> SEQUENCE: 67
agggcaagaa gctg 14

<210> SEQ ID NO 68
<211> LENGTH: 21
<212> TYPE: DNA
<213> ORGANISM: Artificial
<220> FEATURE:
<223> OTHER INFORMATION: CcInvI3 F1

<400> SEQUENCE: 68
gttactgcaa agccgcgttt a 21

<210> SEQ ID NO 69
<211> LENGTH: 26
<212> TYPE: DNA
<213> ORGANISM: Artificial
<220> FEATURE:
<223> OTHER INFORMATION: CcInvI3R1

<400> SEQUENCE: 69
gaagaaatgc taaggtggct agtttt 26

<210> SEQ ID NO 70
<211> LENGTH: 17
<212> TYPE: DNA
<213> ORGANISM: Artificial
<220> FEATURE:
<223> OTHER INFORMATION: CcInvI3MGB1

<400> SEQUENCE: 70
agcatggaga ttgaagc 17

<210> SEQ ID NO 71
<211> LENGTH: 22
<212> TYPE: DNA
<213> ORGANISM: Artificial
<220> FEATURE:
<223> OTHER INFORMATION: CcInvI4 F1

<400> SEQUENCE: 71
cgattgcaag ctggtgatta tg 22

<210> SEQ ID NO 72
<211> LENGTH: 22
<212> TYPE: DNA

<213> ORGANISM: Artificial
<220> FEATURE:
<223> OTHER INFORMATION: CcInvI4R1

<400> SEQUENCE: 72
ttcagtttga gctgctgatg ct 22

<210> SEQ ID NO 73
<211> LENGTH: 14
<212> TYPE: DNA
<213> ORGANISM: Artificial
<220> FEATURE:
<223> OTHER INFORMATION: CcInvI4MGB1

<400> SEQUENCE: 73
aggcgtgaat atca 14

<210> SEQ ID NO 74
<211> LENGTH: 21
<212> TYPE: DNA
<213> ORGANISM: Artificial
<220> FEATURE:
<223> OTHER INFORMATION: rpl39 F1

<400> SEQUENCE: 74
gaacaggccc atcccttatt g 21

<210> SEQ ID NO 75
<211> LENGTH: 17
<212> TYPE: DNA
<213> ORGANISM: Artificial
<220> FEATURE:
<223> OTHER INFORMATION: rpl39 R1

<400> SEQUENCE: 75
cggcgcttgg cattgta 17

<210> SEQ ID NO 76
<211> LENGTH: 16
<212> TYPE: DNA
<213> ORGANISM: Artificial
<220> FEATURE:
<223> OTHER INFORMATION: rpl39 MGB1

<400> SEQUENCE: 76
atgcgcactg acaaca 16

<210> SEQ ID NO 77
<211> LENGTH: 6
<212> TYPE: PRT
<213> ORGANISM: Artificial
<220> FEATURE:
<223> OTHER INFORMATION: N-DPN-G/A; beta Fructofuranosidase-motif

<400> SEQUENCE: 77

Asn Asp Pro Asn Gly Ala
1 5

<210> SEQ ID NO 78
<211> LENGTH: 6
<212> TYPE: PRT
<213> ORGANISM: Artificial
<220> FEATURE:
<223> OTHER INFORMATION: WECX(P/V)DF; V and P distinguish the Vacuolar and cell-wall (Periplasmic) invertase respectively
<220> FEATURE:
<221> NAME/KEY: MISC_FEATURE
<222> LOCATION: (4)..(4)

```
<223> OTHER INFORMATION: X= P or V

<400> SEQUENCE: 78

Trp Glu Cys Xaa Asp Phe
1               5
```